United States Patent
K C et al.

(10) Patent No.: US 10,759,799 B2
(45) Date of Patent: Sep. 1, 2020

(54) INDAZOLE CONTAINING MACROCYCLES AND THERAPEUTIC USES THEREOF

(71) Applicant: Samumed, LLC, San Diego, CA (US)

(72) Inventors: Sunil Kumar K C, San Diego, CA (US); Gopi Kumar Mittapalli, San Diego, CA (US); Chandramouli Chiruta, San Diego, CA (US); Brian Joseph Hofilena, San Diego, CA (US)

(73) Assignee: Samumed, LLC, San Diego, CA (US)

(*) Notice: Subject to any disclaimer, the term of this patent is extended or adjusted under 35 U.S.C. 154(b) by 0 days.

(21) Appl. No.: 16/440,284

(22) Filed: Jun. 13, 2019

(65) Prior Publication Data

US 2019/0382402 A1 Dec. 19, 2019

Related U.S. Application Data

(60) Provisional application No. 62/685,764, filed on Jun. 15, 2018.

(51) Int. Cl.
| | |
|---|---|
| *C07D 471/04* | (2006.01) |
| *A61P 11/00* | (2006.01) |
| *A61P 35/00* | (2006.01) |
| *C07D 401/12* | (2006.01) |
| *C07D 401/14* | (2006.01) |

(52) U.S. Cl.
CPC ............ *C07D 471/04* (2013.01); *A61P 11/00* (2018.01); *A61P 35/00* (2018.01); *C07D 401/12* (2013.01); *C07D 401/14* (2013.01)

(58) Field of Classification Search
CPC ..................................................... C07D 471/04
USPC ........................................................ 514/303
See application file for complete search history.

(56) References Cited

FOREIGN PATENT DOCUMENTS

| | | |
|---|---|---|
| WO | WO 2011/019651 | 2/2011 |
| WO | WO 2011/084486 | 7/2011 |
| WO | WO 2013/040215 | 3/2013 |
| WO | WO 2013/151708 | 10/2013 |
| WO | WO 2013/166396 | 11/2013 |
| WO | WO 2014/110086 | 7/2014 |

OTHER PUBLICATIONS

International Search Report and Written Opinion in Appln No. PCT/US2019/037024, dated Aug. 16, 2019, 10 pages.

*Primary Examiner* — Taofiq A Solola
(74) *Attorney, Agent, or Firm* — Fish & Richardson P.C.

(57) ABSTRACT

Indazole macrocycle compounds for treating various diseases and pathologies are disclosed. More particularly, the present invention concerns the use of an indazole macrocycle compound or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

16 Claims, No Drawings

INDAZOLE CONTAINING MACROCYCLES AND THERAPEUTIC USES THEREOF

RELATED APPLICATION

This application claims the benefit of U.S. Provisional Application No. 62/685,764, filed Jun. 15, 2018, which is incorporated herein by reference in its entirety.

BACKGROUND

Technical Field

This disclosure relates to inhibitors of one or more proteins in the Wnt pathway, including inhibitors of one or more Wnt proteins, and compositions comprising the same. More particularly, it concerns the use of an indazole macrocycle compound or salts or analogs thereof, in the treatment of disorders characterized by the activation of Wnt pathway signaling (e.g., cancer, abnormal cellular proliferation, angiogenesis, fibrotic disorders, bone or cartilage diseases, and osteoarthritis), the modulation of cellular events mediated by Wnt pathway signaling, as well as genetic diseases and neurological conditions/disorders/diseases due to mutations or dysregulation of the Wnt pathway and/or of one or more of Wnt signaling components. Also provided are methods for treating Wnt-related disease states.

Background

The Wnt growth factor family includes more than 10 genes identified in the mouse and at least 19 genes identified in the human. Members of the Wnt family of signaling molecules mediate many short- and long-range patterning processes during invertebrate and vertebrate development. The Wnt signaling pathway is known for its role in the inductive interactions that regulate growth and differentiation, and it also plays roles in the homeostatic maintenance of post-embryonic tissue integrity. Wnt stabilizes cytoplasmic β-catenin, which stimulates the expression of genes including c-myc, c jun, fra-1, and cyclin D1. In addition, misregulation of Wnt signaling can cause developmental defects and is implicated in the genesis of several human cancers. The Wnt pathway has also been implicated in the maintenance of stem or progenitor cells in a growing list of adult tissues including skin, blood, gut, prostate, muscle, and the nervous system.

SUMMARY

The present disclosure provides methods and reagents, involving contacting a cell with an agent, such as an indazole macrocycle compound, in a sufficient amount to antagonize a Wnt activity, e.g., to reverse or control an aberrant growth state or correct a genetic disorder due to mutations in Wnt signaling components.

Some embodiments disclosed herein include Wnt inhibitors containing an indazole core. Other embodiments disclosed herein include pharmaceutical compositions and methods of treatment using these compounds.

One embodiment disclosed herein includes a compound having the structure of Formula I:

as well as prodrugs and pharmaceutically acceptable salts thereof.

In some embodiments of Formula (I):

Ring A is a 5-6-membered heteroaryl optionally substituted with 1-4 $R^1$;

L is -$L^1$-$L^2$-$L^3$-$L^4$-;

$L^1$ is selected from the group consisting of unsubstituted —($C_{1-3}$ alkylene)-, —$NR^2$—, —$NR^3$(C=O)—, —(C=O)$NR^3$—, and —O—;

$L^2$ is selected from the group consisting of unsubstituted —($C_{1-6}$ alkylene)- and —$NR^2$—;

$L^3$ is selected from the group consisting of unsubstituted —($C_{1-6}$ alkylene)-, —O—, and -carbocyclylene- optionally substituted with one or more halides;

$L^4$ is selected from the group consisting of unsubstituted —($C_{1-6}$ alkylene)-, —O—, —$NR^2$—, —$NR^3$(C=O)—, —(C=O)$NR^3$—, -arylene- optionally substituted with 1-5 $R^4$, and -heteroarylene- optionally substituted with 1-4 $R^5$;

with the proviso that —$NR^2$— and —O— are not adjacent to each other;

with the proviso that two —O— are not adjacent to each other;

with the proviso that two —$NR^3$(C=O)— and/or —(C=O)$NR^3$—, are not adjacent to each other;

each $R^1$ is selected from the group consisting of halide, unsubstituted —($C_{1-3}$ alkyl), unsubstituted —($C_{1-3}$ haloalkyl), and —CN;

each $R^2$ is selected from the group consisting of H and unsubstituted —($C_{1-6}$ alkyl);

each $R^3$ is selected from the group consisting of H and unsubstituted —($C_{1-6}$ alkyl);

each $R^4$ is selected from the group consisting of halide, unsubstituted —($C_{1-6}$ alkyl), unsubstituted —($C_{1-6}$ haloalkyl), and —CN;

each $R^5$ is selected from the group consisting of halide, unsubstituted —($C_{1-6}$ alkyl), unsubstituted —($C_{1-6}$ haloalkyl), and —CN;

$Y^1$, $Y^2$, $Y^3$, $Y^4$, $Y^5$, and $Y^6$ are independently selected from the group consisting of carbon and nitrogen; wherein if $Y^1$ is nitrogen then $Y^2$ and $Y^3$ are CH;

if $Y^2$ is nitrogen then $Y^1$ and $Y^3$ are CH;

if $Y^3$ is nitrogen then $Y^1$ and $Y^2$ are CH;

if $Y^4$ is nitrogen then $Y^5$ and $Y^6$ are CH;

if $Y^5$ is nitrogen then $Y^4$ and $Y^6$ are CH; and if $Y^6$ is nitrogen then $Y^4$ and $Y^5$ are CH.

One embodiment disclosed herein includes a compound having the structure of Formula II:

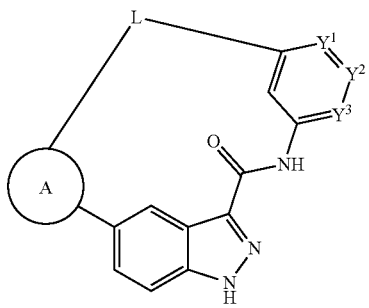

II as well as prodrugs and pharmaceutically acceptable salts thereof.

In some embodiments of Formula (II):

Ring A is a 5-6-membered heteroaryl optionally substituted with 1-3 $R^1$;

L is -$L^1$-$L^2$-$L^3$-$L^4$-

$L^1$ is selected from the group consisting of unsubstituted —($C_{1-3}$ alkylene)-, —$NR^2$—, —$NR^3$(C=O)—, —(C=O)$NR^3$—, and —O—;

$L^2$ is selected from the group consisting of unsubstituted —($C_{1-6}$ alkylene)-, —$NR^2$—, —$NR^3$(C=O)—, and —(C=O)$NR^3$—;

$L^3$ is selected from the group consisting of unsubstituted —($C_{1-6}$ alkylene)-, —O—, and carbocyclylene optionally substituted with one or more halides;

$L^4$ is selected from the group consisting of unsubstituted —($C_{1-6}$ alkylene)-, —O—, —$NR^2$—, —$NR^3$(C=O)—, —(C=O)$NR^3$—, -arylene optionally substituted with 1-5 $R^4$, and -heteroarylene optionally substituted with 1-4 $R^5$;

with the proviso that —$NR^2$— and —O— are not adjacent to each other;

with the proviso that two —O— are not adjacent to each other;

with the proviso that two —$NR^3$(C=O)— and/or —(C=O)$NR^3$—, are not adjacent to each other;

each $R^1$ is selected from the group consisting of halide, unsubstituted —($C_{1-3}$ alkyl), unsubstituted —($C_{1-3}$ haloalkyl), and —CN;

each $R^2$ is selected from the group consisting of H and unsubstituted —($C_{1-6}$ alkyl);

each $R^3$ is selected from the group consisting of H and unsubstituted —($C_{1-6}$ alkyl);

each $R^4$ is selected from the group consisting of halide, unsubstituted —($C_{1-6}$ alkyl), unsubstituted —($C_{1-6}$ haloalkyl), and —CN;

each $R^5$ is selected from the group consisting of halide, unsubstituted —($C_{1-6}$ alkyl), unsubstituted —($C_{1-6}$ haloalkyl), and —CN;

$Y^1$, $Y^2$, and $Y^3$ are independently selected from the group consisting of carbon and nitrogen; wherein
  if $Y^1$ is nitrogen then $Y^2$ and $Y^3$ are CH;
  if $Y^2$ is nitrogen then $Y^1$ and $Y^3$ are CH; and
  if $Y^3$ is nitrogen then $Y^1$ and $Y^2$ are CH.

Some embodiments include stereoisomers and pharmaceutically acceptable salts of a compound of Formulas (I) and/or (II). Some embodiments include pharmaceutically acceptable salts of a compound of Formulas (I) and/or (II).

Some embodiments include pro-drugs of a compound of Formulas (I) and/or (II).

Some embodiments of the present disclosure include pharmaceutical compositions comprising a compound of Formulas (I) and/or (II) and a pharmaceutically acceptable carrier, diluent, or excipient.

Other embodiments disclosed herein include methods of inhibiting one or more members of the Wnt pathway, including one or more Wnt proteins by administering to a patient affected by a disorder or disease in which aberrant Wnt signaling is implicated, such as cancer and other diseases associated with abnormal angiogenesis, cellular proliferation, cell cycling and mutations in Wnt signaling components, a compound according to Formulas (I) and/or (II). Accordingly, the compounds and compositions provided herein can be used to treat cancer, to reduce or inhibit angiogenesis, to reduce or inhibit cellular proliferation and correct a genetic disorder due to mutations in Wnt signaling components.

Non-limiting examples of diseases which can be treated with the compounds and compositions provided herein include a variety of cancers, diabetic retinopathy, pulmonary fibrosis, rheumatoid arthritis, sepsis, ankylosing spondylitis, psoriasis, scleroderma, mycotic and viral infections, osteochondrodysplasia, Alzheimer's disease, lung disease, bone/osteoporotic (wrist, spine, shoulder and hip) fractures, articular cartilage (chondral) defects, degenerative disc disease (or intervertebral disc degeneration), polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Some embodiments of the present disclosure include methods to prepare compounds of Formulas (I) and (II).

It is to be understood that both the foregoing general description and the following detailed description are exemplary and explanatory only and are not restrictive of the invention, as claimed.

DETAILED DESCRIPTION

Provided herein are compositions and methods for inhibiting one or more members of the Wnt pathway, including one or more Wnt proteins.

Some embodiments provided herein relate to a method for treating a disease or disorder including, but not limited to, cancers, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, osteoarthritis, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

In some embodiments, non-limiting examples of bone and cartilage diseases which can be treated with the compounds and compositions provided herein include bone spur (osteophytes), craniosynostosis, fibrodysplasia ossificans progressiva, fibrous dysplasia, giant cell tumor of bone, hip labral tear, meniscal tears, bone/osteoporotic (wrist, spine, shoulder and hip) fractures, articular cartilage (chondral) defects, degenerative disc disease (or intervertebral disc degeneration), osteochondritis dissecans, osteochondroma (bone tumor), osteopetrosis, relapsing polychondritis, and Salter-Harris fractures.

In some embodiments, pharmaceutical compositions are provided that are effective for treatment of a disease of an animal, e.g., a mammal, caused by the pathological activation or mutations of the Wnt pathway. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. Alkylene groups can be saturated or unsaturated (e.g., containing —C=C— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms).

As used herein, "alkenylene" means a bivalent branched, or straight chain chemical group containing only carbon and hydrogen and containing at least one carbon-carbon double bond, such as ethenylene, 1-propenylene, 2-propenylene, 2-methyl-1-propenylene, 1-butenylene, 2-butenylene, and the like. In various embodiments, alkenylene groups can either be unsubstituted or substituted with one or more substituents. Typically, alkenylene groups will comprise 2 to 9 carbon atoms (for example, 2 to 6 carbon atoms, 2 to 4 carbon atoms, or 2 carbon atoms).

As used herein, "alkynylene" means a bivalent branched, or straight chain chemical group containing only carbon and hydrogen and containing at least one carbon-carbon triple bond, such as ethynylene, 1-propynylene, 1-butynylene, 2-butynylene, and the like. In various embodiments, alkynylene groups can either be unsubstituted or substituted with one or more substituents. Typically, alkynylene groups will comprise 2 to 9 carbon atoms (for example, 2 to 6 carbon atoms, 2 to 4 carbon atoms, or 2 carbon atoms).

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that at least one ring in the ring system is not aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, and others. In some embodiments, the heteroaryl is selected from thienyl, pyridinyl, furyl, pyrazolyl, imidazolyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched, alkyl, alkenyl or alkynyl substituted with one or more chloro, bromo, fluoro, and/or iodo atom(s). In some embodiments, a haloalkyl is a fluoroalkyls, wherein one or more of the hydrogen atoms have been substituted by fluoro. In some embodiments, haloalkyls are of 1 to about 3 carbons in length (e.g., 1 to about 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings. Heterocyclyls may be substituted or unsubstituted with one or more substituents. In some embodiments, heterocycles have 3-11 members. In six membered monocyclic heterocycles, the heteroatom(s) are selected from one to three of O, N or S, and wherein when the heterocycle is five membered, it can have one or two heteroatoms selected from O, N, or S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 3-7 members. In six membered monocyclic heterocycles, the heteroatom(s) are selected from one to three of O, N or S, and wherein when the heterocycle is five membered, it can have one or two heteroatoms selected from O, N, or S. Examples of heterocyclyls include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "bicyclic heterocyclyl" means a nonaromatic bicyclic ring system comprising at least one heteroatom in the ring system backbone. Bicyclic heterocyclyls may be substituted or unsubstituted with one or more substituents. In some embodiments, bicyclic heterocycles have 4-11 members with the heteroatom(s) being selected from one to five of O, N or S. Examples of bicyclic heterocyclyls include 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, and the like.

As used herein, "spirocyclic heterocyclyl" means a nonaromatic bicyclic ring system comprising at least one heteroatom in the ring system backbone and with the rings connected through just one atom. Spirocyclic heterocyclyls may be substituted or unsubstituted with one or more substituents. In some embodiments, spirocyclic heterocycles have 5-11 members with the heteroatom(s) being selected from one to five of O, N or S. Examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 2,5-diazaspiro[3.6]decane, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —NH($C_{1-3}$ alkyl), and —N($C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxyl) optionally substituted with one or more of halide, hydroxyl, —$NH_2$, —NH($C_{1-3}$ alkyl), and —N($C_{1-3}$ alkyl)$_2$; —OPO(OH)$_2$; a phosphonate [such as —PO(OH)$_2$ and —PO(OR')$_2$]; —OPO(OR')R''; —NRR'; —C(O)NRR'; —C(NR)NR'R''; —C(NR')R''; a cyano; a nitro; an azido; —SH; —S—R; —OSO$_2$(OR); a sulfonate [such as —SO$_2$(OH) and —SO$_2$(OR)]; —SO$_2$NR'R''; and —SO$_2$R; in which each occurrence of R, R' and R'' are independently selected from H; —($C_{1-9}$ alkyl); $C_{6-10}$ aryl optionally substituted with from 1-3R'''; 5-10 membered heteroaryl having from 1-4 heteroatoms independently selected from N, O, and S and optionally substituted with from 1-3 R'''; $C_{3-7}$ carbocyclyl optionally substituted with from 1-3 R'''; and 3-8 membered heterocyclyl having from 1-4 heteroatoms independently selected from N, O, and S and optionally substituted with from 1-3 R'''; wherein each R''' is independently selected from —($C_{1-6}$ alkyl), —($C_{1-6}$ haloalkyl), a halide (e.g., F), a hydroxyl, —C(O)OR, —C(O)R, —($C_{1-6}$ alkoxy), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some structures described herein may be resonance forms or tautomers of compounds that may be fairly represented by other chemical structures, even when kinetically, the artisan recognizes that such structures are only a very small portion of a sample of such compound(s). Such compounds are clearly contemplated within the scope of this disclosure, though such resonance forms or tautomers are not represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The present disclosure includes all pharmaceutically acceptable isotopically labeled compounds of Formulas (I) and/or (II) wherein one or more atoms are replaced by atoms having the same atomic number, but an atomic mass or mass number different from the atomic mass or mass number which predominates in nature. Examples of isotopes suitable for inclusion in the compounds of the disclosure include, but are not limited to, isotopes of hydrogen, such as $^2$H (deuterium) and $^3$H (tritium), carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

The term "administration" or "administering" refers to a method of providing a dosage of a compound or pharmaceutical composition to a vertebrate or invertebrate, including a mammal, a bird, a fish, or an amphibian, where the method is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A "diagnostic" as used herein is a compound, method, system, or device that assists in the identification or characterization of a health or disease state. The diagnostic can be used in standard assays as is known in the art.

The term "mammal" is used in its usual biological sense. Thus, it specifically includes humans, cattle, horses, monkeys, dogs, cats, mice, rats, cows, sheep, pigs, goats, and non-human primates, but also includes many other species.

The term "pharmaceutically acceptable carrier", "pharmaceutically acceptable diluent" or "pharmaceutically acceptable excipient" includes any and all solvents, co-solvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2010); *Goodman and Gilman's: The Pharmacological Basis of Therapeutics*, 12*th Ed*., The McGraw-Hill Companies.

The term "pharmaceutically acceptable salt" refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

"Patient" as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A "therapeutically effective amount" of a compound as provided herein is one which is sufficient to achieve the desired physiological effect and may vary according to the nature and severity of the disease condition, and the potency of the compound. "Therapeutically effective amount" is also intended to include one or more of the compounds of Formula I in combination with one or more other agents that are effective to treat the diseases and/or conditions described herein. The combination of compounds can be a synergistic combination. Synergy, as described, for example, by Chou and Talalay, *Advances in Enzyme Regulation* (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing or preventing the further development of a disorder, and/or reducing the severity of symptoms that will or are expected to develop.

Compounds

The compounds and compositions described herein can be used as anti-proliferative agents, e.g., anti-cancer and anti-angiogenesis agents, and/or as inhibitors of the Wnt signaling pathway, e.g., for treating diseases or disorders associated with aberrant Wnt signaling. In addition, the compounds can be used as inhibitors of one or more kinases, kinase receptors, or kinase complexes. Such compounds and compositions are also useful for controlling cellular proliferation, differentiation, and/or apoptosis.

Some embodiments of the present disclosure include compounds of Formula I:

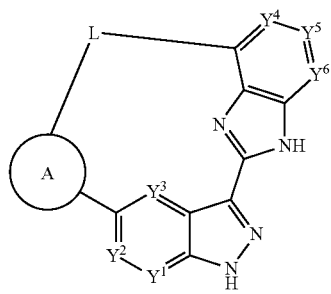

I or salts, pharmaceutically acceptable salts, or prodrugs thereof.

In some embodiments, Ring A is a 5-6-membered heteroaryl optionally substituted with 1-4 $R^1$.

In some embodiments, L is $-L^1-L^2-L^3-L^4-$.

In some embodiments, $L^1$ is selected from the group consisting of unsubstituted $—(C_{1-3}$ alkylene)- (e.g., $C_{1-2}$, $C_1$), $—NR^2—$, $—NR^3(C=O)—$, $—(C=O)NR^3—$, and $—O—$.

In some embodiments of Formula (I), $L^2$ is selected from the group consisting of unsubstituted $—(C_{1-6}$ alkylene)- (e.g., $C_{1-5}$, $C_{1-4}$, $C_{1-3}$, $C_{1-2}$, $C_1$), and $—NR^2—$.

In some embodiments of Formula (I), $L^3$ is selected from the group consisting of unsubstituted $—(C_{1-6}$ alkylene)- (e.g., $C_{1-5}$, $C_{1-4}$, $C_{1-3}$, $C_{1-2}$, $C_1$), $—O—$, and -carbocyclylene- optionally substituted with one or more halides.

In some embodiments of Formula (I), $L^4$ is selected from the group consisting of unsubstituted $—(C_{1-6}$ alkylene)-, $—O—$, $—NR^2—$, $—NR^3(C=O)—$, $—(C=O)NR^3—$, -arylene- optionally substituted with 1-5 (e.g., 1-4, 1-3, 1-2, 1) $R^4$, and -heteroarylene- optionally substituted with 1-4 (e.g., 1-3, 1-2, 1) $R^5$.

In some embodiments of Formula (I), there is the proviso that $—NR^2—$ and $—O—$ are not adjacent to each other.

In some embodiments of Formula (I), there is the proviso that two $—O—$ are not adjacent to each other.

In some embodiments of Formula (I), there is the proviso that two $—NR^3(C=O)—$ and/or $—(C=O)NR^3—$, are not adjacent to each other.

In some embodiments of Formula (I), each $R^1$ is selected from the group consisting of halide (e.g., F, Cl, Br, I), unsubstituted $—(C_{1-3}$ alkyl) (e.g., $C_{1-2}$, $C_1$), unsubstituted $—(C_{1-3}$ haloalkyl) (e.g., $C_{1-2}$, $C_1$), and $—CN$.

In some embodiments of Formula (I), each $R^2$ is selected from the group consisting of H and unsubstituted $—(C_{1-6}$ alkyl) (e.g., $C_{1-5}$, $C_{1-4}$, $C_{1-3}$, $C_{1-2}$, $C_1$).

In some embodiments of Formula (I), each $R^3$ is selected from the group consisting of H and unsubstituted $—(C_{1-6}$ alkyl) (e.g., $C_{1-5}$, $C_{1-4}$, $C_{1-3}$, $C_{1-2}$, $C_1$).

In some embodiments of Formula (I), each $R^4$ is selected from the group consisting of halide (e.g., F, Cl, Br, I), unsubstituted $—(C_{1-6}$ alkyl) (e.g., $C_{1-5}$, $C_{1-4}$, $C_{1-3}$, $C_{1-2}$, $C_1$), unsubstituted $—(C_{1-6}$ haloalkyl) (e.g., $C_{1-5}$, $C_{1-4}$, $C_{1-3}$, $C_{1-2}$, $C_1$), and $—CN$.

In some embodiments of Formula (I), each $R^5$ is selected from the group consisting of halide (e.g., F, Cl, Br, I), unsubstituted $—(C_{1-6}$ alkyl) (e.g., $C_{1-5}$, $C_{1-4}$, $C_{1-3}$, $C_{1-2}$, $C_1$), unsubstituted $—(C_{1-6}$ haloalkyl) (e.g., $C_{1-5}$, $C_{1-4}$, $C_{1-3}$, $C_{1-2}$, $C_1$), and $—CN$.

In some embodiments of Formula (I), $Y^1$, $Y^2$, $Y^3$, $Y^4$, $Y^5$, and $Y^6$ are independently selected from the group consisting of carbon and nitrogen.

In some embodiments of Formula (I), $Y^1$ is nitrogen and $Y^2$ and $Y^3$ are CH.

In some embodiments of Formula (I), $Y^2$ is nitrogen and $Y^1$ and $Y^3$ are CH.

In some embodiments of Formula (I), $Y^3$ is nitrogen and $Y^1$ and $Y^2$ are CH.

In some embodiments of Formula (I), $Y^4$ is nitrogen and $Y^5$ and $Y^6$ are CH.

In some embodiments of Formula (I), $Y^5$ is nitrogen and $Y^4$ and $Y^6$ are CH.

In some embodiments of Formula (I), $Y^6$ is nitrogen and $Y^4$ and $Y^5$ are CH.

Some embodiments of the present disclosure include compounds of Formula II:

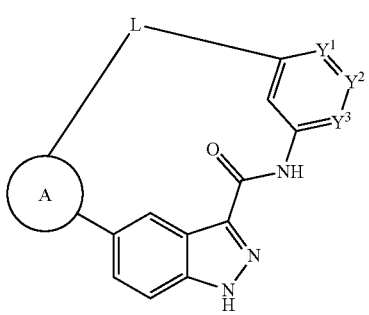

II or salts, pharmaceutically acceptable salts, or prodrugs thereof.

In some embodiments of Formula (II), Ring A is a 5-6-membered heteroaryl optionally substituted with 1-4 $R^1$.

In some embodiments of Formula (II), L is $-L^1-L^2-L^3-L^4-$.

In some embodiments of Formula (II), $L^1$ is selected from the group consisting of unsubstituted $—(C_{1-3}$ alkylene)- (e.g., $C_{1-2}$, $C_1$), $—NR^2—$, $—NR^3(C=O)—$, $—(C=O)NR^3—$, and $—O—$.

In some embodiments of Formula (II), $L^2$ is selected from the group consisting of unsubstituted $—(C_{1-6}$ alkylene)- (e.g., $C_{1-5}$, $C_{1-4}$, $C_{1-3}$, $C_{1-2}$, $C_1$), $—NR^2—$, $—NR^3(C=O)—$, and $—(C=O)NR^3—$.

In some embodiments of Formula (II), $L^3$ is selected from the group consisting of unsubstituted —($C_{1-6}$ alkylene)- (e.g., $C_{1-5}$, $C_{1-4}$, $C_{1-3}$, $C_{1-2}$, $C_1$), —O—, and -carbocyclylene- optionally substituted with one or more halides.

In some embodiments of Formula (II), $L^4$ is selected from the group consisting of unsubstituted —($C_{1-6}$ alkylene)-, —O—, —$NR^2$—, —$NR^3$(C=O)—, —(C=O)$NR^3$—, -arylene- optionally substituted with 1-5 (e.g., 1-4, 1-3, 1-2, 1) $R^4$, and -heteroarylene- optionally substituted with 1-4 (e.g., 1-3, 1-2, 1) $R^5$.

In some embodiments of Formula (II), there is the proviso that —$NR^2$— and —O— are not adjacent to each other.

In some embodiments of Formula (II), there is the proviso that two —O— are not adjacent to each other.

In some embodiments of Formula (II), there is the proviso that two —$NR^3$(C=O)— and/or —(C=O)$NR^3$—, are not adjacent to each other.

In some embodiments of Formula (II), each $R^1$ is selected from the group consisting of halide (e.g., F, Cl, Br, I), unsubstituted —($C_{1-3}$ alkyl) (e.g., $C_{1-2}$, $C_1$), unsubstituted —($C_{1-3}$ haloalkyl) (e.g., $C_{1-2}$, $C_1$), and —CN.

In some embodiments of Formula (II), each $R^2$ is selected from the group consisting of H and unsubstituted —($C_{1-6}$ alkyl) (e.g., $C_{1-5}$, $C_{1-4}$, $C_{1-3}$, $C_{1-2}$, $C_1$).

In some embodiments of Formula (II), each $R^3$ is selected from the group consisting of H and unsubstituted —($C_{1-6}$ alkyl) (e.g., $C_{1-5}$, $C_{1-4}$, $C_{1-3}$, $C_{1-2}$, $C_1$).

In some embodiments of Formula (II), each $R^4$ is selected from the group consisting of halide (e.g., F, Cl, Br, I), unsubstituted —($C_{1-6}$ alkyl) (e.g., $C_{1-5}$, $C_{1-4}$, $C_{1-3}$, $C_{1-2}$, $C_1$), unsubstituted —($C_{1-6}$ haloalkyl) (e.g., $C_{1-5}$, $C_{1-4}$, $C_{1-3}$, $C_{1-2}$, $C_1$), and —CN.

In some embodiments of Formula (II), each $R^5$ is selected from the group consisting of halide (e.g., F, Cl, Br, I), unsubstituted —($C_{1-6}$ alkyl) (e.g., $C_{1-5}$, $C_{1-4}$, $C_{1-3}$, $C_{1-2}$, $C_1$), unsubstituted —($C_{1-6}$ haloalkyl) (e.g., $C_{1-5}$, $C_{1-4}$, $C_{1-3}$, $C_{1-2}$, $C_1$), and —CN.

In some embodiments of Formula (II), $Y^1$, $Y^2$, and $Y^3$ are independently selected from the group consisting of carbon and nitrogen.

In some embodiments of Formula (II), $Y^1$ is nitrogen and $Y^2$ and $Y^3$ are CH.

In some embodiments of Formula (II), $Y^2$ is nitrogen and $Y^1$ and $Y^3$ are CH.

In some embodiments of Formula (II), $Y^3$ is nitrogen and $Y^1$ and $Y^2$ are CH.

In some embodiments of Formulas (I) and (II), Ring A is a 5-membered heteroaryl and is selected from the group consisting of

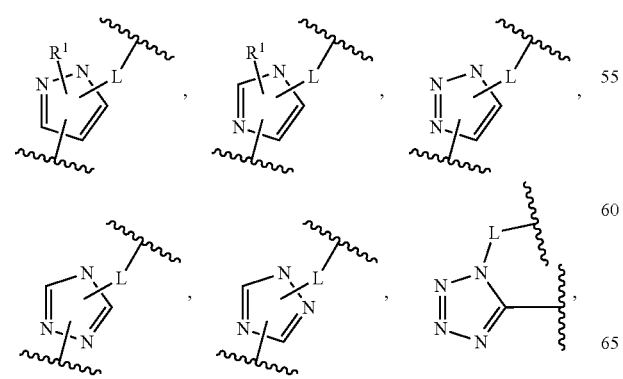

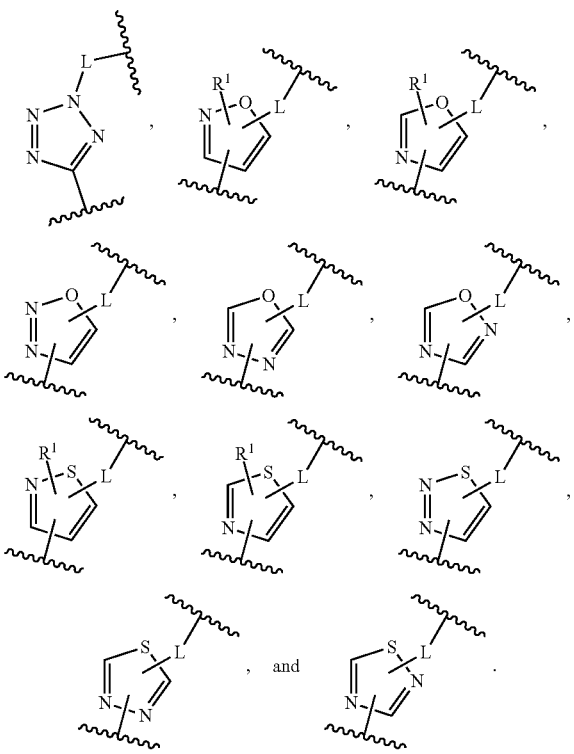

In some embodiments of Formulas (I) and (II), Ring A is a 6-membered heteroaryl and is selected from the group consisting of

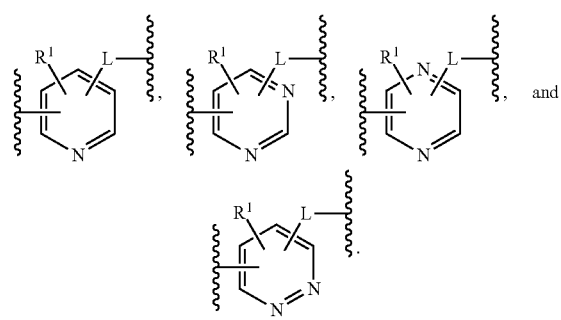

In some embodiments of Formulas (I) and (II), Ring A is a 5-6-membered heteroaryl and is selected from the group consisting of

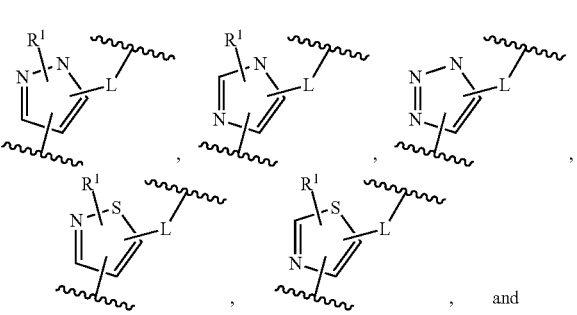

-continued

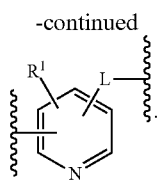

In some embodiments of Formulas (I) and (II), Ring A is a 5-6-membered heteroaryl and is selected from the group consisting of

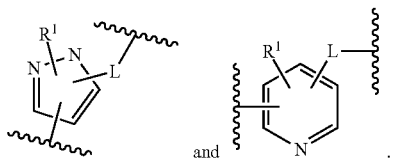

In some embodiments of Formulas (I) and (II), $L^1$ is selected from the group consisting of —(CH$_2$)—, —NH—, —NMe-, —NH(C=O)—, —(C=O)NH—, and —O—; In some embodiments of Formulas (I) and (II), $L^1$ is —(CH$_2$)—; In some embodiments of Formulas (I) and (II), $L^1$ is —NH—; In some embodiments of Formulas (I) and (II), $L^1$ is —NMe-; In some embodiments of Formulas (I) and (II), $L^1$ is —NH(C=O)—; In some embodiments of Formulas (I) and (II), $L^1$ is —(C=O)NH—;

In some embodiments of Formulas (I) and (II), $L^1$ is —O—.

In some embodiments of Formula (I), $L^2$ is selected from the group consisting of —(CH$_2$)—, —(CH$_2$CH$_2$)—, —(CH$_2$CH$_2$CH$_2$)—, —NH—, and —NMe-; In some embodiments of Formulas (I), $L^2$ is —(CH$_2$)—; In some embodiments of Formulas (I), $L^2$ is —(CH$_2$CH$_2$)—; In some embodiments of Formulas (I), $L^2$ is —(CH$_2$CH$_2$CH$_2$)—; In some embodiments of Formulas (I), $L^2$ is —NH—; In some embodiments of Formulas (I), $L^2$ is —NMe-.

In some embodiments of Formula (II), $L^2$ is selected from the group consisting of —(CH$_2$)—, —(CH$_2$CH$_2$)—, —(CH$_2$CH$_2$CH$_2$)—, —NH—, —NMe-, —NH(C=O)—, and —(C=O)NH—; In some embodiments of Formulas (II), $L^2$ is —(CH$_2$)—; In some embodiments of Formulas (II), $L^2$ is —(CH$_2$CH$_2$)—; In some embodiments of Formulas (II), $L^2$ is —(CH$_2$CH$_2$CH$_2$)—; In some embodiments of Formulas (II), $L^2$ is —NH—; In some embodiments of Formulas (II), $L^2$ is —NMe-; In some embodiments of Formula (II), $L^2$ is —NH(C=O)—; In some embodiments of Formula (II), $L^2$ is —(C=O)NH—.

In some embodiments of Formulas (I) and (II), $L^3$ is selected from the group consisting of —(CH$_2$)—, —(CH$_2$CH$_2$)—, —(CH$_2$CH$_2$CH$_2$)—, —(CH$_2$CH$_2$CH$_2$CH$_2$)—, —O—, and

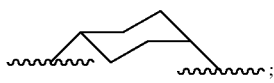

In some embodiments of Formulas (I) and (II), $L^3$ is —(CH$_2$)—; In some embodiments of Formulas (I) and (II), $L^3$ is —(CH$_2$CH$_2$)—; In some embodiments of Formulas (I) and (II), $L^3$ is —(CH$_2$CH$_2$CH$_2$)—; In some embodiments of Formulas (I) and (II), $L^3$ is —(CH$_2$CH$_2$CH$_2$CH$_2$)—; In some embodiments of Formulas (I) and (II), $L^3$ is —O—; In some embodiments of Formulas (I) and (II), $L^3$ is

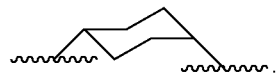

In some embodiments of Formulas (I) and (II), $L^4$ is selected from the group consisting of —(CH$_2$)—, —(CH$_2$CH$_2$)—, —(CH$_2$CH$_2$CH$_2$)—, —(CH$_2$CH$_2$CH$_2$CH$_2$)—, —O—, —NH—, —NMe-, —NH(C=O)—, and —(C=O)NH—,

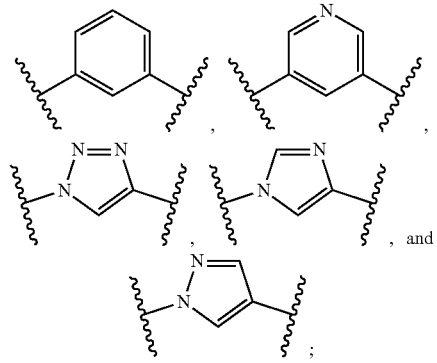

In some embodiments of Formulas (I) and (II), $L^4$ is —(CH$_2$)—; In some embodiments of Formulas (I) and (II), $L^4$ is —(CH$_2$CH$_2$)—; In some embodiments of Formulas (I) and (II), $L^4$ is —(CH$_2$CH$_2$CH$_2$)—; In some embodiments of Formulas (I) and (II), $L^4$ is —(CH$_2$CH$_2$CH$_2$CH$_2$)—; In some embodiments of Formulas (I) and (II), $L^4$ is —O—; In some embodiments of Formulas (I) and (II), $L^4$ is —NH—; In some embodiments of Formulas (I) and (II), $L^4$ is —NMe-; In some embodiments of Formulas (I) and (II), $L^4$ is —NH(C=O)—; In some embodiments of Formulas (I) and (II), $L^4$ is —(C=O)NH—; In some embodiments of Formulas (I) and (II), $L^4$ is

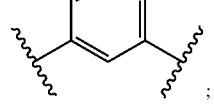

;

In some embodiments of Formulas (I) and (II), $L^4$ is

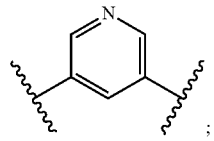

;

In some embodiments of Formulas (I) and (II), $L^4$ is

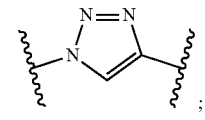

;

In some embodiments of Formulas (I) and (II), $L^4$ is

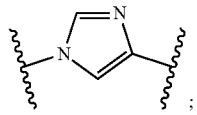

In some embodiments of Formulas (I) and (II), $L^4$ is

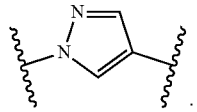 [SMILES: *c1cn(*)nn1]

In some embodiments of Formulas (I) and (II), L is 5-12 atoms in length; in some embodiments of Formulas (I) and (II), L is 5-10 atoms in length; in some embodiments of Formulas (I) and (II), L is 5-9 atoms in length; in some embodiments of Formulas (I) and (II), L is 6-12 atoms in length; in some embodiments of Formulas (I) and (II), L is 6-10 atoms in length; in some embodiments of Formulas (I) and (II), L is 6-9 atoms in length; in some embodiments of Formulas (I) and (II), L is 6-8 atoms in length; in some embodiments of Formulas (I) and (II), L is 7-12 atoms in length; in some embodiments of Formulas (I) and (II), L is 7-10 atoms in length; in some embodiments of Formulas (I) and (II), L is 7-9 atoms in length; in some embodiments of Formulas (I) and (II), L is 7-8 atoms in length; in some embodiments of Formulas (I) and (II), L is 8-12 atoms in length; in some embodiments of Formulas (I) and (II), L is 8-10 atoms in length; in some embodiments of Formulas (I) and (II), L is 8-9 atoms in length; in some embodiments of Formulas (I) and (II), L is 9-12 atoms in length; in some embodiments of Formulas (I) and (II), L is 9-10 atoms in length.

In some embodiments of Formulas (I) and (II), each $R^1$ is selected from the group consisting of F, Me, $CF_3$, and —CN; In some embodiments of Formulas (I) and (II), each $R^1$ is F; In some embodiments of Formulas (I) and (II), each $R^1$ is Me; In some embodiments of Formulas (I) and (II), each $R^1$ is $CF_3$; In some embodiments of Formulas (I) and (II), each $R^1$ is CN; In some embodiments of Formulas (I) and (II), $R^1$ is one F; In some embodiments of Formulas (I) and (II), $R^1$ is one Me; In some embodiments of Formulas (I) and (II), $R^1$ is one $CF_3$; In some embodiments of Formulas (I) and (II), $R^1$ is one CN.

In some embodiments of Formulas (I) and (II), each $R^2$ is selected from the group consisting of H, Me, and Et; In some embodiments of Formulas (I) and (II), each $R^2$ is H; In some embodiments of Formulas (I) and (II), each $R^2$ is Me; In some embodiments of Formulas (I) and (II), each $R^2$ is Et.

In some embodiments of Formulas (I) and (II), each $R^3$ is selected from the group consisting of H, Me, and Et; In some embodiments of Formulas (I) and (II), each $R^3$ is H; In some embodiments of Formulas (I) and (II), each $R^3$ is Me; In some embodiments of Formulas (I) and (II), each $R^3$ is Et.

In some embodiments of Formulas (I) and (II), each $R^4$ is selected from the group consisting of F, Me, $CF_3$, and —CN; In some embodiments of Formulas (I) and (II), each $R^4$ is F; In some embodiments of Formulas (I) and (II), each $R^4$ is Me; In some embodiments of Formulas (I) and (II), each $R^4$ is $CF_3$; In some embodiments of Formulas (I) and (II), each $R^4$ is CN; In some embodiments of Formulas (I) and (II), $R^4$ is one F; In some embodiments of Formulas (I) and (II), $R^4$ is one Me; In some embodiments of Formulas (I) and (II), $R^4$ is one $CF_3$; In some embodiments of Formulas (I) and (II), $R^4$ is one CN.

In some embodiments of Formulas (I) and (II), each $R^5$ is selected from the group consisting of F, Me, $CF_3$, and —CN; In some embodiments of Formulas (I) and (II), each $R^5$ is F; In some embodiments of Formulas (I) and (II), each $R^5$ is Me; In some embodiments of Formulas (I) and (II), each $R^5$ is $CF_3$; In some embodiments of Formulas (I) and (II), each $R^5$ is CN; In some embodiments of Formulas (I) and (II), $R^5$ is one F; In some embodiments of Formulas (I) and (II), $R^5$ is one Me; In some embodiments of Formulas (I) and (II), $R^5$ is one $CF_3$; In some embodiments of Formulas (I) and (II), $R^5$ is one CN.

In some embodiments of Formula (I), $Y^1$ and $Y^4$ are nitrogen and $Y^2$, $Y^3$, $Y^5$ and $Y^6$ are all CH.

In some embodiments of Formula (I), $Y^1$ and $Y^5$ are nitrogen and $Y^2$, $Y^3$, $Y^4$ and $Y^6$ are all CH.

In some embodiments of Formula (I), $Y^1$ and $Y^6$ are nitrogen and $Y^2$, $Y^3$, $Y^4$ and $Y^5$ are all CH.

In some embodiments of Formula (I), $Y^2$ and $Y^4$ are nitrogen and $Y^1$, $Y^3$, $Y^5$, and $Y^6$ are all CH.

In some embodiments of Formula (I), $Y^2$ and $Y^5$ are nitrogen and $Y^1$, $Y^3$, $Y^4$, and $Y^6$ are all CH.

In some embodiments of Formula (I), $Y^2$ and $Y^6$ are nitrogen and $Y^1$, $Y^3$, $Y^4$, and $Y^5$ are all CH.

In some embodiments of Formula (I), $Y^3$ and $Y^4$ are nitrogen and $Y^1$, $Y^2$, $Y^5$, and $Y^6$ are all CH.

In some embodiments of Formula (I), $Y^3$ and $Y^5$ are nitrogen and $Y^1$, $Y^2$, $Y^4$, and $Y^6$ are all CH.

In some embodiments of Formula (I), $Y^3$ and $Y^6$ are nitrogen and $Y^1$, $Y^2$, $Y^4$, and $Y^5$ are all CH.

In some embodiments of Formula (I), $Y^1$ is nitrogen and $Y^2$, $Y^3$, $Y^4$, $Y^5$, and $Y^6$ are all CH.

In some embodiments of Formula (I), $Y^2$ is nitrogen and $Y^1$, $Y^3$, $Y^4$, $Y^5$, and $Y^6$ are all CH.

In some embodiments of Formula (I), $Y^3$ is nitrogen and $Y^1$, $Y^2$, $Y^4$, $Y^5$, and $Y^6$ are all CH.

In some embodiments of Formula (I), $Y^4$ is nitrogen and $Y^1$, $Y^2$, $Y^3$, $Y^5$, and $Y^6$ are all CH.

In some embodiments of Formula (I), $Y^5$ is nitrogen and $Y^1$, $Y^2$, $Y^3$, $Y^4$, and $Y^6$ are all CH.

In some embodiments of Formula (I), $Y^6$ is nitrogen and $Y^1$, $Y^2$, $Y^3$, $Y^4$, and $Y^5$ are all CH.

In some embodiments of Formula (I), $Y^1$, $Y^2$, $Y^3$, $Y^4$, $Y^5$, and $Y^6$ are all CH.

Illustrative compounds of Formulas (I) and (II) are shown in Table 1.

TABLE 1

1

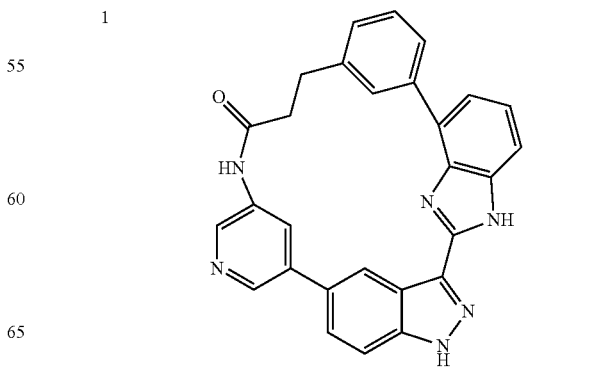

TABLE 1-continued
| | |
|---|---|
| 2 | 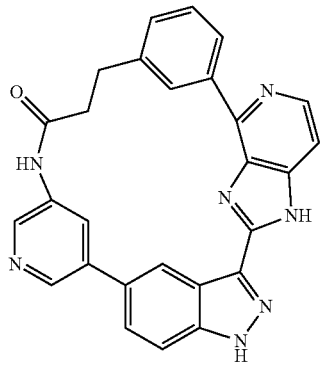 |
| 3 | 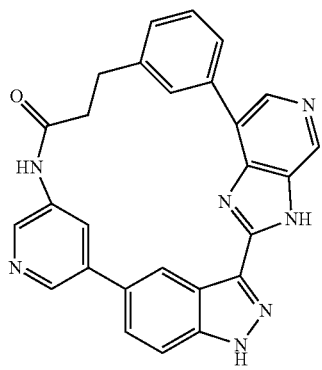 |
| 4 | 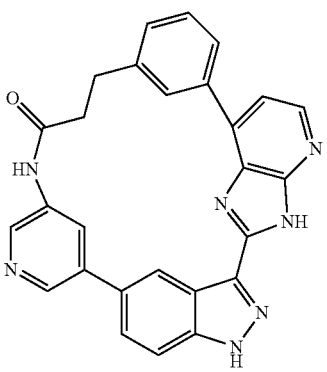 [SMILES: O=C1CCc2cccc(c2)-c2ccnc3[nH]c(nc23)-c2n[nH]c3ccc(cc23)-c2cncc(c2)N1] |
| 5 | 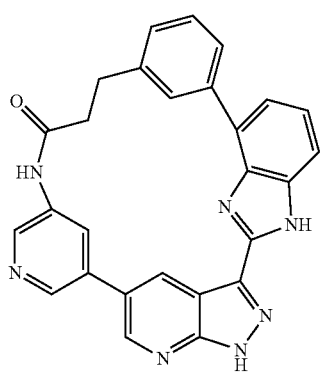 [SMILES: O=C1CCc2cccc(c2)-c2cccc3[nH]c(nc23)-c2n[nH]c3ncc(cc23)-c2cncc(c2)N1] |
| 6 | 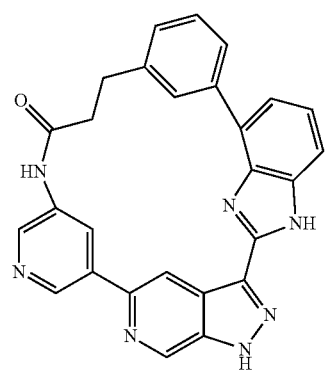 [SMILES: O=C1CCc2cccc(c2)-c2cccc3[nH]c(nc23)-c2n[nH]c3cnc(cc23)-c2cncc(c2)N1] |
| 7 | 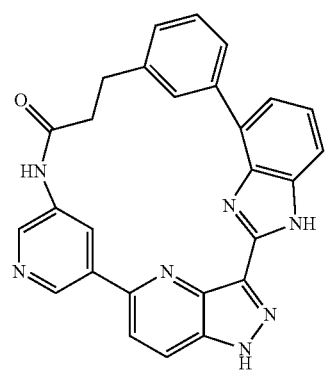 [SMILES: O=C1CCc2cccc(c2)-c2cccc3[nH]c(nc23)-c2n[nH]c3ccc(nc23)-c2cncc(c2)N1] |
| 8 | 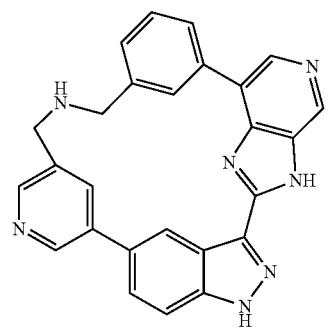 [SMILES: c1cc2cc(c1)-c1cncc3[nH]c(nc13)-c1n[nH]c3ccc(cc13)-c1cncc(c1)CNC2] |
| 9 | 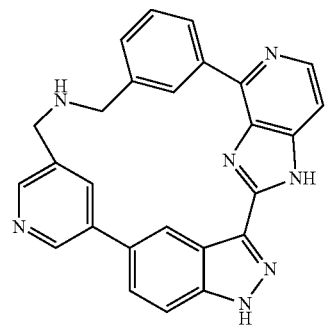 [SMILES: c1cc2cc(c1)-c1cccc3[nH]c(nc13)-c1n[nH]c3ccc(cc13)-c1cncc(c1)CNC2] |

TABLE 1-continued
10
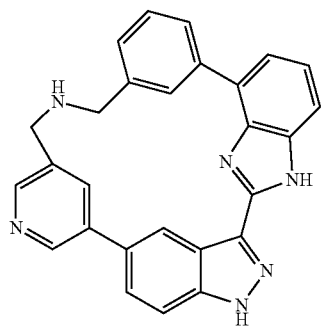
11
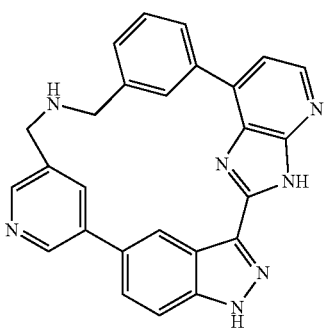 [SMILES: c1cc2cc(c1)-c1ccnc3[nH]c(nc13)-c1n[nH]c3ccc(cc13)-c1cncc(c1)CNC2]
12
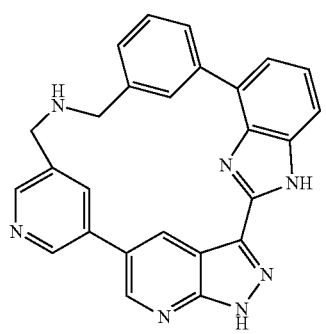 [SMILES: c1cc2cc(c1)-c1cccc3[nH]c(nc13)-c1n[nH]c3ncc(cc13)-c1cncc(c1)CNC2]
13
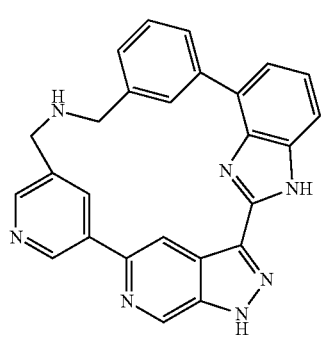
14
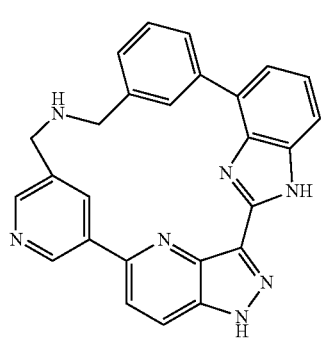 [SMILES: c1cc2cc(c1)-c1cccc3[nH]c(nc13)-c1n[nH]c3ccc(nc13)-c1cncc(c1)CNC2]
TABLE 1-continued
15
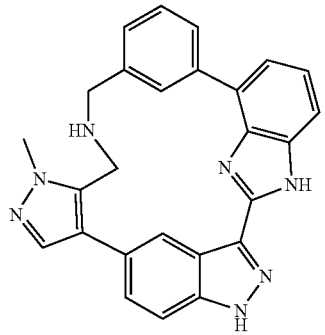 [SMILES: Cn1ncc2c1CNCc1cccc(c1)-c1cccc3[nH]c(nc13)-c1n[nH]c3ccc-2cc13]
16
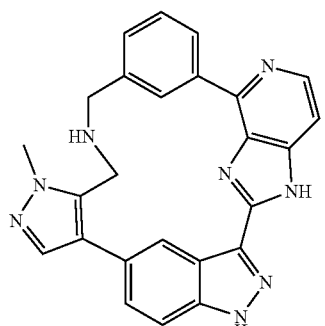
17
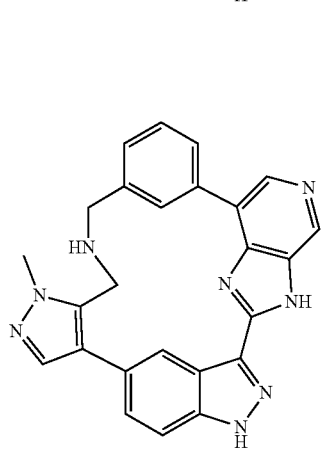
18
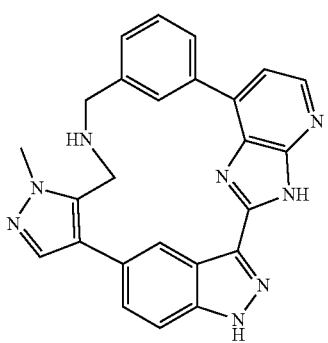 [SMILES: Cn1ncc2c1CNCc1cccc(c1)-c1ccnc3[nH]c(nc13)-c1n[nH]c3ccc-2cc13]

TABLE 1-continued
19
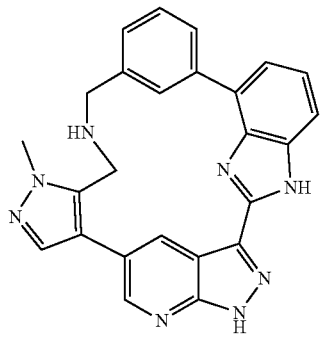 [SMILES: Cn1ncc2c1CNCc1cccc(c1)-c1cccc3[nH]c(nc13)-c1n[nH]c3ncc-2cc13]
20
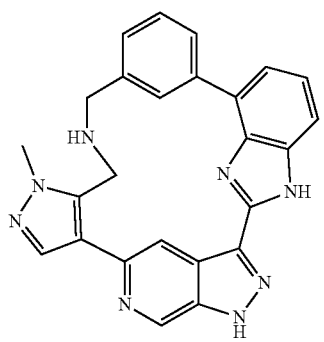 [SMILES: Cn1ncc2c1CNCc1cccc(c1)-c1cccc3[nH]c(nc13)-c1n[nH]c3cnc-2cc13]
21
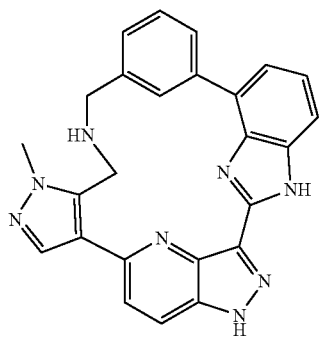 [SMILES: Cn1ncc2c1CNCc1cccc(c1)-c1cccc3[nH]c(nc13)-c1n[nH]c3ccc-2nc13]
22
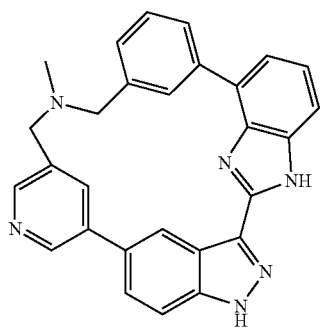
TABLE 1-continued
23
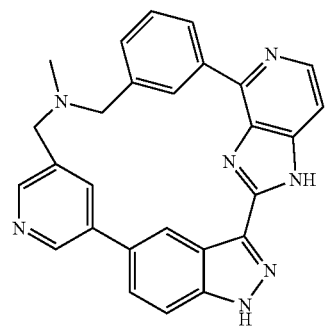 [SMILES: CN1Cc2cncc(c2)-c2ccc3[nH]nc(c3c2)-c2nc3c(cccc3[nH]2)-c2cccc(c2)C1]
24
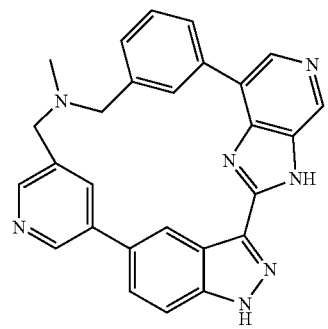 [SMILES: CN1Cc2cncc(c2)-c2ccc3[nH]nc(c3c2)-c2nc3c(cncc3[nH]2)-c2cccc(c2)C1]
25
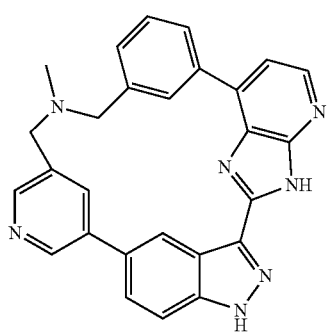 [SMILES: CN1Cc2cncc(c2)-c2ccc3[nH]nc(c3c2)-c2nc3c(ccnc3[nH]2)-c2cccc(c2)C1]
26
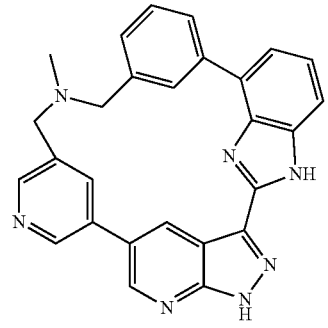 [SMILES: CN1Cc2cncc(c2)-c2cnc3[nH]nc(c3c2)-c2nc3c(cccc3[nH]2)-c2cccc(c2)C1]
27
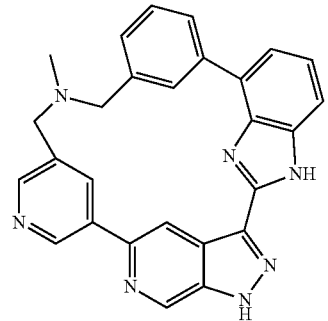

TABLE 1-continued
28
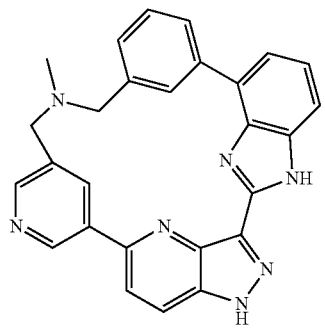
29
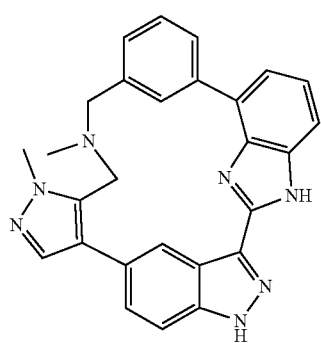 [SMILES: CN1Cc2cccc(c2)-c2cccc3[nH]c(nc23)-c2n[nH]c3ccc(cc23)-c2cnn(C)c2C1]
30
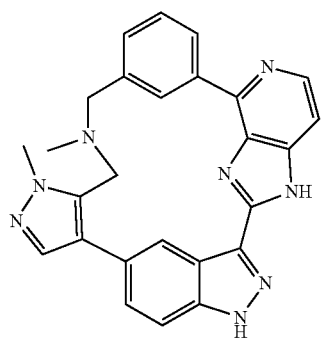 [SMILES: CN1Cc2cccc(c2)-c2nccc3[nH]c(nc23)-c2n[nH]c3ccc(cc23)-c2cnn(C)c2C1]
31
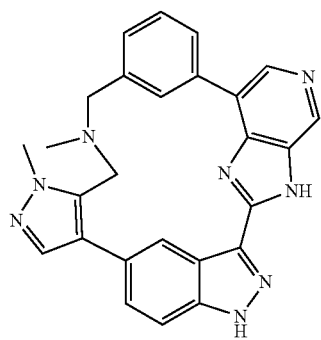 [SMILES: CN1Cc2cccc(c2)-c2cncc3[nH]c(nc23)-c2n[nH]c3ccc(cc23)-c2cnn(C)c2C1]
TABLE 1-continued
32
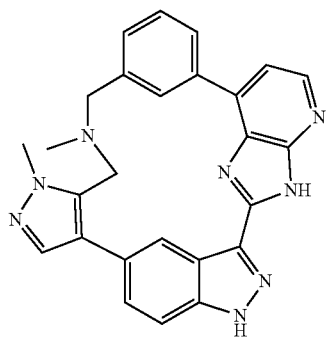 [SMILES: CN1Cc2cccc(c2)-c2ccnc3[nH]c(nc23)-c2n[nH]c3ccc(cc23)-c2cnn(C)c2C1]
33
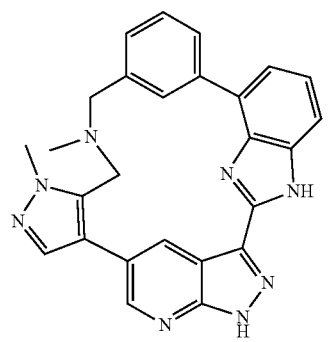 [SMILES: CN1Cc2cccc(c2)-c2cccc3[nH]c(nc23)-c2n[nH]c3ncc(cc23)-c2cnn(C)c2C1]
34
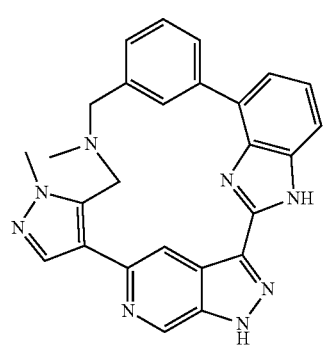 [SMILES: CN1Cc2cccc(c2)-c2cccc3[nH]c(nc23)-c2n[nH]c3cnc(cc23)-c2cnn(C)c2C1]
35
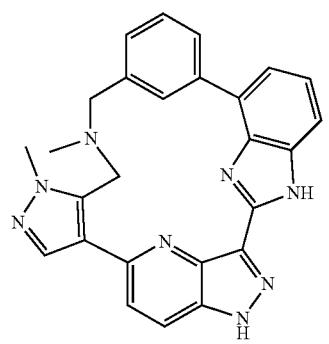 [SMILES: CN1Cc2cccc(c2)-c2cccc3[nH]c(nc23)-c2n[nH]c3ccc(nc23)-c2cnn(C)c2C1]

TABLE 1-continued
36 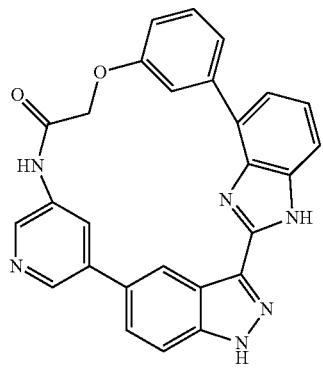 [SMILES: O=C1COc2cccc(c2)-c2cccc3[nH]c(nc23)-c2n[nH]c3ccc(cc23)-c2cncc(c2)N1]
37 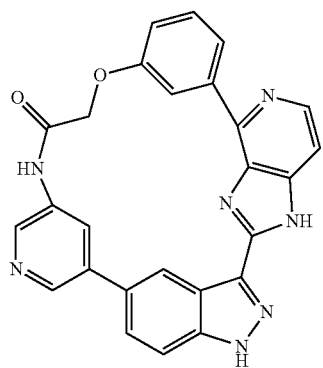 [SMILES: O=C1COc2cccc(c2)-c2nccc3[nH]c(nc23)-c2n[nH]c3ccc(cc23)-c2cncc(c2)N1]
38 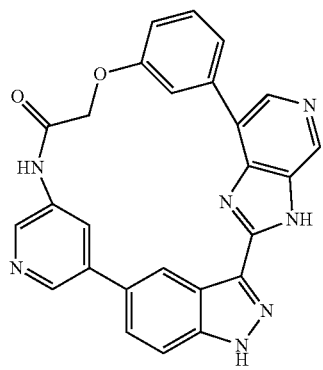
39 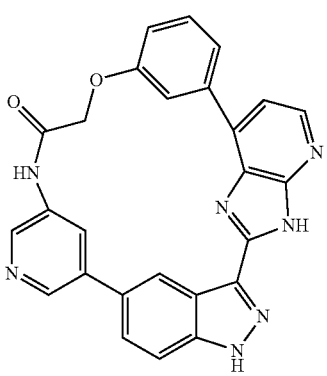 [SMILES: O=C1COc2cccc(c2)-c2ccnc3[nH]c(nc23)-c2n[nH]c3ccc(cc23)-c2cncc(c2)N1]
TABLE 1-continued
40 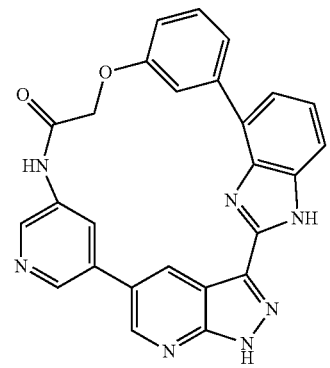
41 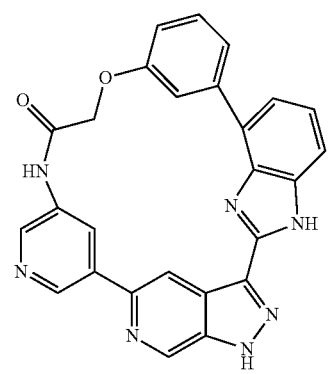 [SMILES: O=C1COc2cccc(c2)-c2cccc3[nH]c(nc23)-c2n[nH]c3cnc(cc23)-c2cncc(c2)N1]
42 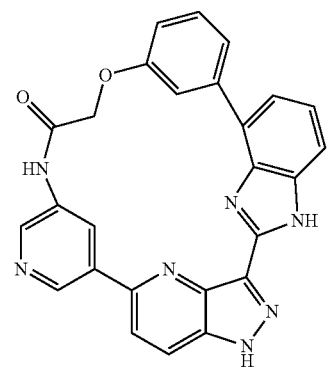 [SMILES: O=C1COc2cccc(c2)-c2cccc3[nH]c(nc23)-c2n[nH]c3ccc(nc23)-c2cncc(c2)N1]
43 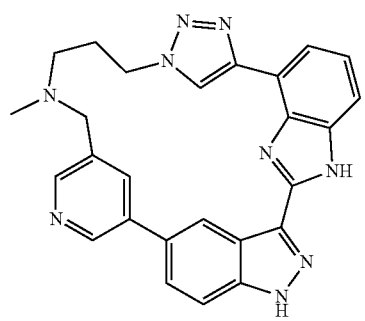 [SMILES: CN1CCCn2cc(nn2)-c2cccc3[nH]c(nc23)-c2n[nH]c3ccc(cc23)-c2cncc(c2)C1]

US 10,759,799 B2
29
TABLE 1-continued
| 44 | 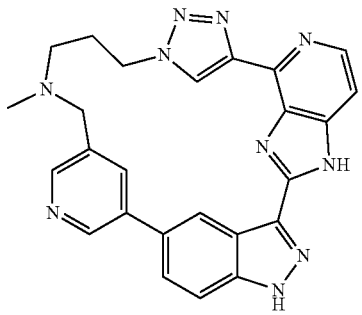 |
| 45 | 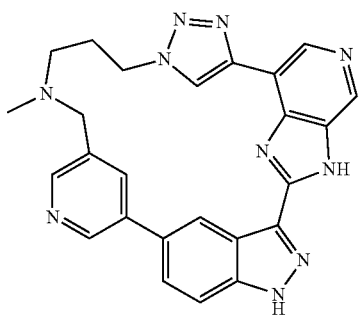 [SMILES: CN1CCCn2cc(nn2)-c2cncc3[nH]c(nc23)-c2n[nH]c3ccc(cc23)-c2cncc(c2)C1] |
| 46 | 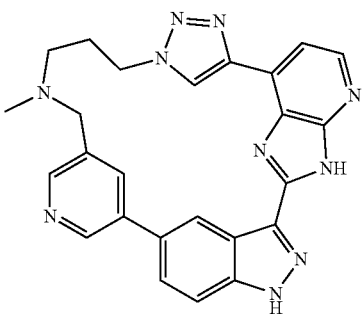 [SMILES: CN1CCCn2cc(nn2)-c2ccnc3[nH]c(nc23)-c2n[nH]c3ccc(cc23)-c2cncc(c2)C1] |
| 47 | 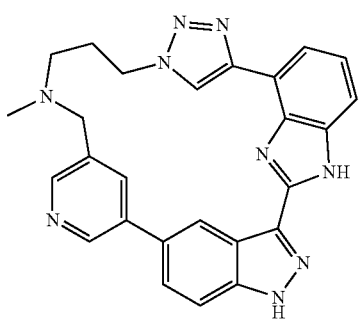 |
| 48 | 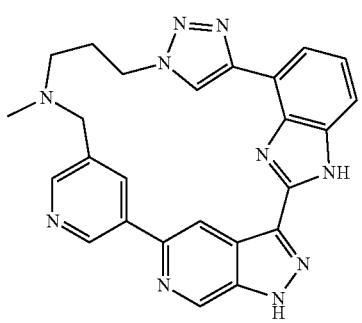 [SMILES: CN1CCCn2cc(nn2)-c2cccc3[nH]c(nc23)-c2n[nH]c3ccc(cc23)-c2cncc(c2)C1] |
30
TABLE 1-continued
| 49 | 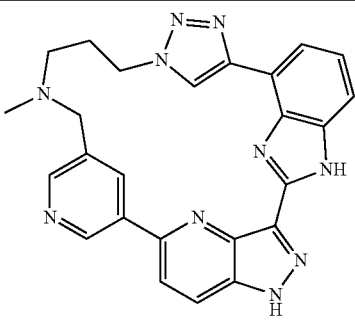 |
| 50 | 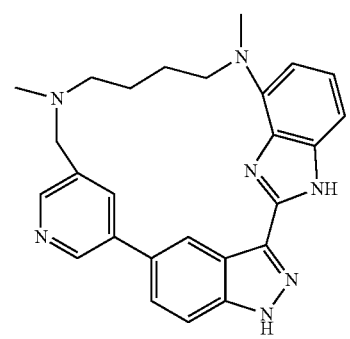 [SMILES: CN1CCCCN(C)c2cccc3[nH]c(nc23)-c2n[nH]c3ccc(cc23)-c2cncc(c2)C1] |
| 51 | 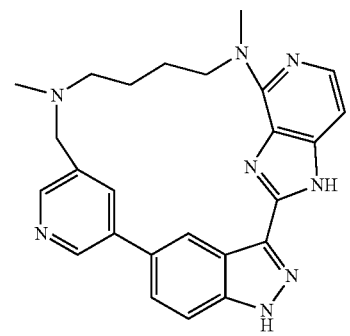 [SMILES: CN1CCCCN(C)c2nccc3[nH]c(nc23)-c2n[nH]c3ccc(cc23)-c2cncc(c2)C1] |
| 52 | 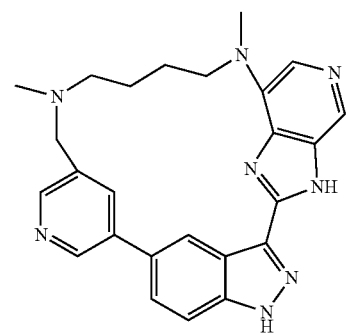 [SMILES: CN1CCCCN(C)c2cncc3[nH]c(nc23)-c2n[nH]c3ccc(cc23)-c2cncc(c2)C1] |
| 53 | 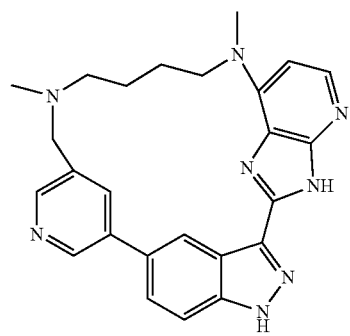 [SMILES: CN1CCCCN(C)c2ccnc3[nH]c(nc23)-c2n[nH]c3ccc(cc23)-c2cncc(c2)C1] |

TABLE 1-continued
54
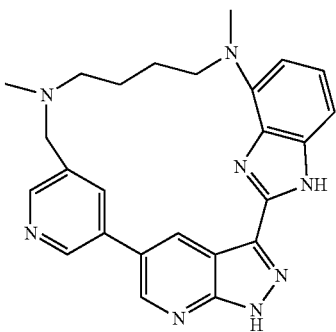 [SMILES: CN1CCCCN(C)c2cccc3[nH]c(nc23)-c2n[nH]c3ncc(cc23)-c2cncc(c2)C1]
55
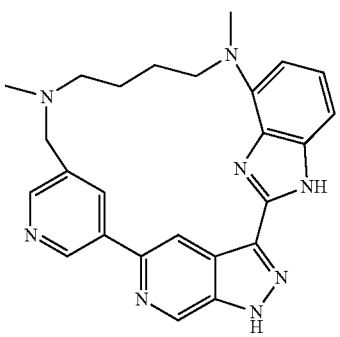 [SMILES: CN1CCCCN(C)c2cccc3[nH]c(nc23)-c2n[nH]c3cnc(cc23)-c2cncc(c2)C1]
56
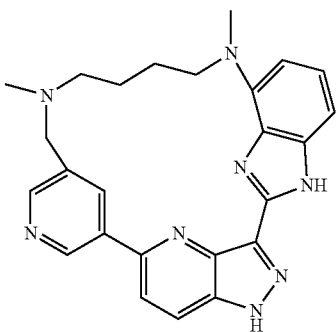 [SMILES: CN1CCCCN(C)c2cccc3[nH]c(nc23)-c2n[nH]c3ccc(nc23)-c2cncc(c2)C1]
57
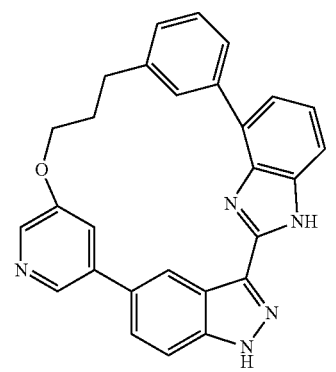
TABLE 1-continued
58
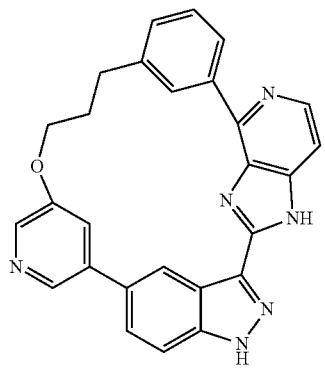 [SMILES: c1cc2cc(c1)-c1nccc3[nH]c(nc13)-c1n[nH]c3ccc(cc13)-c1cncc(c1)OCCC2]
59
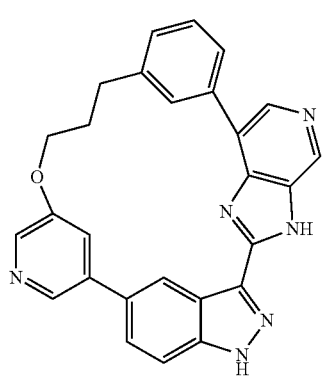 [SMILES: c1cc2cc(c1)-c1cncc3[nH]c(nc13)-c1n[nH]c3ccc(cc13)-c1cncc(c1)OCCC2]
60
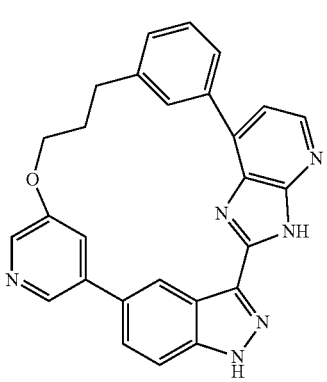 [SMILES: c1cc2cc(c1)-c1ccnc3[nH]c(nc13)-c1n[nH]c3ccc(cc13)-c1cncc(c1)OCCC2]
61
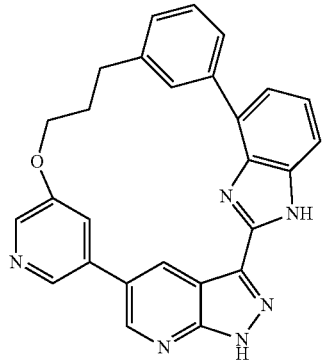

TABLE 1-continued
62 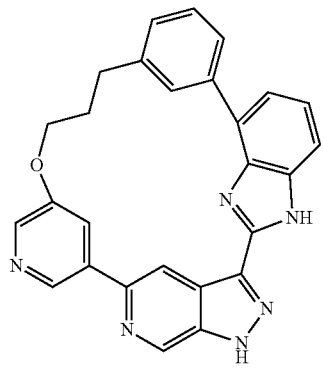
63 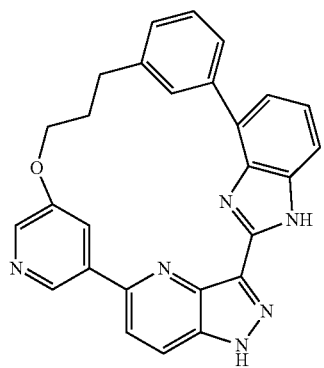
64 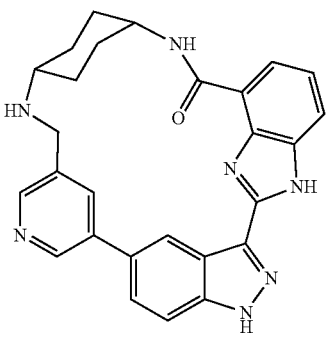
65 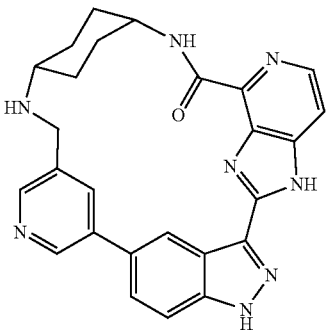
66 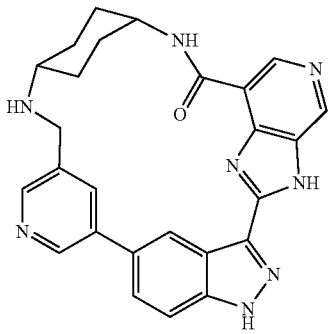
67 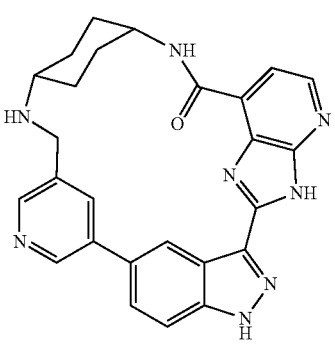 [SMILES: O=C1NC2CCC(CC2)NCc2cncc(c2)-c2ccc3[nH]nc(c3c2)-c2nc3c1ccnc3[nH]2]
68 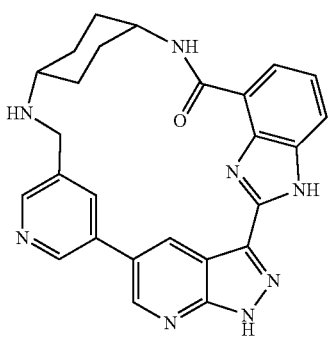 [SMILES: O=C1NC2CCC(CC2)NCc2cncc(c2)-c2cnc3[nH]nc(c3c2)-c2nc3c1cccc3[nH]2]
69 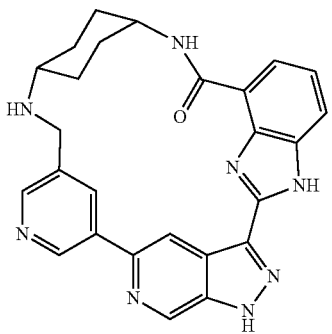

TABLE 1-continued
70 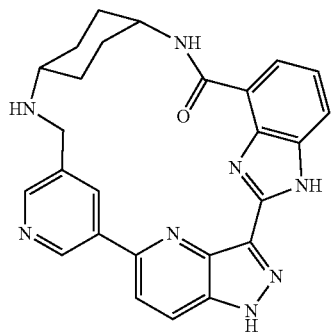 [SMILES: O=C1NC2CCC(CC2)NCc2cncc(c2)-c2ccc3[nH]nc(c3n2)-c2nc3c1cccc3[nH]2]
71 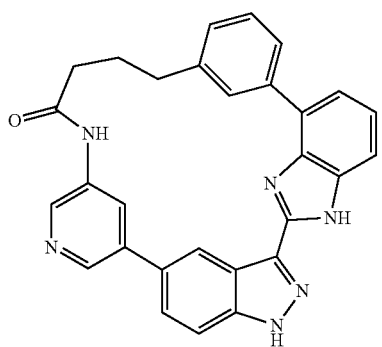 [SMILES: O=C1CCCc2cccc(c2)-c2cccc3[nH]c(nc23)-c2n[nH]c3ccc(cc23)-c2cncc(c2)N1]
72 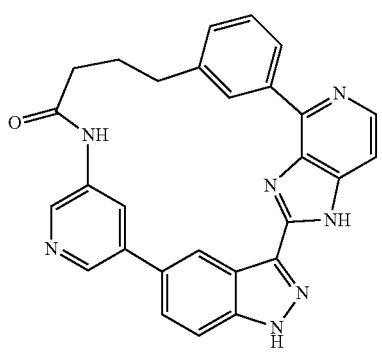 [SMILES: O=C1CCCc2cccc(c2)-c2nccc3[nH]c(nc23)-c2n[nH]c3ccc(cc23)-c2cncc(c2)N1]
73 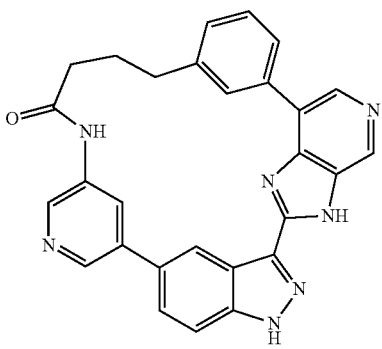
74 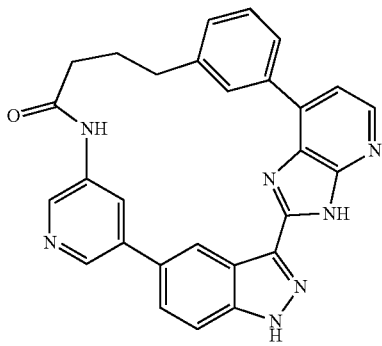 [SMILES: O=C1CCCc2cccc(c2)-c2ccnc3[nH]c(nc23)-c2n[nH]c3ccc(cc23)-c2cncc(c2)N1]
75 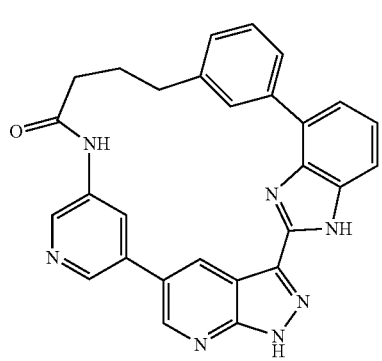 [SMILES: O=C1CCCc2cccc(c2)-c2cccc3[nH]c(nc23)-c2n[nH]c3ncc(cc23)-c2cncc(c2)N1]
76 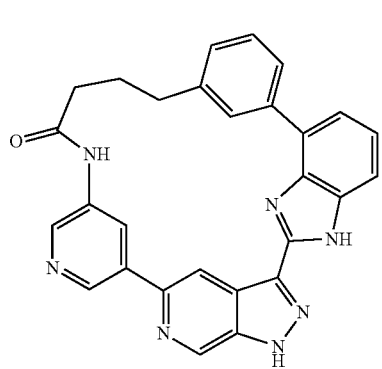 [SMILES: O=C1CCCc2cccc(c2)-c2cccc3[nH]c(nc23)-c2n[nH]c3cnc(cc23)-c2cncc(c2)N1]
77 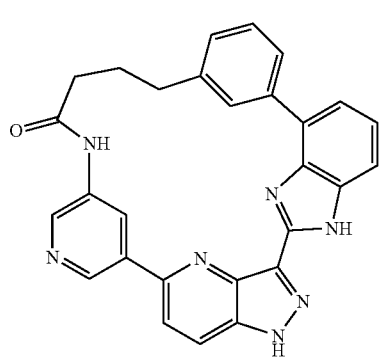 [SMILES: O=C1CCCc2cccc(c2)-c2cccc3[nH]c(nc23)-c2n[nH]c3ccc(nc23)-c2cncc(c2)N1]

TABLE 1-continued
78 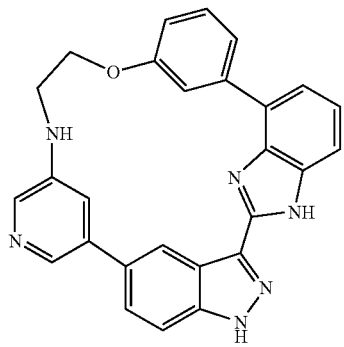
79 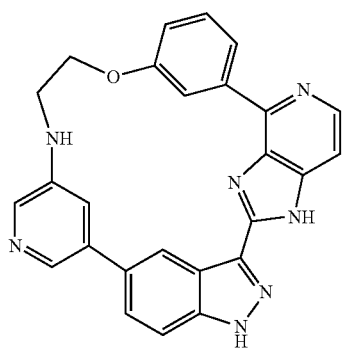 [SMILES: c1cc2cc(c1)-c1nccc3[nH]c(nc13)-c1n[nH]c3ccc(cc13)-c1cncc(c1)NCCO2]
80 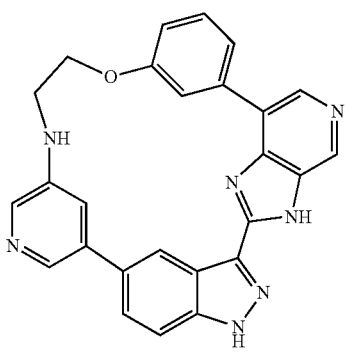 [SMILES: c1cc2cc(c1)-c1cncc3[nH]c(nc13)-c1n[nH]c3ccc(cc13)-c1cncc(c1)NCCO2]
81 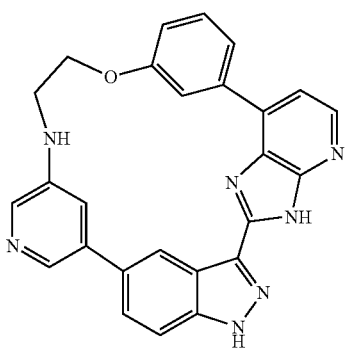 [SMILES: c1cc2cc(c1)-c1ccnc3[nH]c(nc13)-c1n[nH]c3ccc(cc13)-c1cncc(c1)NCCO2]
82 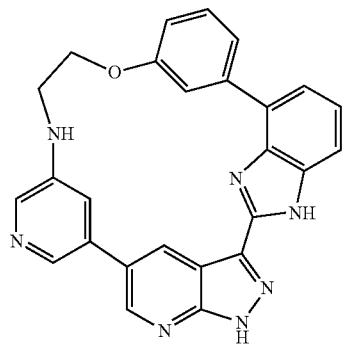 [SMILES: c1cc2cc(c1)-c1cccc3[nH]c(nc13)-c1n[nH]c3ncc(cc13)-c1cncc(c1)NCCO2]
83 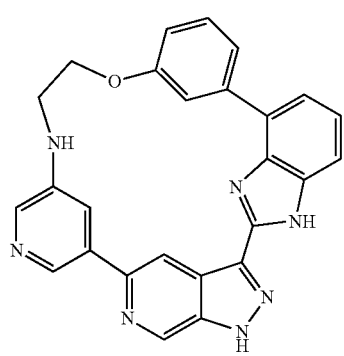 [SMILES: c1cc2cc(c1)-c1cccc3[nH]c(nc13)-c1n[nH]c3cnc(cc13)-c1cncc(c1)NCCO2]
84 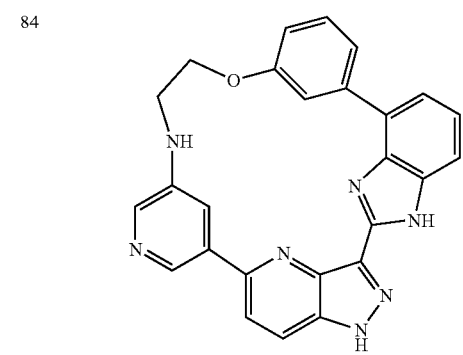
85 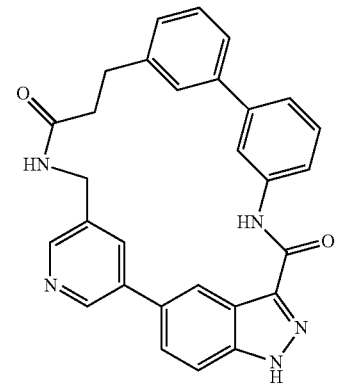 [SMILES: O=C1CCc2cccc(c2)-c2cccc(c2)NC(=O)c2n[nH]c3ccc(cc23)-c2cncc(c2)CN1]

TABLE 1-continued
86 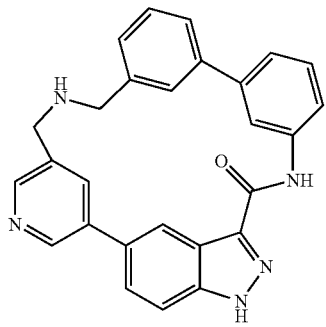 [SMILES: O=C1Nc2cccc(c2)-c2cccc(c2)CNCc2cncc(c2)-c2ccc3[nH]nc1c3c2]
87 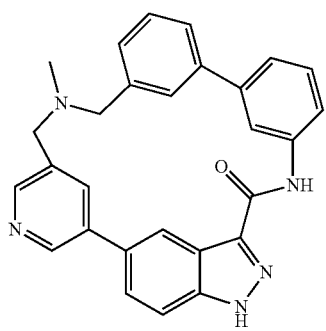 [SMILES: CN1Cc2cccc(c2)-c2cccc(c2)NC(=O)c2n[nH]c3ccc(cc23)-c2cncc(c2)C1]
88 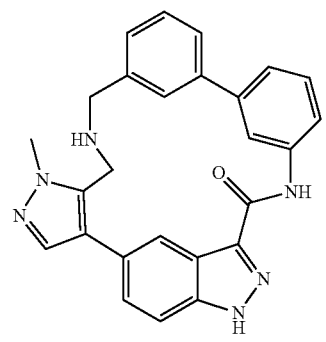 [SMILES: Cn1ncc2c1CNCc1cccc(c1)-c1cccc(c1)NC(=O)c1n[nH]c3ccc-2cc13]
89 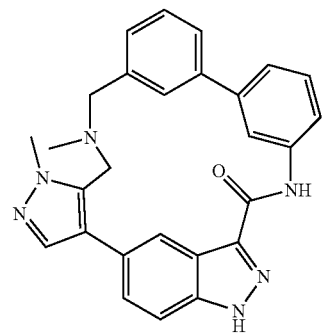 [SMILES: CN1Cc2cccc(c2)-c2cccc(c2)NC(=O)c2n[nH]c3ccc(cc23)-c2cnn(C)c2C1]
90 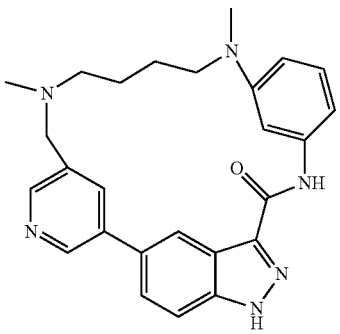 [SMILES: CN1CCCCN(C)c2cccc(c2)NC(=O)c2n[nH]c3ccc(cc23)-c2cncc(c2)C1]
91 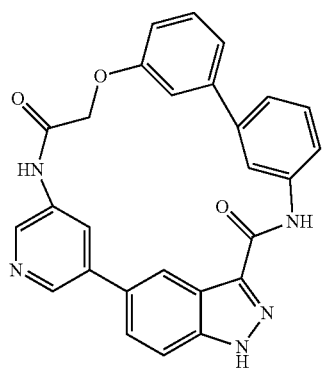 [SMILES: O=C1COc2cccc(c2)-c2cccc(c2)NC(=O)c2n[nH]c3ccc(cc23)-c2cncc(c2)N1]
92 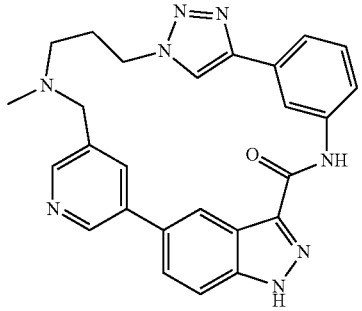
93 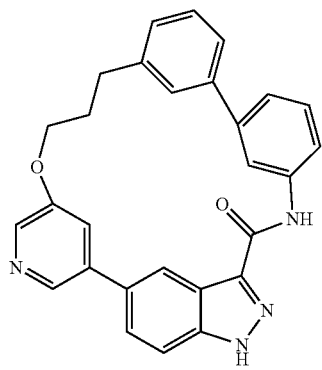 [SMILES: O=C1Nc2cccc(c2)-c2cccc(c2)CCCOc2cncc(c2)-c2ccc3[nH]nc1c3c2]

TABLE 1-continued
94 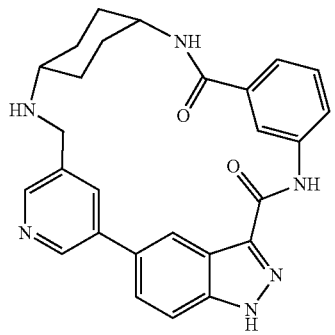 [SMILES: O=C1NC2CCC(CC2)NCc2cncc(c2)-c2ccc3[nH]nc(c3c2)C(=O)Nc2cccc1c2]
95 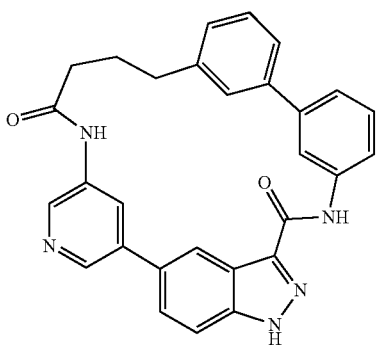 [SMILES: O=C1CCCc2cccc(c2)-c2cccc(c2)NC(=O)c2n[nH]c3ccc(cc23)-c2cncc(c2)N1]
96 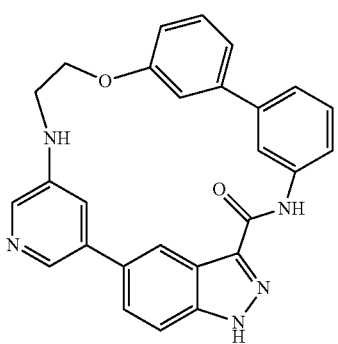 [SMILES: O=C1Nc2cccc(c2)-c2cccc(c2)OCCNc2cncc(c2)-c2ccc3[nH]nc1c3c2]
97 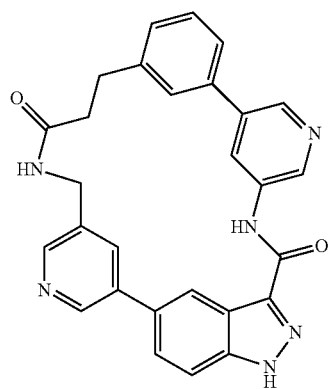 [SMILES: O=C1CCc2cccc(c2)-c2cncc(c2)NC(=O)c2n[nH]c3ccc(cc23)-c2cncc(c2)CN1]
TABLE 1-continued
98 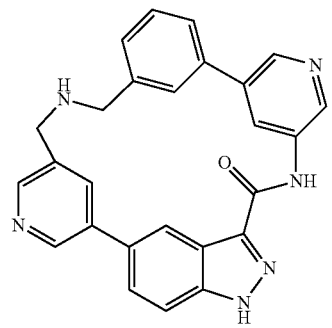
99 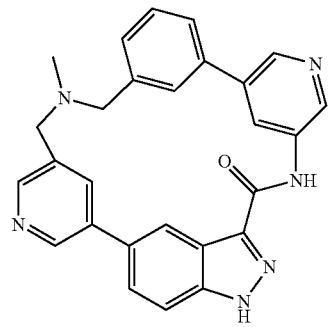 [SMILES: CN1Cc2cccc(c2)-c2cncc(c2)NC(=O)c2n[nH]c3ccc(cc23)-c2cncc(c2)C1]
100 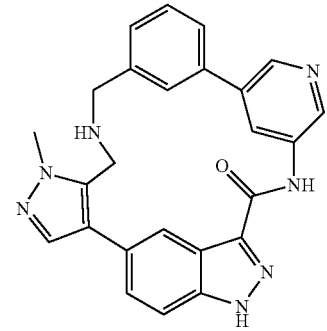 [SMILES: Cn1ncc2c1CNCc1cccc(c1)-c1cncc(c1)NC(=O)c1n[nH]c3ccc-2cc13]
101 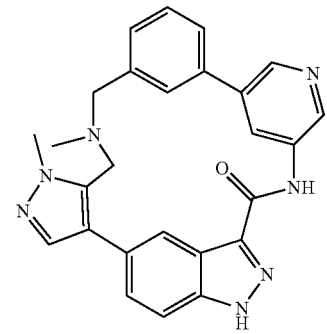 [SMILES: CN1Cc2cccc(c2)-c2cncc(c2)NC(=O)c2n[nH]c3ccc(cc23)-c2cnn(C)c2C1]

TABLE 1-continued
102 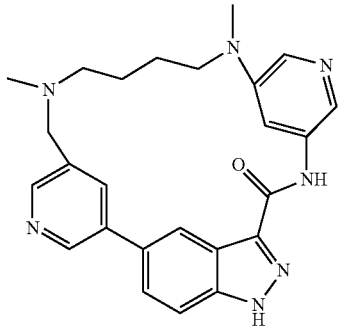 [SMILES: CN1CCCCN(C)c2cncc(c2)NC(=O)c2n[nH]c3ccc(cc23)-c2cncc(c2)C1]
103 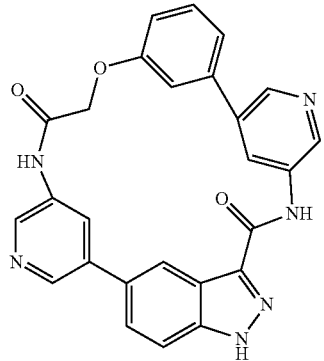
104 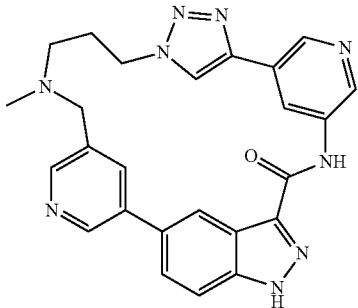 [SMILES: CN1CCCn2cc(nn2)-c2cncc(c2)NC(=O)c2n[nH]c3ccc(cc23)-c2cncc(c2)C1]
105 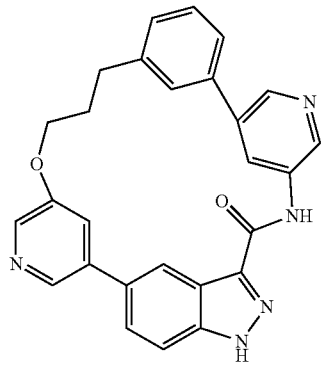 [SMILES: O=C1Nc2cncc(c2)-c2cccc(c2)CCCOc2cncc(c2)-c2ccc3[nH]nc1c3c2]
TABLE 1-continued
106 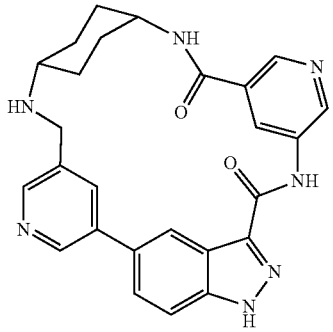 [SMILES: O=C1NC2CCC(CC2)NCc2cncc(c2)-c2ccc3[nH]nc(c3c2)C(=O)Nc2cncc1c2]
107 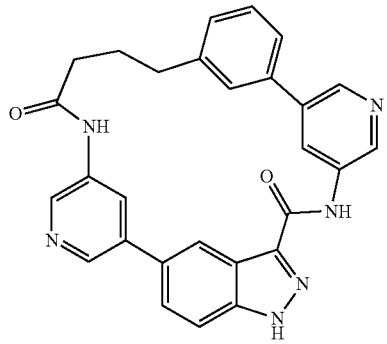 [SMILES: O=C1CCCc2cccc(c2)-c2cncc(c2)NC(=O)c2n[nH]c3ccc(cc23)-c2cncc(c2)N1]
108 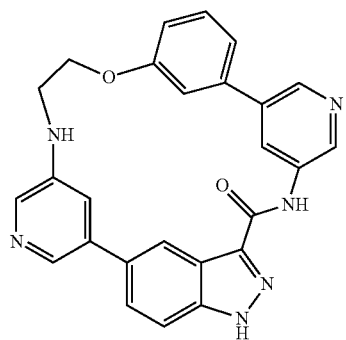 [SMILES: O=C1Nc2cncc(c2)-c2cccc(c2)OCCNc2cncc(c2)-c2ccc3[nH]nc1c3c2]
109 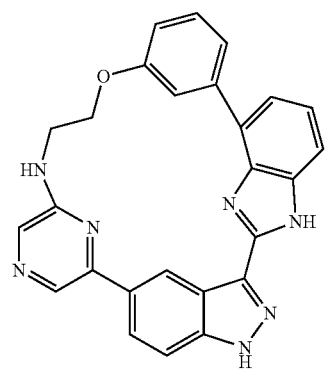 [SMILES: c1cc2cc(c1)-c1cccc3[nH]c(nc13)-c1n[nH]c3ccc(cc13)-c1cncc(n1)NCCO2]

TABLE 1-continued

110 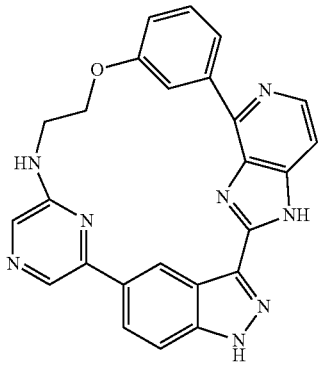 [SMILES: c1cc2cc(c1)-c1nccc3[nH]c(nc13)-c1n[nH]c3ccc(cc13)-c1cncc(n1)NCCO2]

111 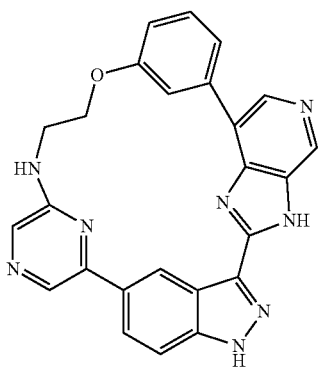 [SMILES: c1cc2cc(c1)-c1cncc3[nH]c(nc13)-c1n[nH]c3ccc(cc13)-c1cncc(n1)NCCO2]

112 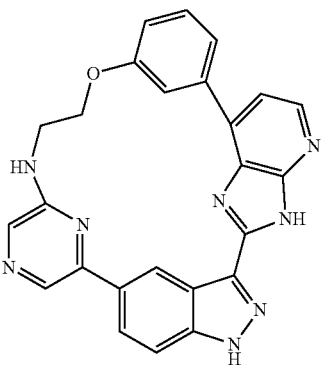 [SMILES: c1cc2cc(c1)-c1ccnc3[nH]c(nc13)-c1n[nH]c3ccc(cc13)-c1cncc(n1)NCCO2]

113 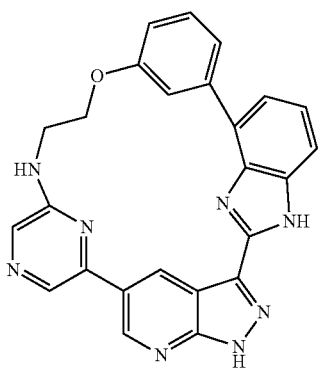

TABLE 1-continued

114 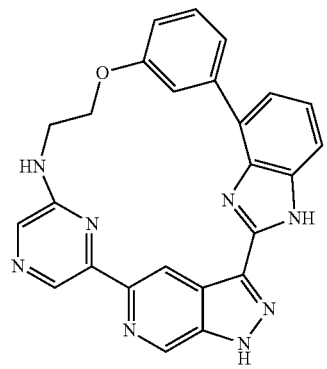 [SMILES: c1cc2cc(c1)-c1cccc3[nH]c(nc13)-c1n[nH]c3cnc(cc13)-c1cncc(n1)NCCO2]

115 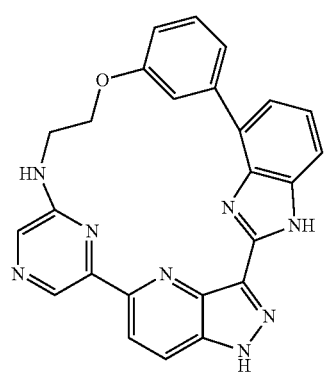 [SMILES: c1cc2cc(c1)-c1cccc3[nH]c(nc13)-c1n[nH]c3ccc(nc13)-c1cncc(n1)NCCO2]

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formulas (I) and/or (II) and other known agents are colorectal cancer, ovarian cancer, retinitis pigmentosa, macular degeneration, diabetic retinopathy, idiopathic pulmonary fibrosis/pulmonary fibrosis, and osteoarthritis.

In some embodiments, colorectal cancer can be treated with a combination of a compound of Formulas (I) and/or (II) and one or more of the following drugs: 5-Fluorouracil (5-FU), which can be administered with the vitamin-like drug leucovorin (also called folinic acid); capecitabine (XELODA®), irinotecan (CAMPOSTAR®), oxaliplatin (ELOXATIN®). Examples of combinations of these drugs which could be further combined with a compound of Formulas (I) and/or (II) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formulas (I) and/or (II) and one or more of the following drugs: Topotecan, Liposomal doxorubicin (DOXIL®), Gemcitabine (GEMZAR®), Cyclophosphamide (CYTOXAN®), Vinorelbine (NAVEL- BINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formulas (I) and/or (II) are TIP (paclitaxel [Taxol], ifosfamide, and cisplatin), VeIP (vinblastine, ifosfamide, and cisplatin) and VIP (etoposide [VP-16], ifosfamide, and cisplatin).

In some embodiments, a compound of Formulas (I) and/or (II) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as vinca alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax in clinical trials, ABT-263, and Gossypol), PARP inhibitors (e.g. Iniparib, Olaparib in clinical trials), PI3K inhibitors (e.g. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); and (k) radiation therapy.

In some embodiments, diabetic retinopathy can be treated with a combination of a compound of Formulas (I) and/or (II) and one or more of the following natural supplements: Bilberry, Butcher's broom, Ginkgo, Grape seed extract, and Pycnogenol (Pine bark).

In some embodiments, idiopathic pulmonary fibrosis/pulmonary fibrosis can be treated with a combination of a compound of Formulas (I) and/or (II) and one or more of the following drugs: pirfenidone (pirfenidone was approved for use in 2011 in Europe under the brand name Esbriet®), prednisone, azathioprine, N-acetylcysteine, interferon-γ 1b, bosentan (bosentan is currently being studied in patients with IPF, [*The American Journal of Respiratory and Critical Care Medicine* (2011), 184(1), 92-9]), Nintedanib (BIBF 1120 and Vargatef), QAX576 [*British Journal of Pharmacology* (2011), 163(1), 141-172], and anti-inflammatory agents such as corticosteroids.

In some embodiments, a compound of Formulas (I) and/or (II) can be used to treat idiopathic pulmonary fibrosis/pulmonary fibrosis in combination with any of the following methods: oxygen therapy, pulmonary rehabilitation and surgery.

In some embodiments, a compound of Formulas (I) and/or (II) can be used to treat osteoarthritis in combination with any of the following methods: (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy);

(h) joint replacement (arthroplasty); and (i) in combination with a chronic pain class.

In some embodiments, macular degeneration can be treated with a combination of a compound of Formulas (I) and/or (II) and one or more of the following drugs: Bevacizumab (Avastin®), Ranibizumab (Lucentis®), Pegaptanib (Macugen), Aflibercept (Eylea®), verteporfin (Visudyne®) in combination with photodynamic therapy (PDT) or with any of the following methods: (a) in combination with laser to destroy abnormal blood vessels (photocoagulation); and (b) in combination with increased vitamin intake of antioxidant vitamins and zinc.

In some embodiments, retinitis pigmentosa can be treated with a combination of a compound of Formulas (I) and/or (II) and one or more of the following drugs: UF-021 (Ocuseva™), vitamin A palmitate and pikachurin or with any of the following methods: (a) with the Argus® II retinal implant; and (b) with stem cell and/or gene therapy.

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants and the like, for prolonged and/or timed, pulsed administration at a predetermined rate.

The compounds can be administered either alone or in combination with a conventional pharmaceutical carrier, excipient or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, U K. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formulas (I) and/or (II) is about 0.25 mg/Kg to about 50 mg/Kg in humans.

In some embodiments, the unit dosage of compounds of Formulas (I) and/or (II) is about 0.25 mg/Kg to about 20 mg/Kg in humans.

In some embodiments, the unit dosage of compounds of Formulas (I) and/or (II) is about 0.50 mg/Kg to about 19 mg/Kg in humans.

In some embodiments, the unit dosage of compounds of Formulas (I) and/or (II) is about 0.75 mg/Kg to about 18 mg/Kg in humans.

In some embodiments, the unit dosage of compounds of Formulas (I) and/or (II) is about 1.0 mg/Kg to about 17 mg/Kg in humans.

In some embodiments, the unit dosage of compounds of Formulas (I) and/or (II) is about 1.25 mg/Kg to about 16 mg/Kg in humans.

In some embodiments, the unit dosage of compounds of Formulas (I) and/or (II) is about 1.50 mg/Kg to about 15 mg/Kg in humans.

In some embodiments, the unit dosage of compounds of Formulas (I) and/or (II) is about 1.75 mg/Kg to about 14 mg/Kg in humans.

In some embodiments, the unit dosage of compounds of Formulas (I) and/or (II) is about 2.0 mg/Kg to about 13 mg/Kg in humans.

In some embodiments, the unit dosage of compounds of Formulas (I) and/or (II) is about 3.0 mg/Kg to about 12 mg/Kg in humans.

In some embodiments, the unit dosage of compounds of Formulas (I) and/or (II) is about 4.0 mg/Kg to about 11 mg/Kg in humans.

In some embodiments, the unit dosage of compounds of Formulas (I) and/or (II) is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.01% to 10% in solution are employable, and could be higher if the composition is a solid or suspension, which could be subsequently diluted to the above percentages.

In some embodiments, the composition will comprise about 0.1-10% of the active agent in solution.

In some embodiments, the composition will comprise about 0.1-5% of the active agent in solution.

In some embodiments, the composition will comprise about 0.1-4% of the active agent in solution.

In some embodiments, the composition will comprise about 0.15-3% of the active agent in solution.

In some embodiments, the composition will comprise about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 mg/m$^2$ to about 300 mg/m$^2$.

In some embodiments, these compositions can be administered by intravenous infusion to humans at doses of about 5 mg/m$^2$ to about 200 mg/m$^2$.

In some embodiments, these compositions can be administered by intravenous infusion to humans at doses of about 5 mg/m$^2$ to about 100 mg/m$^2$.

In some embodiments, these compositions can be administered by intravenous infusion to humans at doses of about 10 mg/m$^2$ to about 50 mg/m$^2$.

In some embodiments, these compositions can be administered by intravenous infusion to humans at doses of about 50 mg/m$^2$ to about 200 mg/m$^2$.

In some embodiments, these compositions can be administered by intravenous infusion to humans at doses of about 75 mg/m$^2$ to about 175 mg/m$^2$.

In some embodiments, these compositions can be administered by intravenous infusion to humans at doses of about 100 mg/m$^2$ to about 150 mg/m$^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 μm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formulas (I) and/or (II) disclosed herein intended for respiratory delivery (either systemic or local) can be administered as aqueous formulations, as non-aqueous solutions or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formulas (I) and/or (II) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the invention can be incorporated into a gel formulation (e.g., U.S. Pat. Nos. 4,474,752 and 6,911,211).

In some embodiments, compounds of Formulas (I) and/or (II) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formulas (I) and/or (II) can be delivered from the reservoir of an external or internal implanted pumping system.

Formulations of the invention also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In some embodiments, the compounds of Formulas (I) and/or (II) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of hepatocellular carcinoma, colon cancer, leukemia, lymphoma, sarcoma, ovarian cancer, diabetic retinopathy, pulmonary fibrosis, rheumatoid arthritis, sepsis, ankylosing spondylitis, psoriasis, scleroderma, mycotic and viral infections, bone and cartilage diseases, Alzheimer's disease, lung disease, bone/osteoporotic (wrist, spine, shoulder and hip) fractures, articular cartilage (chondral) defects, degenerative disc disease (or intervertebral disc degeneration), polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease, and Rett syndrome.

Methods of Treatment

The compounds and compositions provided herein can be used as inhibitors and/or modulators of one or more components of the Wnt pathway, which may include one or more Wnt proteins, and thus can be used to treat a variety of disorders and diseases in which aberrant Wnt signaling is implicated, such as cancer and other diseases associated with abnormal angiogenesis, cellular proliferation, and cell cycling. Accordingly, the compounds and compositions provided herein can be used to treat cancer, to reduce or inhibit angiogenesis, to reduce or inhibit cellular proliferation, to correct a genetic disorder, and/or to treat a neurological condition/disorder/disease due to mutations or dysregulation of the Wnt pathway and/or of one or more of Wnt signaling components. Non-limiting examples of diseases which can be treated with the compounds and compositions provided herein include a variety of cancers, diabetic retinopathy, pulmonary fibrosis, rheumatoid arthritis, scleroderma, mycotic and viral infections, bone and cartilage diseases, neurological conditions/diseases such as Alzheimer's disease, amyotrophic lateral sclerosis (ALS), motor neuron disease, multiple sclerosis or autism, lung disease, bone/osteoporotic (wrist, spine, shoulder and hip) fractures, polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

With respect to cancer, the Wnt pathway is known to be constitutively activated in a variety of cancers including, for example, colon cancer, hepatocellular carcinoma, lung cancer, ovarian cancer, prostate cancer, pancreatic cancer and leukemias such as CML, CLL and T-ALL. Accordingly, the compounds and compositions described herein may be used to treat these cancers in which the Wnt pathway is constitutively activated. In certain embodiments, the cancer is chosen from hepatocellular carcinoma, colon cancer, leukemia, lymphoma, sarcoma and ovarian cancer.

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

The compounds and compositions described herein can be used as anti-angiogenesis agents and as agents for modulating and/or inhibiting the activity of protein kinases, thus providing treatments for cancer and other diseases associated with cellular proliferation mediated by protein kinases. For example, the compounds described herein can inhibit the activity of one or more kinases. Accordingly, provided herein is a method of treating cancer or preventing or reducing angiogenesis through kinase inhibition.

In addition, and including treatment of cancer, the compounds and compositions described herein can function as cell-cycle control agents for treating proliferative disorders in a patient. Disorders associated with excessive proliferation include, for example, cancers, scleroderma, immunological disorders involving undesired proliferation of leukocytes, and restenosis and other smooth muscle disorders. Furthermore, such compounds may be used to prevent de-differentiation of post-mitotic tissue and/or cells.

Diseases or disorders associated with uncontrolled or abnormal cellular proliferation include, but are not limited to, the following:

- a variety of cancers, including, but not limited to, carcinoma, hematopoietic tumors of lymphoid lineage, hematopoietic tumors of myeloid lineage, tumors of mesenchymal origin, tumors of the central and peripheral nervous system and other tumors including melanoma, seminoma and Kaposi's sarcoma.
- a disease process which features abnormal cellular proliferation, e.g., benign prostatic hyperplasia, familial adenomatosis polyposis, neurofibromatosis, atherosclerosis, arthritis, glomerulonephritis, restenosis following angioplasty or vascular surgery, inflammatory bowel disease, transplantation rejection, endotoxic shock, and fungal infections. Fibrotic disorders such as skin fibrosis; scleroderma; progressive systemic fibrosis; lung fibrosis; muscle fibrosis; kidney fibrosis; glomerulosclerosis; glomerulonephritis; hypertrophic scar formation; uterine fibrosis; renal fibrosis; cirrhosis of the liver, liver fibrosis; fatty liver disease (FLD); adhesions, such as those occurring in the abdomen, pelvis, spine or tendons; chronic obstructive pulmonary disease; fibrosis following myocardial infarction; pulmonary fibrosis; fibrosis and scarring associated with diffuse/interstitial lung disease; central nervous system fibrosis, such as fibrosis following stroke; fibrosis associated with neuro-degenerative disorders such as Alzheimer's Disease or multiple sclerosis; fibrosis associated with proliferative vitreoretinopathy (PVR); restenosis; endometriosis; ischemic disease and radiation fibrosis.
- defective apoptosis-associated conditions, such as cancers (including but not limited to those types mentioned herein), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus erythematosus, rheumatoid arthritis, sepsis, ankylosing spondylitis, psoriasis, scleroderma, autoimmune mediated glomerulonephritis, inflammatory bowel disease and autoimmune diabetes mellitus), neuro-degenerative disorders (including but not limited to Alzheimer's disease, lung disease, amyotrophic lateral sclerosis, retinitis pigmentosa, Parkinson's disease, AIDS-related dementia, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis), tendinopathies such as tendinitis and tendinosis, aspirin-sensitive rhinosinusitis, cystic fibrosis, multiple sclerosis, kidney diseases and cancer pain.
- genetic diseases due to mutations in Wnt signaling components, such as polyposis coli, bone density and vascular defects in the eye (Osteoporosis-pseudoglioma Syndrome, OPPG), familial exudative vitreoretinopathy, retinal angiogenesis, early coronary disease, tetra-amelia, Müllerian-duct regression and virilization, SERKAL syndrome, type II diabetes, Fuhrmann syndrome, Al-Awadi/Raas-Rothschild/Schinzel phocomelia syndrome, odonto-onycho-dermal dysplasia, obesity, split-hand/foot malformation, caudal duplication, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

The compounds and compositions described herein can be used to treat neurological conditions, disorders and/or diseases caused by dysfunction in the Wnt signaling pathway. Non-limiting examples of neurological conditions/disorders/diseases which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, de Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barre syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina bifida, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease and Zellweger syndrome.

The compounds and compositions may also be useful in the inhibition of the development of invasive cancer, tumor angiogenesis and metastasis.

In some embodiments, the disclosure provides a method for treating a disease or disorder associated with aberrant cellular proliferation by administering to a patient in need of such treatment an effective amount of one or more of the compounds of Formulas (I) and/or (II), in combination (simultaneously or sequentially) with at least one other agent.

In some embodiments, the disclosure provides a method of treating or ameliorating in a patient a disorder or disease selected from the group consisting of: cancer, pulmonary fibrosis, idiopathic pulmonary fibrosis (IPF), degenerative disc disease, bone/osteoporotic fractures, bone or cartilage disease, and osteoarthritis, the method comprising administering to the patient a therapeutically effective amount of a compound according to claim 1, or a pharmaceutically acceptable salt thereof.

In some embodiments, the pharmaceutical composition comprises a therapeutically effective amount of a compound of Formulas (I) and/or (II), or a pharmaceutically acceptable salt thereof, and a pharmaceutically acceptable excipient.

In some embodiments, the method of treats a disorder or disease in which aberrant Wnt signaling is implicated in a patient, the method comprises administering to the patient a therapeutically effective amount of a compound of Formulas (I) and/or (II), or a pharmaceutically acceptable salt thereof.

In some embodiments, the disorder or disease is cancer.

In some embodiments, the disorder or disease is systemic inflammation.

In some embodiments, the disorder or disease is metastatic melanoma.

In some embodiments, the disorder or disease is fatty liver disease.

In some embodiments, the disorder or disease is liver fibrosis.

In some embodiments, the disorder or disease is tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is diabetic retinopathy.

In some embodiments, the disorder or disease is pulmonary fibrosis.

In some embodiments, the disorder or disease is idiopathic pulmonary fibrosis (IPF).

In some embodiments, the disorder or disease is degenerative disc disease.

In some embodiments, the disorder or disease is rheumatoid arthritis.

In some embodiments, the disorder or disease is scleroderma.

In some embodiments, the disorder or disease is a mycotic or viral infection.

In some embodiments, the disorder or disease is a bone or cartilage disease.

In some embodiments, the disorder or disease is Alzheimer's disease.

In some embodiments, the disorder or disease is osteoarthritis.

In some embodiments, the disorder or disease is lung disease

In some embodiments, the disorder or disease is a genetic disease caused by mutations in Wnt signaling components, wherein the genetic disease is selected from: polyposis coli, osteoporosis-pseudoglioma syndrome, familial exudative vitreoretinopathy, retinal angiogenesis, early coronary disease, tetra-amelia syndrome, Müllerian-duct regression and virilization, SERKAL syndrome, diabetes mellitus type 2, Fuhrmann syndrome, Al-Awadi/Raas-Rothschild/Schinzel phocomelia syndrome, odonto-onycho-dermal dysplasia, obesity, split-hand/foot malformation, caudal duplication syndrome, tooth agenesis, Wilms tumor, skeletal dysplasia, focal dermal hypoplasia, autosomal recessive anonychia, neural tube defects, alpha-thalassemia (ATRX) syndrome, fragile X syndrome, ICF syndrome, Angelman syndrome, Prader-Willi syndrome, Beckwith-Wiedemann Syndrome, Norrie disease and Rett syndrome.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, rhabdomyosarcoma, salivary gland cancer, skin cancer—basal and squamous cell, skin cancer—melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma.

In some embodiments, the cancer is colon cancer.

In some embodiments, the cancer is colorectal cancer.

In some embodiments, the cancer is breast cancer.

In some embodiments, the cancer is pancreatic cancer.

In some embodiments, the cancer is chronic myeloid leukemia (CML).

In some embodiments, the cancer is chronic myelomonocytic leukemia.

In some embodiments, the cancer is chronic lymphocytic leukemia (CLL).

In some embodiments, the cancer is acute myeloid leukemia.

In some embodiments, the cancer is acute lymphocytic leukemia.

In some embodiments, the cancer is Hodgkin lymphoma.

In some embodiments, the cancer is lymphoma.

In some embodiments, the cancer is sarcoma.

In some embodiments, the cancer is ovarian cancer.

In some embodiments, the cancer is lung cancer—non-small cell.

In some embodiments, the cancer is lung cancer—small cell.

In some embodiments, the cancer is multiple myeloma.

In some embodiments, the cancer is nasopharyngeal cancer.

In some embodiments, the cancer is neuroblastoma.

In some embodiments, the cancer is osteosarcoma.

In some embodiments, the cancer is penile cancer.

In some embodiments, the cancer is pituitary tumors.

In some embodiments, the cancer is prostate cancer.

In some embodiments, the cancer is retinoblastoma.

In some embodiments, the cancer is rhabdomyosarcoma.

In some embodiments, the cancer is salivary gland cancer.

In some embodiments, the cancer is skin cancer—basal and squamous cell.

In some embodiments, the cancer is skin cancer—melanoma.

In some embodiments, the cancer is small intestine cancer.

In some embodiments, the cancer is stomach (gastric) cancers.

In some embodiments, the cancer is testicular cancer.

In some embodiments, the cancer is thymus cancer.

In some embodiments, the cancer is thyroid cancer.

In some embodiments, the cancer is uterine sarcoma.

In some embodiments, the cancer is vaginal cancer.

In some embodiments, the cancer is vulvar cancer.

In some embodiments, the cancer is Wilms tumor.

In some embodiments, the cancer is laryngeal or hypopharyngeal cancer.

In some embodiments, the cancer is kidney cancer.

In some embodiments, the cancer is Kaposi sarcoma.

In some embodiments, the cancer is gestational trophoblastic disease.

In some embodiments, the cancer is gastrointestinal stromal tumor.

In some embodiments, the cancer is gastrointestinal carcinoid tumor.

In some embodiments, the cancer is gallbladder cancer.

In some embodiments, the cancer is eye cancer (melanoma and lymphoma).

In some embodiments, the cancer is Ewing tumor.

In some embodiments, the cancer is esophagus cancer.

In some embodiments, the cancer is endometrial cancer.

In some embodiments, the cancer is colorectal cancer.

In some embodiments, the cancer is cervical cancer.

In some embodiments, the cancer is brain or spinal cord tumor.

In some embodiments, the cancer is bone metastasis.

In some embodiments, the cancer is bone cancer.

In some embodiments, the cancer is bladder cancer.

In some embodiments, the cancer is bile duct cancer.

In some embodiments, the cancer is anal cancer.

In some embodiments, the cancer is adrenal cortical cancer.

In some embodiments, the disorder or disease is a neurological condition, disorder or disease, wherein the neurological condition/disorder/disease is selected from: Alzheimer's disease, frontotemporal dementias, dementia with lewy bodies, prion diseases, Parkinson's disease, Huntington's disease, progressive supranuclear palsy, corticobasal degeneration, multiple system atrophy, amyotrophic lateral sclerosis (ALS), inclusion body myositis, autism, degenerative myopathies, diabetic neuropathy, other metabolic neuropathies, endocrine neuropathies, orthostatic hypotension, multiple sclerosis and Charcot-Marie-Tooth disease.

In some embodiments, the compound of Formulas (I) and/or (II) inhibits one or more proteins in the Wnt pathway.

In some embodiments, the compound of Formulas (I) and/or (II) inhibits signaling induced by one or more Wnt proteins.

In some embodiments, the Wnt proteins are chosen from: WNT1, WNT2, WNT2B, WNT3, WNT3A, WNT4.

WNT5A, WNT5B, WNT6, WNT7A, WNT7B, WNT8A, WNT8B, WNT9A, WNT9B, WNT10A, WNT10B, WNT11, and WNT16.

In some embodiments, the compound of Formulas (I) and/or (II) inhibits a kinase activity.

In some embodiments, the method treats a disease or disorder mediated by the Wnt pathway in a patient, the method comprises administering to the patient a therapeutically effective amount of a compound (or compounds) of Formulas (I) and/or (II), or a pharmaceutically acceptable salt thereof.

In some embodiments, the compound of Formulas (I) and/or (II) inhibits one or more Wnt proteins.

In some embodiments, the method treats a disease or disorder mediated by kinase activity in a patient, the method comprises administering to the patient a therapeutically effective amount of a compound (or compounds) of Formulas (I) and/or (II), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formulas (I) and/or (II), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formulas (I) and/or (II), or a pharmaceutically acceptable salt thereof.

In some embodiments, the method prevents or reduces angiogenesis in a patient; the method comprises administering to the patient a therapeutically effective amount of a compound (or compounds) of Formulas (I) and/or (II), or a pharmaceutically acceptable salt thereof.

In some embodiments, the method prevents or reduces abnormal cellular proliferation in a patient; the method comprises administering to the patient a therapeutically effective amount of a compound (or compounds) of Formulas (I) and/or (II), or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Moreover, the compounds and compositions, for example, as inhibitors of the cyclin-dependent kinases (CDKs), can modulate the level of cellular RNA and DNA synthesis and therefore are expected to be useful in the treatment of viral infections such as HIV, human papilloma virus, herpes virus, Epstein-Barr virus, adenovirus, Sindbis virus, pox virus and the like.

Compounds and compositions described herein can inhibit the kinase activity of, for example, CDK/cyclin complexes, such as those active in the $G_0$. or $G_{-1}$ stage of the cell cycle, e.g., CDK2, CDK4, and/or CDK6 complexes.

Evaluation of Biological Activity

The biological activity of the compounds described herein can be tested using any suitable assay known to those of skill in the art, see, e.g., WO 2001/053268 and WO 2005/009997. For example, the activity of a compound may be tested using one or more of the test methods outlined below.

In one example, tumor cells may be screened for Wnt independent growth. In such a method, tumor cells of interest are contacted with a compound (i.e. inhibitor) of interest, and the proliferation of the cells, e.g. by uptake of tritiated thymidine, is monitored. In some embodiments, tumor cells may be isolated from a candidate patient who has been screened for the presence of a cancer that is associated with a mutation in the Wnt signaling pathway. Candidate cancers include, without limitation, those listed above.

In another example, one may utilize in vitro assays for Wnt biological activity, e.g. stabilization of β-catenin and promoting growth of stem cells. Assays for biological activity of Wnt include stabilization of β-catenin, which can be measured, for example, by serial dilutions of a candidate inhibitor composition. An exemplary assay for Wnt biological activity contacts a candidate inhibitor with cells containing constitutively active Wnt/β-catenin signaling. The cells are cultured for a period of time sufficient to stabilize β-catenin, usually at least about 1 hour, and lysed. The cell lysate is resolved by SDS PAGE, then transferred to nitrocellulose and probed with antibodies specific for β-catenin.

In a further example, the activity of a candidate compound can be measured in a Xenopus secondary axis bioassay (Leyns, L. et al. *Cell* (1997), 88(6), 747-756).

To further illustrate this invention, the following examples are included. The examples should not, of course, be construed as specifically limiting the invention. Variations of these examples within the scope of the claims are within the purview of one skilled in the art and are considered to fall within the scope of the invention as described, and claimed herein. The reader will recognize that the skilled artisan, armed with the present disclosure, and skill in the art is able to prepare and use the invention without exhaustive examples.

EXAMPLES

Compound Preparation

The starting materials used in preparing the compounds of the invention are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* $7^{th}$ Ed., John Wiley & Sons (2013), Carey and Sundberg, *Advanced Organic Chemistry* $5^{th}$ Ed., Springer (2007), *Comprehensive Organic Transformations: A Guide to Functional Group Transformations*, $2^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene and P. Wuts *Protective Groups in Organic Synthesis,* 4th Ed., John Wiley & Sons (2007), incorporated herein by reference in its entirety.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

($^1$H) nuclear magnetic resonance spectra (NMR) were measured in the indicated solvents on a Bruker NMR spectrometer (Avance™ DRX300, 300 MHz for $^1$H or Avance™ DRX500, 500 MHz for $^1$H) or Varian NMR spectrometer (Mercury 400BB, 400 MHz for $^1$H). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:
brine=saturated aqueous sodium chloride
$CDCl_3$=deuterated chloroform
DCE=dichloroethane
DCM=dichloromethane
DEAD=diethyl azodicarboxylate
DIPEA=N,N-diisopropylethylamine
DMA=dimethylacetamide
DMAP=4-dimethylaminopyridine
DMF=N,N-dimethylformamide
DMSO-$d_6$=deuterated dimethylsulfoxide
ESIMS=electron spray mass spectrometry
EtOAc=ethyl acetate
HATU=1-[Bis(dimethylamino)methylene]-1H-1,2,3-triazolo[4,5-b]pyridinium 3-oxid hexafluorophosphate
HCl=hydrochloric acid
HOAc=acetic acid
ISCO=Teledyne ISCO, Inc brand CombiFlash® Rf 200
KOAc=potassium acetate
LC/MS=Liquid chromatography-mass spectrometry
MeCN=acetonitrile
MeOH=methanol
$MgSO_4$=magnesium sulfate
MW=microwave irradiation
$NaBH_3CN$=sodium cyanoborohydride
$NaHCO_3$=sodium bicarbonate
$Na(OAc)_3BH$=Sodium triacetoxyborohydride
$Na_2S_2O_3$=sodium thiosulfate
NMR=nuclear magnetic resonance
ON=overnight
$Pd(dppf)Cl_2$=1,1'-bis(diphenylphosphino)ferrocene-palladium(II)dichloride
$Pd(PPh_3)_4$=tetrakis(triphenylphosphine)palladium(0)
r.t.=room temperature
SPhos Pd G4=Methanesulfonato(2-dicyclohexylphosphino-3,6-dimethoxy-2',4',6'-tri-i-propyl-1,1'-biphenyl)(2'-methylamino-1,1'-biphenyl-2-yl)palladium(II)
TBAF=Tetra-n-butylammonium fluoride,
TEA=triethylamine
TFA=trifluoroacetic acid
THF=tetrahydrofuran
TLC=thin layer chromatography The following example schemes are provided for the guidance of the reader, and collectively represent an example methods for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only, and should not be construed as or confused with same numberings in other sections of the application. Unless otherwise indicated, all variables are as defined above.

General Procedures

Compounds of Formula I of the present disclosure can be prepared as depicted in Scheme 1.

Scheme 1

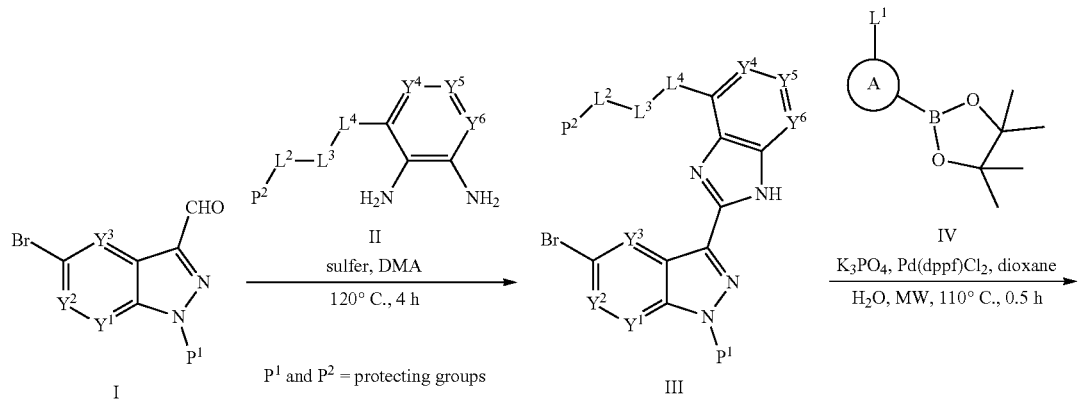

$P^1$ and $P^2$ = protecting groups

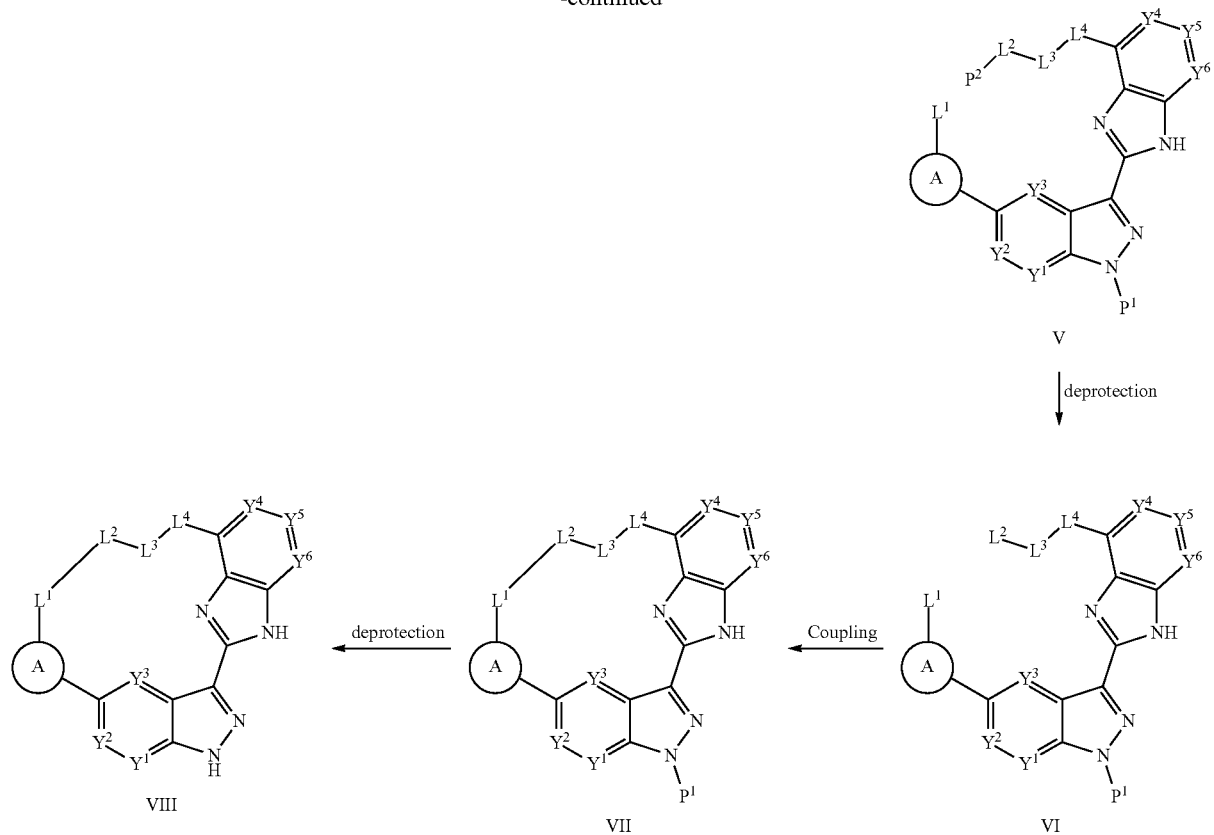

Scheme 1 describes a method for preparation of aza/indazole-aza/benzimidazole derivatives (VIII) by first cyclizing the diamine intermediate (II) with the aza/indazole aldehyde intermediate (I) in the presence of sulfur to produce the bromo aza/indazole-aza/benzimidazole (III). The bromo intermediate (III) is then coupled with the borate ester (IV) using Suzuki Coupling to give aza/indazole-aza/benzimidazole analogs (V). The protecting group on the linker of (V) is removed followed by couple of the $L^2$ group with the $L^1$ group on Ring A to produce macrocycle (VII). Macrocycle (VII) is then deprotected to yield the desired aza/indazole-aza/benzimidazole derivatives (VIII).

Alternatively, compounds of Formula I of the present disclosure can be prepared as depicted in Scheme 2.

Scheme 2

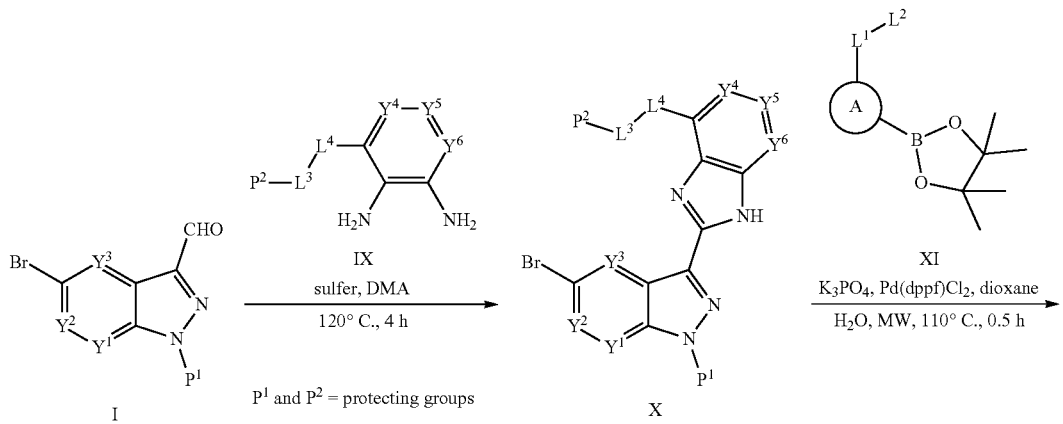

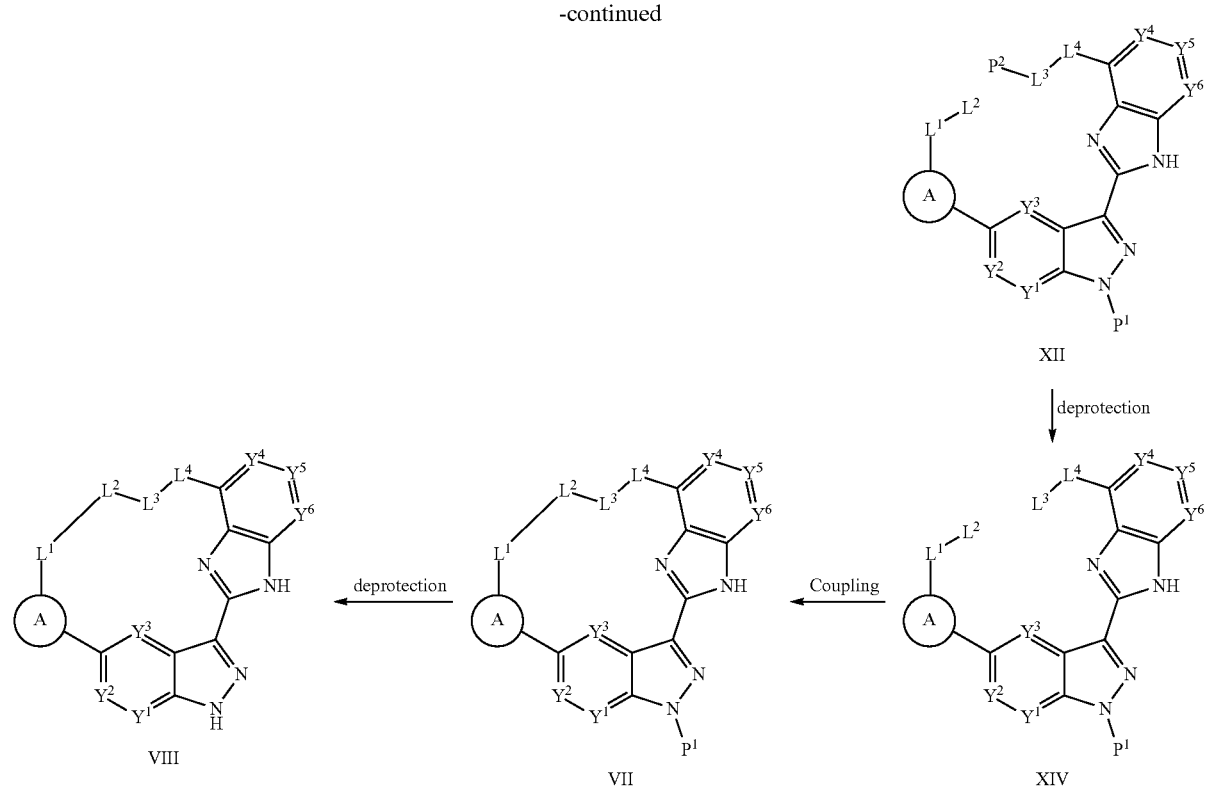

Scheme 2 describes an alternative method for preparation of aza/indazole-aza/benzimidazole derivatives (VIII) by first cyclizing the diamine intermediate (IX) with the aza/indazole aldehyde intermediate (I) in the presence of sulfur to produce the bromo aza/indazole-aza/benzimidazole (X). The bromo intermediate (X) is then coupled with the borate ester (XI) using Suzuki Coupling to give aza/indazole-aza/benz-imidazole analogs (XII). The protecting group on the linker of (XII) is removed followed by couple of the $L^3$ group with the $L^2$ group on Ring A to produce macrocycle (VII). Macrocycle (VII) is then deprotected to yield the desired aza/indazole-aza/benzimidazole derivatives (VIII).

Compounds of Formula II of the present disclosure can be prepared as depicted in Scheme 3.

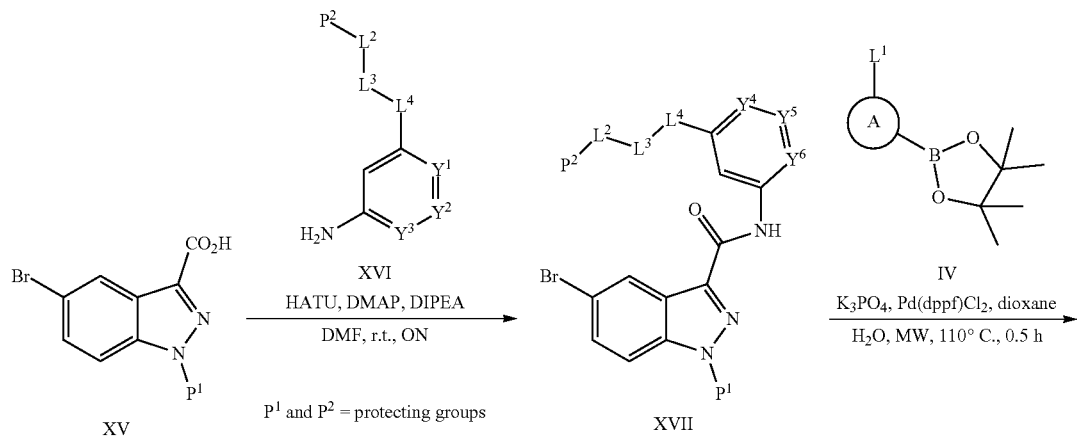

Scheme 3

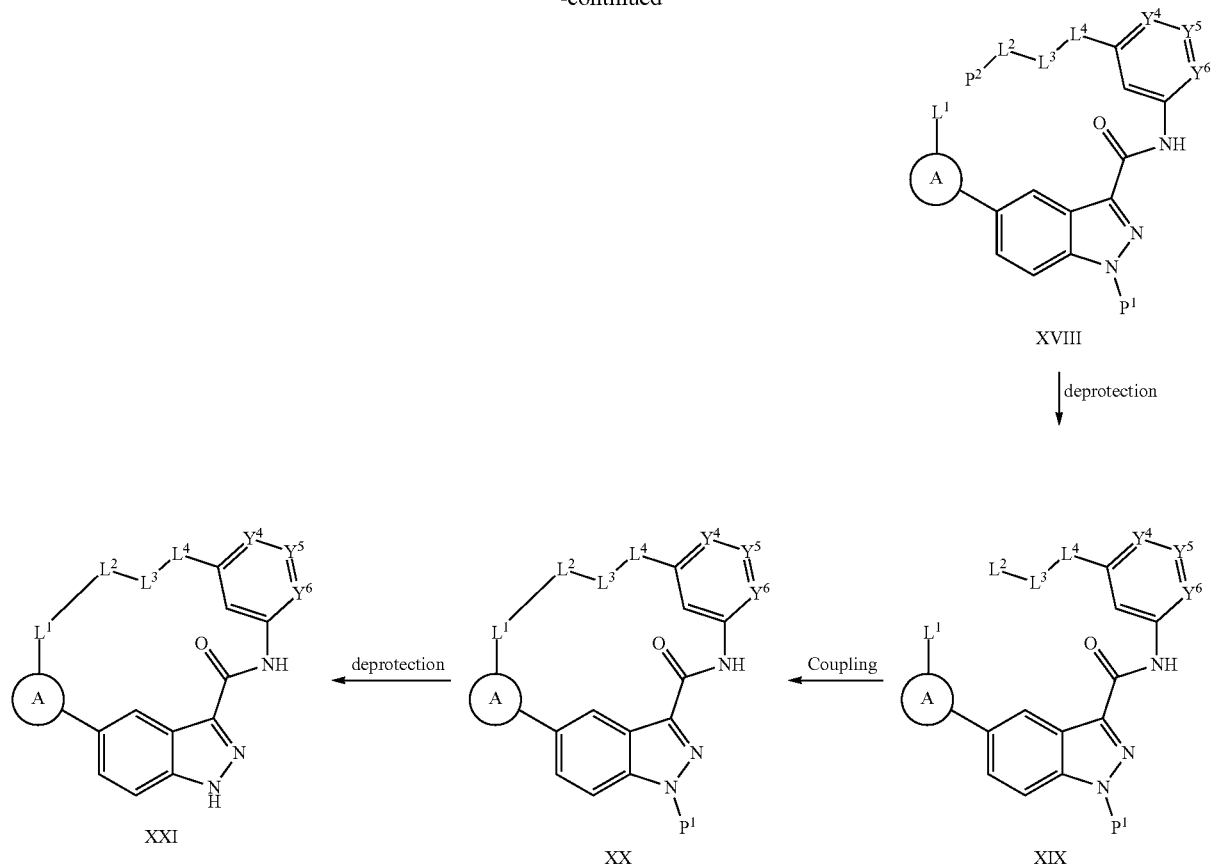

XVIII

Scheme 3 describes a method for preparation of indazole carboxamides derivatives (XXI) by first coupling the amine intermediate (XVI) with the indazole acid intermediate (XV) to produce the bromo indazole carboxamides (XVII). The bromo intermediate (XVII) is then coupled with the borate ester (IV) using Suzuki Coupling to give indazole carboxamides analogs (XVIII). The protecting group on the linker of (XVIII) is removed followed by couple of the $L^2$ group with the $L^1$ group on Ring A to produce macrocycle (XX). Macrocycle (XX) is then deprotected to yield the desired indazole carboxamides derivatives (XXI).

Alternatively, compounds of Formula II of the present disclosure can be prepared as depicted in Scheme 4.

Scheme 4

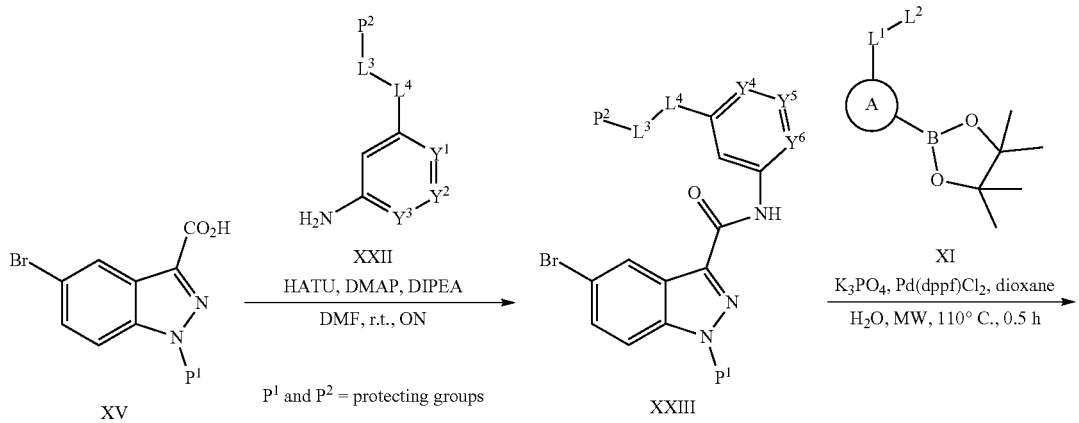

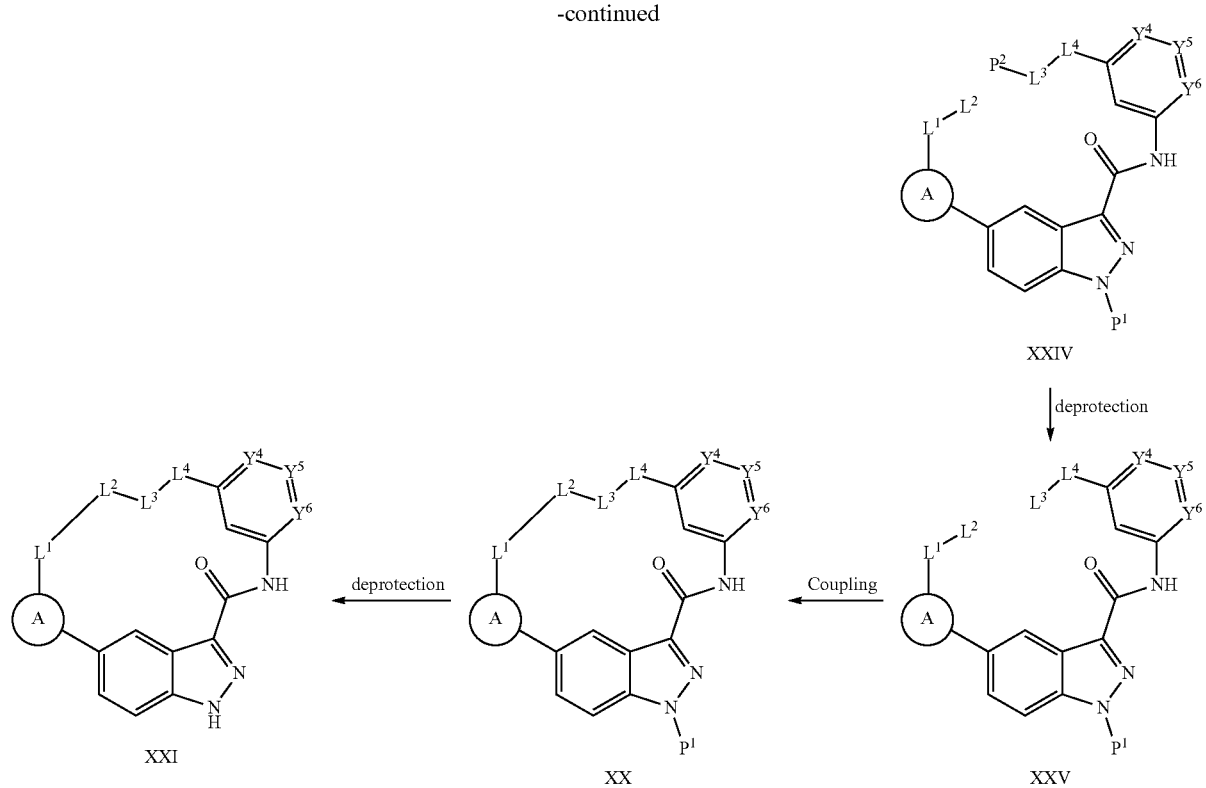

Scheme 4 describes an alternative method for preparation of indazole carboxamides derivatives (XXI) by first coupling the amine intermediate (XXII) with the indazole acid intermediate (XV) to produce the bromo indazole carboxamides (XXIII). The bromo intermediate (XXIII) is then coupled with the borate ester (IV) using Suzuki Coupling to give indazole carboxamides analogs (XXIV). The protecting group on the linker of (XXIV) is removed followed by couple of the $L^3$ group with the $L^2$ group on Ring A to produce macrocycle (XX). Macrocycle (XX) is then deprotected to yield the desired indazole carboxamides derivatives (XXI).

Illustrative Compound Examples

Preparation of intermediate 5-bromo-1-trityl-3a,7a-dihydro-1H-indazole-3-carbaldehyde (XXVIII) is depicted below in Scheme 5.

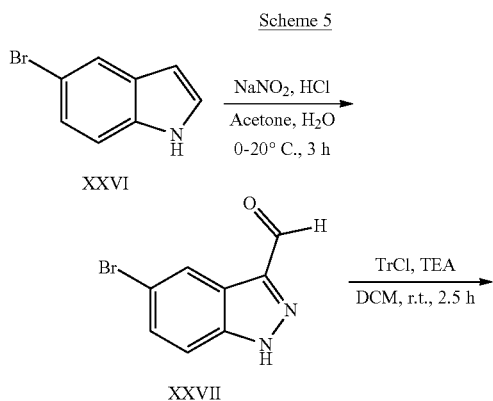

-continued

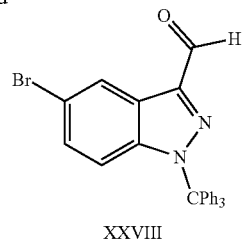

Step 1

A solution of NaNO$_2$ (110.4 g, 1.6 mol, 8 eq) in water (200 mL) was added dropwise to a solution of 5-bromoindole (XXVI) (39.2 g, 0.2 mol, 1 eq) in acetone (1000 mL) stirred at $-10 \rightarrow 0°$ C., while adding NaNO$_2$ the solution temperature was maintained below 20° C. An aqueous 2N HCl solution (480 mL) was added slowly to the solution with vigorously stirring while keeping the internal temperature between 0 and 20° C. The solution was further stirred at 20° C. for 3 h after the addition. The solution was concentrated under reduced pressure to remove acetone while keeping the temperature below 35° C. The solid was collected by filtration and transferred to a flask. Cold ($-10°$ C.) DCM (200 mL) was added and stirred for 30 min at $-5°$ C., the solids were filtered and dried under vacuum at 40° C. to get 5-bromo-1H-indazole-3-carbaldehyde (XXVII) (34.0 g, 151 mmol, 76% yield) as a brown solid. ESIMS found for C$_8$H$_5$BrN$_2$O m/z 225 (M+H).

Step 2

A solution of 5-bromo-1H-indole (XXVII) (10.0 g, 44.4 mmol) in DCM (100 mL) was added TEA (4 mL, 28.9 mmol). The solution was cooled to 0° C. before slowly added triphenylmethyl chloride (19.8 g, 71.1 mmol) in DCM (100 mL) while maintaining the temperature <20° C. The reaction was then stirred at room temperature for 2.5 h. Water was added and the organic layer was separated. The aqueous phase was washed 3×DCM. The combined organic layers were washed with brine, dried over MgSO$_4$, and concentrated. The residue was titrated with EtOAc and the solid was filtered to give 5-bromo-1-trityl-3a,7a-dihydro-1H-indazole-3-carbaldehyde (XXVIII) (6.26 g, 13.4 mmol, 30.0% yield) as a light purple solid. $^1$H NMR (400 MHz, DMSO-d$_6$) δ ppm 6.48 (d, J=7.6 Hz, 1H), 7.15 (dd, J=1.2 Hz, J=6.4 Hz, 6H), 7.32 (d, J=7.6 Hz, 1H), 7.33-7.40 (m, 9H), 8.31 (d, J=1.6 Hz, 1H), 10.06 (s, 1H); ESIMS found for C$_{27}$H$_{21}$BrN$_2$O m/z 471.1 ($^{81}$BrM+H).

Synthesis of intermediate 5-bromo-1-trityl-1H-pyrazolo[3,4-b]pyridine-3-carbaldehyde (XXXVIII) is depicted below in Scheme 6.

27.7 mol) dissolved in water (33 L). The solution was cooled to 0° C. before adding TEMPO (1.7 Kg, 10.9 mol) and then stirred for 50 min. In a second container, water (980 L) was added followed by KHCO$_3$ (268 Kg, 2677 mol) and 10% aqueous NaClO (233 L, 313 mol). This aqueous mixture was then added dropwise to the TEMPO mixture. This combined mixture was stirred at 0° C. for 5 hours. To this mixture was added dropwise Na$_2$S$_2$O$_3$.7H$_2$O (22.5 Kg, 90 mol) in water (107 L) with stirring for 50 min at 0° C. The mixture was allowed to warm to room temperature and the organic phase was separated. The aqueous phase was extracted 2×DCM (353 L) by adding DCM, stirring for 50 min, allowing to stand for 50 min, separating the layers and then repeating. The combined organic layers were washed with aqueous 25% NaCl (274 L) and concentrated under vacuum to give

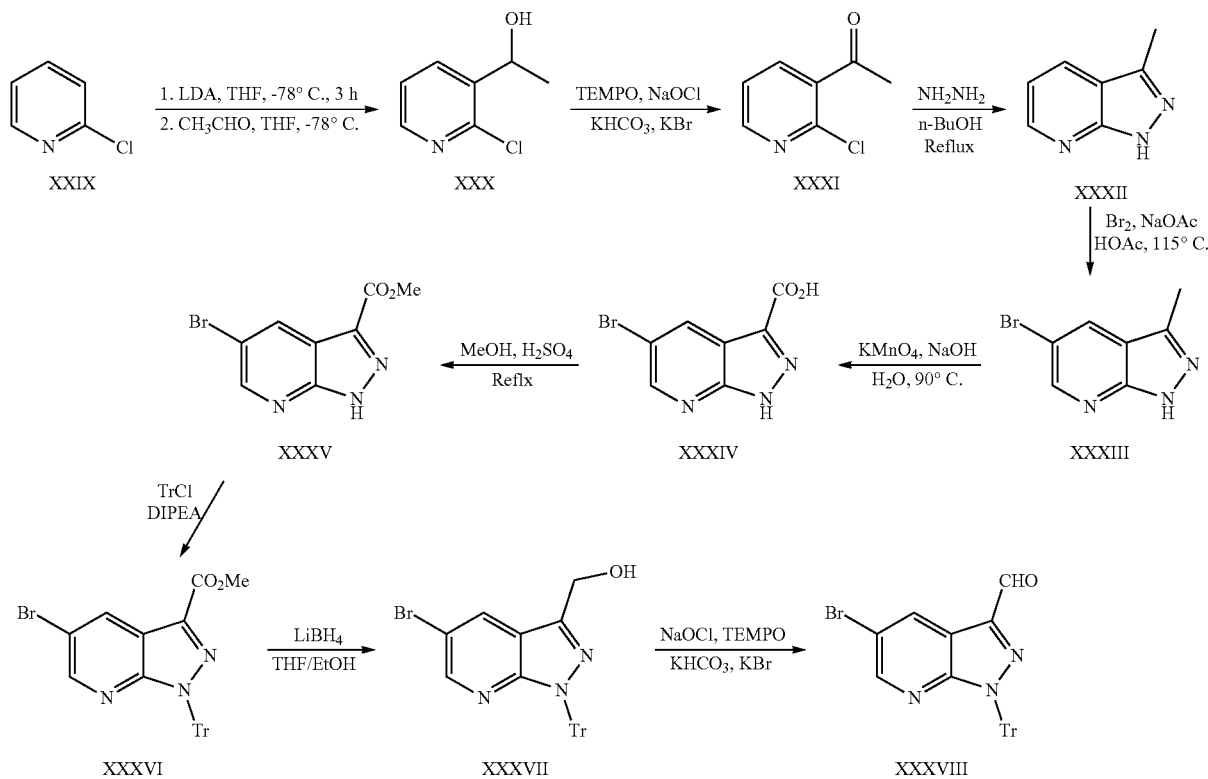

Scheme 6

Step 1-2

To a solution of 2-chloropyridine (XXIX) (31.0 kg, 273 mol) in dry THF (275 L) cooled to −78° C. under nitrogen was added LDA (113 L, 1220 mol) dropwise while maintaining the temperature at −78° C. and stirred for 5 hours. Acetaldehyde (16 L, 463 mol) was then added and the reaction was stirred at −78° C. for another 5 hours before warming to 0° C. and adding water (310 L) to quench the reaction. The solution was stirred for 50 min and then warmed to room temperature. The solution was extracted 3× EtOAc (279 L) by adding EtOAc, stirring for 50 min, allowing to stand for 50 min, separating the layers and then repeating twice. The combined EtOAc was concentrated under vacuum to a volume of 300-500 L. To the crude 1-(2-chloropyridin-3-yl)ethanol (XXX) was added DCM (705 L) followed by an aqueous solution of KBr (3.3 Kg, crude 1-(2-chloropyridin-3-yl)ethanone (XXXI) which was used for the next step without additional purification.

Step 3

To a solution of the above crude 1-(2-chloropyridin-3-yl)ethanone (XXXI) in n-BuOH (512 L) was added 85% hydrazine hydrate (78 L, 1360 mol). The reaction was heated at refluxed (−120° C.) for 48 hours. The reaction was cooled and evaporated under vacuum. The crude material was taken up in DCM (834 L) and washed with 2× aqueous 25% NaCl (214 L) by adding aqueous 25% NaCl, stirring for 50 min, allowing to stand for 50 min, separating the layers and then repeating. The organic layer was evaporated to produce 3-methyl-1H-pyrazolo[3,4-b]pyridine (XXXII) as a solid (13.2 Kg, 99 mol, 94.1% purity, 36.3% assay yield for 3 steps). $^1$H NMR (DMSO-d$_6$, 400 MHz) δ ppm 2.50 (s, 3H), 7.13 (dd, J=4.4 Hz, J=8 Hz, 1H), 8.19 (dd, J=1.2 Hz, J=8 Hz, 1H), 8.47 (dd, J=1.6 Hz, J=4.8 Hz, 1H), 13.18 (brs, 1H); ESIMS found $C_7H_7N_3$ m/z 133.8 (M+H).

Step 4

To a solution of 3-methyl-1H-pyrazolo[3,4-b]pyridine (XXXII) (12.7 Kg, 95.4 mol) in HOAc (57 L) was added NaOAc (20.4 Kg, 248 mol), water (13.3 L), and $Br_2$ (40 L, 780 mol). The reaction was stirred at room temperature for 5 hours and then at 115° C. for 6 hours. The reaction was cooled to room temperature and diluted with DCM (686 L). To this solution was added water (508 L) and cooled to 0° C. followed by dropwise addition of aqueous 30% NaOH while maintaining the temperature <20° C. under pH=9. The mixture was filtered through diatomaceous earth (14 Kg) followed by washing the diatomaceous earth with 3×DCM (50 L). The organic layer was separated, washed with aqueous 25% NaCl (200 L) and concentrated under vacuum to a volume of 70 L. The product was crystallized by charging the solution with 3× n-heptane (88 L) while concentrating the volume to 70 L after each addition of n-heptane. The solid was filtered and washed 3× n-heptane (22 L). The solid was dried under vacuum at 45° C. to yield 5-bromo-3-methyl-1H-pyrazolo[3,4-b]pyridine (XXXIII) (9.8 Kg, 46.2 mol, 92.6% purity, 48.4% assay yield). $^1$H NMR (DMSO-$d_6$, 400 MHz) δ ppm 2.48 (s, 3H), 8.50-8.55 (m, 2H), 13.42 (brs, 1H); ESIMS found $C_7H_6BrN_3$ m/z 213.7 (M+H).

Step 5

To a solution of NaOH (27 Kg, 675 mol) in water (617 L) was added 5-bromo-3-methyl-1H-pyrazolo[3,4-b]pyridine (XXXIII) (9.8 Kg, 46.2 mol). The solution was heated at 90° C. for 3 hours under nitrogen before adding a solution of $KMnO_4$ (53.6 Kg, 339 mol) in water (870 L) slowly over 2 hours. The reaction was heated at 95° C. for 5 hours under nitrogen. The solution was cooled to 75° C. and filtered through diatomaceous earth (11 Kg) followed by washing the diatomaceous earth with water (150 L) heated at 75° C. The solution was cooled to 0° C. under nitrogen before the pH was adjusted to 1 with aqueous 35% HCl (~75 L). The solution was warmed to room temperature before adding n-BuOH (473 L) which was stirred for 25 min and then the organic layer was separated. n-BuOH (473 L) was again added to the aqueous layer, stirred for 25 min and separated. The combined organic phases were concentrated under vacuum to a volume of ~54 L. The n-BuOH was removed by adding to the solution 9× n-heptane (78 L) dropwise over 1 hour and then concentrating the volume to ~54 L after each addition of n-heptane. The solid was filtered and washed 3× n-heptane (17 L). The solid was dried under vacuum at 45° C. to give 5-bromo-1H-pyrazolo[3,4-b]pyridine-3-carboxylic acid (XXXIV) (3.2 Kg, 13.2 mol, 64.4% purity, 29.0% assay yield). $^1$H NMR (DMSO-$d_6$, 400 MHz) δ ppm 8.57 (d, J=2.4 Hz, 1H), 8.71 (d, J=2 Hz, 1H), 13.45 (brs, 1H), 14.65 (s, 1H); ESIMS found $C_7H_4BrN_3O_2$ m/z 243.8 (M+H).

Step 6

To a solution of 5-bromo-1H-pyrazolo[3,4-b]pyridine-3-carboxylic acid (XXXIV) (1.6 Kg, 6.6 mol) in anhydrous MeOH (32 L) was added $H_2SO_4$ (160 mL). The reaction was slowly heated to 70° C. and stirred for 20 hours. The solution was concentrated under vacuum to a volume of 1.6 L. The residue was partitioned between DCM (120 L) and aqueous 10% $NaHCO_3$ (32 L). The organic phase was separated and washed with aqueous 25% NaCl (32 L), dried over $Na_2SO_4$ and concentrated to a volume of 4.8 L. The product was crystallized by charging the solution with 3× n-heptane (8 L) while concentrating the volume to 4.8 L after each addition of n-heptane. The solid was filtered and dried under vacuum at 50° C. to produce methyl 5-bromo-1H-pyrazolo[3,4-b]pyridine-3-carboxylate (XXXV) (1.53 Kg, 6.0 mol, 80.6% purity, 90.4% assay yield). $^1$H NMR (DMSO-$d_6$, 400 MHz) δ ppm 3.95 (s, 3H), 8.62 (d, J=2 Hz, 1H), 8.73 (d, J=2.4 Hz, 1H), 14.78 (brs, 1H); ESIMS found $C_8H_6BrN_3O_2$ m/z 256.0 (M+H).

Step 7

To a solution of methyl 5-bromo-1H-pyrazolo[3,4-b]pyridine-3-carboxylate (XXXV) (2.92 Kg, 11.4 mol) in anhydrous DCM (88 L) was added TEA (2.38 L, 17.1 mol). The solution was cooled to 0° C. before adding dropwise a solution of TrCl (4.0 Kg, 14.3 mol) in anhydrous DCM (51 L). The solution was warmed to room temperature and stirred for 20 hours. The reaction was then washed once with water (29 L), once with aqueous 25% NaCl (29 L), dried over $Na_2SO_4$ and concentrated to a volume of 3.0 L to give methyl 5-bromo-1-trityl-1H-pyrazolo[3,4-b]pyridine-3-carboxylate (XXXVI) (5.69 Kg, 11.4 mol, 77.3% purity, 99.5% assay yield). $^1$H NMR (DMSO-$d_6$, 400 MHz) δ ppm 3.91 (s, 3H), 7.19 (d, J=8.4 Hz, 5H), 7.21-7.32 (m, 10H), 8.45 (d, J=2.4 Hz, 1H), 8.61 (d, J=2 Hz, 1H); ESIMS found $C_{27}H_{20}BrN_3O_2$ m/z 520.0 (M+Na).

Step 8

To a solution of methyl 5-bromo-1-trityl-1H-pyrazolo[3,4-b]pyridine-3-carboxylate (XXXVI) (4.16 Kg, 8.3 mol) in anhydrous THF (62 L) cooled to 10° C. was added anhydrous EtOH (0.97 L, 16.6 mol) and $LiBH_4$ (271 g, 12.5 mol). The reaction was warmed to room temperature and stirred for 24 hours. The solution was concentrated under vacuum to a volume of 4 L then taken up in DCM (80 L). The pH was then adjusted to 8.0 by dropwise addition of aqueous 0.4N HCl (~280 L). The organic layer was separated and washed with aqueous 25% NaCl (28 L) and then concentrated under vacuum to a volume of 4 L to produce (5-bromo-1-trityl-1H-pyrazolo[3,4-b]pyridin-3-yl)methanol (XXXVII) (3.9 Kg, 8.3 mol, 82.3% purity, 100% assay yield). $^1$H NMR (DMSO-$d_6$, 400 MHz) δ ppm 4.70 (d, J=6 Hz, 2H), 5.49 (t, J=6 Hz, 1H), 7.19 (d, J=7.2 Hz, 5H), 7.20-7.35 (m, 10H), 8.31 (d, J=2.4 Hz, 1H), 8.51 (d, J=2.4 Hz, 1H); ESIMS found $C_{26}H_{20}BrN_3O$ m/z 492.0 (M+Na).

Step 9

To a solution of (5-bromo-1-trityl-1H-pyrazolo[3,4-b]pyridin-3-yl)methanol (XXXVII) (4.05 Kg, 8.6 mol) in DCM (97 L) was added a solution of KBr (205 g, 1.72 mol) in water (4 L). The solution was cooled to 0° C. before adding TEMPO (107.5 g, 688 mmol) and stirring for 30 min. To this solution was added a solution of $KHCO_3$ (10.8 Kg, 107.4 mol) and aqueous 7% NaClO (13.4 L) in water (40 L). The reaction was stirred at 0° C. for 18 hours. A solution of $Na_2S_2O_3 \cdot 5H_2O$ (1.4 Kg, 5.7 mol) in water (9.1 L) was added dropwise to the reaction at 0° C. and stirred for 30 min. The aqueous layer was then separated and washed with DCM (48 L). The combined organic phases were washed with aqueous 25% NaCl (48 L), dried over $Na_2SO_4$, filtered and concentrated under vacuum. The residue was co-evaporated with 3× MeOH (20 L) and the solid was washed with 2× n-heptane (8 L). The solid was dried under vacuum at 45° C. to give 5-bromo-1-trityl-1H-pyrazolo[3,4-b]pyridine-3-carbaldehyde (XXXVIII) (3.25 Kg, 6.94 mol, 92.3% purity, 80.6% assay yield). $^1$H NMR (CDCl$_3$, 400 MHz) δ ppm 7.19 (d, J=6 Hz, 5H), 7.22-7.34 (m, 10H), 8.28 (d, J=2.4 Hz, 1H), 8.70 (d, J=2.4 Hz, 1H), 10.07 (s, 1H); ESIMS found $C_{26}H_{18}BrN_3O$ m/z 490.0 (M+Na).

Preparation of intermediate 5-bromo-1-(tetrahydro-2H-pyran-2-yl)-1H-pyrazolo[3,4-c]pyridine-3-carbaldehyde (XLV) is depicted below in Scheme 7.

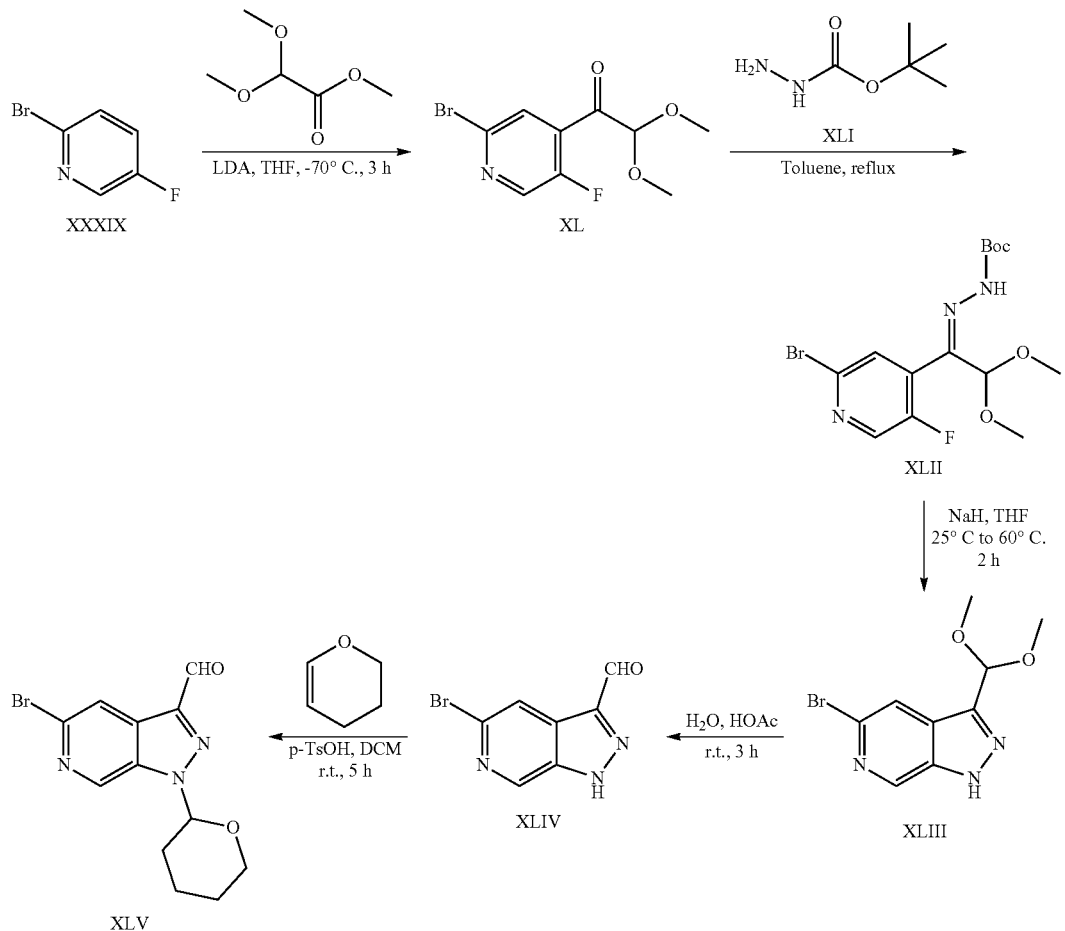

Scheme 7

Step 1

To a solution of i-Pr₂NH (94.9 g, 938 mmol, 132 mL) in THF (0.5 L) was added n-BuLi (2.5 M, 375 mL) drop-wise at −78° C. under N₂. The mixture was stirred at 25° C. for 30 min. Then the mixture above was added drop-wise to a solution of 2-bromo-5-fluoropyridine (XXXIX) (150 g, 852 mmol) in THF (500 mL) at −78° C. under N₂. The reaction mixture was stirred at −78° C. for 1 h. To the mixture was added methyl 2, 2-dimethoxyacetate (126 g, 938 mmol, 115 mL) in THF (0.5 L) drop-wise at −78° C., and then stirred at −78° C. for another 2 h. The mixture was poured into water (1000 mL), extracted with EtOAc (800 mL×3). The combined organic phases were washed with brine (1000 mL×2), dried over Na₂SO₄, concentrated in vacuum to produce crude 1-(5-bromo-2-1-(2-bromo-5-fluoropyridin-4-yl)-2,2-dimethoxyethan-1-one (XL) (94.1% yield) as a yellow oil. The crude was used on next step without further purification. ¹H NMR (400 MHz, CDCl₃) δ ppm 3.47 (s, 6H), 5.14 (s, 1H), 7.80 (d, J=4.52 Hz, 1H), 8.38 (br. s, 1H); ESIMS found for C₉H₉BrFNO₃ m/z 278.0 (⁷⁹BrM+H).

Step 2

A mixture of 1-(2-bromo-5-fluoropyridin-4-yl)-2,2-dimethoxyethan-1-one (XL) (223 g, 802 mmol, crude) and tert-butyl N-aminocarbamate (XLI) (95.4 g, 722 mmol) in toluene (2.00 L) was stirred with a Dean-stark at 100° C. for 5 h. The mixture was concentrated in vacuum to give crude tert-butyl (Z)-2-(1-(2-bromo-5-fluoropyridin-4-yl)-2,2-dimethoxyethylidene)hydrazine-1-carboxylate (XLII) (325 g). The crude product was used on next step directly. ¹H NMR (300 MHz, CDCl₃) δ ppm 3.37-3.56 (m, 6H), 5.84 (s, 1H), 8.08 (s, 1H), 8.93 (s, 1H), 11.22-11.77 (m, 1H); ESIMS found for C₁₄H₁₉BrFN₃O₄ m/z 392.0 (⁷⁹BrM+H).

Step 3

A solution of crude tert-butyl (Z)-2-(1-(2-bromo-5-fluoropyridin-4-yl)-2,2-dimethoxyethylidene)hydrazine-1-carboxylate (XLII) (325 g, 829 mmol) in THF (500 mL) was added to a suspension of NaH (66 g, 1.7 mol, 60% purity) in THF (2.0 L) drop-wise at 25° C. The mixture was stirred at 25° C. for 30 min, the mixture was heated at 60° C. for another 2 h. The mixture was poured into water (1000 mL), extracted with EtOAc (800 mL×3). The combined organic layers were washed with brine (1200 mL×2), dried over Na₂SO₄, filtered and concentrated in vacuum. The residue was purified by silica gel column chromatography (PE:EtOAc=40:1-20:1-3:1) to obtain 5-bromo-3-(dimethoxymethyl)-1H-pyrazolo[3,4-c]pyridine (XLIII) (63 g, 232 mmol, 27.9% yield) as a yellow solid. ¹H NMR (300 MHz, CDCl₃) δ ppm 1.43 (s, 9H), 3.39 (s, 6H), 4.75-5.01 (m, 1H), 7.31-7.43 (m, 2H), 8.31 (s, 1H); ESIMS found for C₉H₁₀BrN₃O₂ m/z 372.0 (⁷⁹BrM+H).

Step 4

A mixture of 5-bromo-3-(dimethoxymethyl)-1H-pyrazolo[3,4-c]pyridine (XLIII) (126 g, 463 mmol) and H₂O (100 mL) in HOAc (500 mL) was stirred at 25° C. for 3 h. The mixture was concentrated in vacuum to produce 5-bromo-1H-pyrazolo[3,4-c]pyridine-3-carbaldehyde (XLIV) (83 g, crude) as a yellow solid. The crude product was used on next step directly. ¹H NMR (300 MHz, DMSO-d₆) δ ppm 8.18 (s, 1H), 9.04 (s, 1H), 10.21 (s, 1H), 14.75 (br s, 1H); ESIMS found for C₇H₄BrN₃O m/z 226.0 (⁷⁹BrM+H).

Step 5

To a mixture of 5-bromo-1H-pyrazolo[3,4-c]pyridine-3-carbaldehyde (XLIV) (83 g, 367 mmol, crude) and DHP (77 g, 918 mmol, 83.9 mL) in DCM (500 mL) was added p-TsOH.H₂O (3.5 g, 18 mmol) at 25° C. The mixture was stirred at 25° C. for 5 h. The mixture was pour into saturated aq. NaHCO₃ (400 mL), extracted with EtOAc (500 mL×3). The combined organic layers were washed with brine (600 mL×2), dried over Na₂SO₄, filtered and concentrated in vacuum. The residue was purified by a silica gel column chromatography (PE:EtOAc=50:1→20:1→5:1) to yield 5-bromo-1-(tetrahydro-2H-pyran-2-yl)-1H-pyrazolo[3,4-c]pyridine-3-carbaldehyde (XLV) (66 g, 213 mmol, 58.0% yield) as a white solid. ¹H NMR (400 MHz, CDCl₃) δ ppm 1.70-1.96 (m, 3H), 2.05-2.30 (m, 2H), 2.38-2.60 (m, 1H), 3.82 (dt, J=11.67, 5.96 Hz, 1H), 3.90-4.02 (m, 1H), 5.93 (dd, J=7.91, 3.14 Hz, 1H), 8.38 (s, 1H) 9.01 (s, 1H), 10.23 (s, 1H); ESIMS found for C₁₂H₁₂BrN₃O₂ m/z 310.0 (⁷⁹BrM+H).

Preparation of intermediate 5-chloro-1-(tetrahydro-2H-pyran-2-yl)-1H-pyrazolo[4,3-b]pyridine-3-carbaldehyde (LI) is depicted below in Scheme 8.

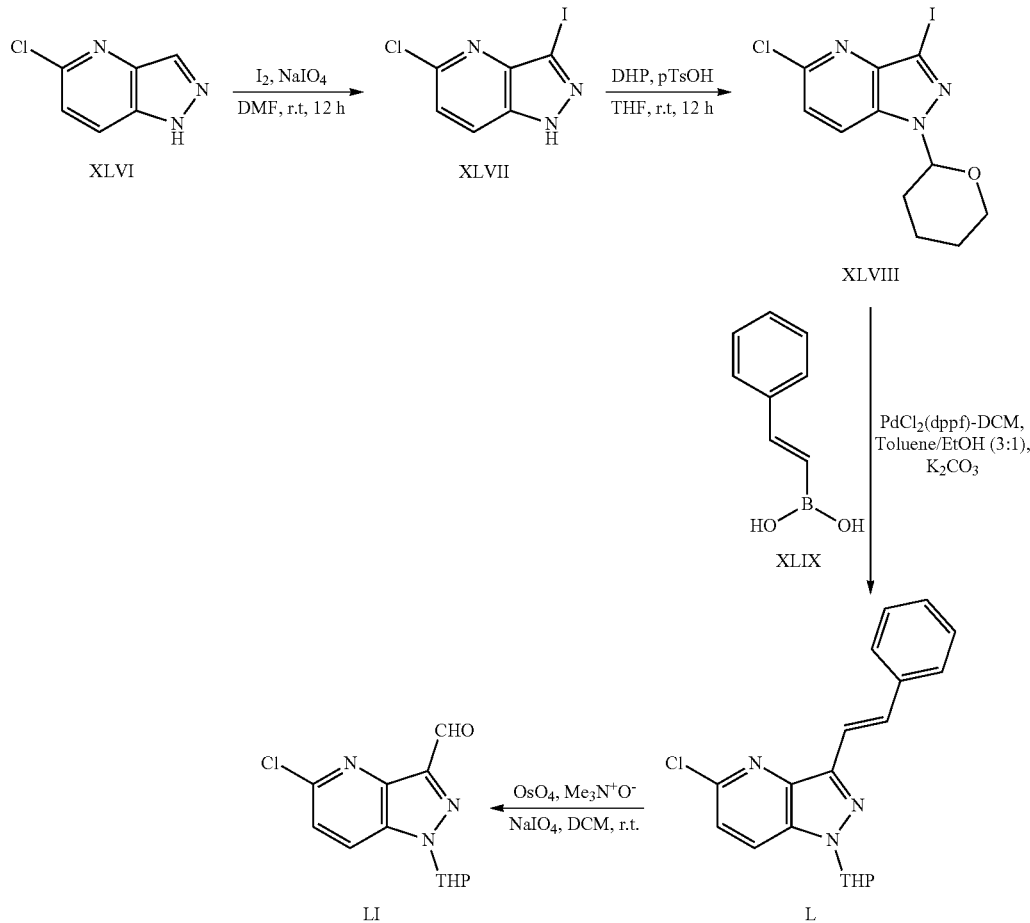

Scheme 8

Step 1

To a solution of 5-chloro-1H-pyrazolo[4,3-b]pyridine (XLVI) (13 g, 84.7 mmol) in DMF (100 mL) was added iodine (43.0 g, 169 mmol) followed by potassium hydroxide powder (23.75 g, 423 mmol) portion wise under ice water cooling. The reaction mixture was stirred at 25° C. overnight. The solid KOH was filtered off, washed with EtOAc, most of the DMF was removed under vacuum and the residue was diluted with water (200 mL) and extracted with 5×200 mL EtOAc, washed with brine (500 mL), dried over Na₂SO₄ and concentrated to give 5-chloro-3-iodo-1H-pyrazolo[4,3-b]pyridine (XLVII) as an orange solid (23.5 g, 84.1 mmol, 99.3% yield). ESIMS found for C₆H₃ClIN₃ m/z 279.9 (M+H).

Step 2

A mixture of 5-chloro-3-iodo-1H-pyrazolo[4,3-b]pyridine (XLVII) (23.5 g, 84.1 mmol) and p-toluenesulfonic acid (3.20 g, 16.82 mmol) in THF (200 mL) was heated to 60° C. for 12 h. The solvents were concentrated and the residue taken in EtOAc (300 mL), washed with sat. NaHCO₃ (200 mL), and brine solution (200 mL). The organic layer was dried over anhydrous Na$_2$SO$_4$, and concentrated to give crude 5-chloro-3-iodo-1-(tetrahydro-2H-pyran-2-yl)-1H-pyrazolo[4,3-b]pyridine (XLVIII) as yellow gummy syrup (30.2 g, 83.1 mmol, 98.8% yield), which was used without further purification for the Suzuki coupling. ESIMS found for C$_{11}$H$_{11}$ClIN$_3$O m/z 364.0 (M+H).

Step 3

A slurry of 5-chloro-3-iodo-1-(tetrahydro-2H-pyran-2-yl)-1H-pyrazolo[4,3-b]pyridine (XLVIII) (30.2 g, 83.1 mmol), (E)-styrylboronic acid (XLIX) (14.75 g, 100 mmol) and 2 M aqueous potassium carbonate (83 mL, 166 mmol)

carbaldehyde (LI) as a white solid (3.641 g, 13.7 mmol, 81.0% yield). $^1$H NMR (CDCL$_3$, 500 MHz) δ ppm 1.71-1.79 (m, 2H), 1.79-1.88 (m, 1H), 2.11-2.25 (m, 2H), 2.43-2.52 (m, 1H), 3.76-3.83 (m, 1H), 3.91-3.98 (m, 1H), 5.87 (dd, J=8.23, 3.02 Hz, 1H), 7.40 (d, J=8.78 Hz, 1H), 8.08 (d, J=9.06 Hz, 1H), 10.38 (s, 1H); ESIMS found for C$_{12}$H$_{12}$ClN$_3$O$_2$ m/z 266.0 (M+H).

Preparation of intermediate 5-bromo-1-(tetrahydro-2H-pyran-2-yl)-1H-indazole-3-carboxylic acid (LVI) is depicted below in Scheme 9.

Scheme 9

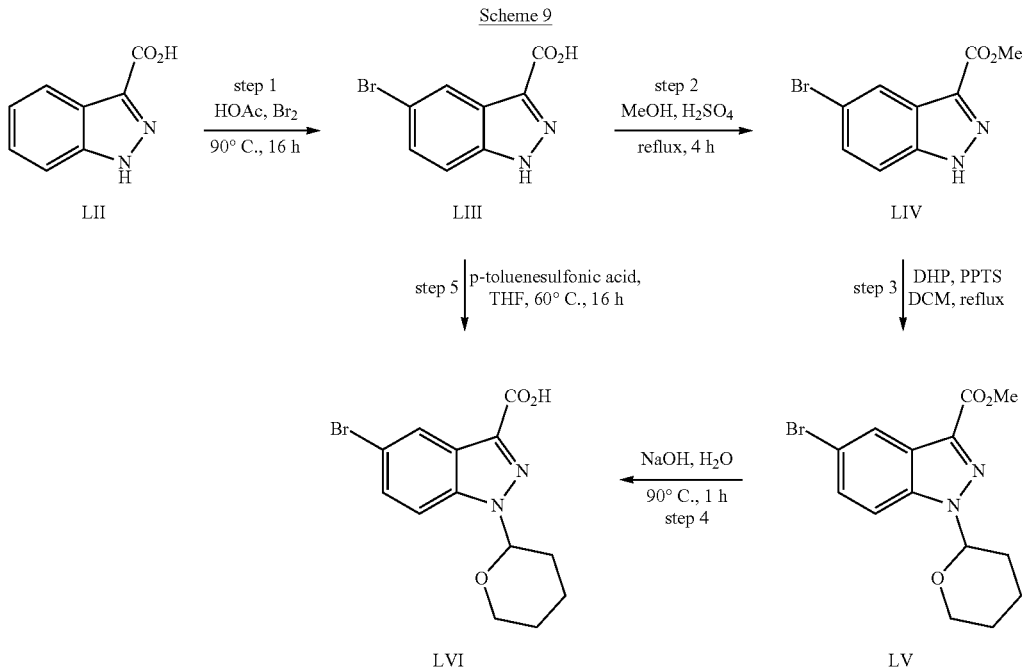 [SMILES: O=C(O)c1n[nH]c2ccccc12 ; O=C(O)c1n[nH]c2ccc(Br)cc12 ; COC(=O)c1n[nH]c2ccc(Br)cc12 ; O=C(O)c1nn(C2CCCCO2)c2ccc(Br)cc12 ; COC(=O)c1nn(C2CCCCO2)c2ccc(Br)cc12]

in toluene (240.0 mL) and EtOH (80.0 mL) was purged with argon for 5 minutes before and after adding PdCl$_2$(dppf)-CH$_2$Cl$_2$ adduct (3.39 g, 4.15 mmol). The reaction was heated at refluxed at 110° C. for 6 h. The reaction mixture was cooled and diluted with water (200 mL), extracted with EtOAc (2×300 mL), dried and evaporated, the residue was purified by column chromatography (0-30% EtOAc/Hexane), to obtain ($_E$)-5-chloro-3-styryl-1-(tetrahydro-2H-pyran-2-yl)-1H-pyrazolo[4,3-b]pyridine (L) as a white solid (21.1 g, 62.1 mmol, 74.8% yield). ESIMS found for C$_{19}$H$_{18}$ClN$_3$O m/z 340.1 (M+H).

Step 4

To a solution of (E)-5-chloro-3-styryl-1-(tetrahydro-2H-pyran-2-yl)-1H-pyrazolo[4,3-b]pyridine (L) (5.745 g, 16.91 mmol) and trimethylamine oxide (2.54 g, 33.8 mmol) in DCM (70.0 mL) under an atmosphere of dry argon was added osmium (VIII) oxide (0.215 g, 0.845 mmol). The reaction mixture was stirred for 3 h at room temperature. After complete conversion of olefin to diol (by LCMS), sodium periodate (5.42 g, 25.4 mmol) in water (50.0 mL) was added and the mixture was stirred for another 2 h at room temperature. Reaction mixture was diluted with DCM, washed water (100 mL), brine (100 mL), dried over Na$_2$SO$_4$ and evaporated. The crude residue was purified by chromatography (0-70% EtOAc/Hexanes) to obtain 5-chloro-1-(tetrahydro-2H-pyran-2-yl)-1H-pyrazolo[4,3-b]pyridine-3-

Step 1

A suspension of indazole-3-carboxylic acid (LII) (1.0 g, 6.16 mmol) in glacial acetic acid (60 mL) was heated at 120° C. to get a clear solution. The solution was cooled to 90° C. A solution of bromine (0.633 mL, 12.33 mmol) in glacial acetic acid (2 mL) was added slowly to the solution while heating at 90° C. The solution was further heated 16 h at 90° C. The solution was cooled to room temperature, poured into ice water and further stirred at room temperature for 15 min. The solids formed were filtered, washed with cold water and dried under vacuum at room temperature to get 5-bromo-1H-indazole-3-carboxylic acid (LIII) as a white solid (1.30 g, 5.39 mmol, 87.5% yield). $^1$H NMR (DMSO-d$_6$) δ ppm 13.95 (s, 1H), 13.18 (br s, 1H), 8.21 (d, J=1.2 Hz, 1H), 7.65 (d, J=7.0 Hz, 1H), 7.56 (dd, J=7.0, 1.2 Hz, 1H); ESIMS found for C$_8$H$_4$BrN$_2$O$_2$ m/z 242.0 (M+H).

Step 2

Concentrated sulfuric acid (1 mL) was added to a suspension of 5-bromo-1H-indazole-3-carboxylic acid (LIII) (1.30 g, 5.39 mmol) in dry MeOH (50 mL) and heated to reflux for 4 h under argon. The solution was cooled to room temperature and the MeOH was evaporated under vacuum. The residue was dissolved in EtOAc and washed with water. The organic phase was dried over Na$_2$SO$_4$, filtered and concentrated to afford methyl 5-bromo-1H-indazole-3-carboxylate (LIV) as a white solid (1.35 g, 5.29 mmol, 98% yield). ¹H NMR (DMSO-d₆) δ ppm 14.13 (s, 1H), 8.21 (d, J=1.6 Hz, 1H), 7.67 (d, J=7.2 Hz, 1H), 7.59 (dd, J=7.2, 1.2 Hz, 1H), 3.92 (s, 3H); ESIMS found for $C_9H_7BrN_2O_2$ m/z 256.0 (M+H).

Step 3

A suspension of methyl 5-bromo-1H-indazole-3-carboxylate (LIV) (1.35 g, 5.29 mmol), pyridinium p-toluenesulfonate (0.143 g, 0.56 mmol) and 3,4 dihydro-2H-pyran (1.02 mL, 11.90 mmol) in anhydrous dichloroethane (20 mL) was refluxed 5 h under argon. The suspension was turned into the clear solution. The solution was cooled and the excess solvent was evaporated under vacuum. The residue was dissolved in EtOAc and washed with dilute NaHCO₃ solution (satd. NaHCO₃ soln/H₂O: 1:9). The organic layer was dried over Na₂SO₄, filtered and concentrated. The residue was purified by column chromatography (100% hexanes→5:95 EtOAc/hexanes) to get methyl 5-bromo-1-(tetrahydro-2H-pyran-2-yl)-1H-indazole-3-carboxylate (LV) as a white solid (1.47 g, 4.34 mmol, 82% yield). ¹H NMR (DMSO-d₆) δ ppm 8.22 (d, J=1.4 Hz, 1H), 7.89 (d, J=7.2 Hz, 1H), 7.68 (dd, J=7.2, 1.6 Hz, 1H), 6.02 (dd, J=8.0, 2.4 Hz, 1H), 3.94 (s, 3H), 3.88 (m, 1H), 3.79 (m, 1H), 2.37-2.31 (m, 1H), 2.05-1.96 (m, 2H), 1.77-1.73 (m, 1H). 1.60-1.58 (m, 2H); ESIMS found for $C_{14}H_{15}BrN_2O_3$ m/z 340.0 (M+H).

Step 4

2 N Aqueous NaOH solution (10 mL) was added to a suspension of methyl 5-bromo-1-(tetrahydro-2H-pyran-2-yl)-1H-indazole-3-carboxylate (LV) (1.30 g, 3.83 mmol) in water (20 mL) and heated at 90° C. for 1 h. The solution was cooled to room temperature, diluted with ice water and acidified to pH 3.0 with 10% aqueous HCl. The solids formed were filtered, washed with cold water and dried under vacuum at room temperature to get 5-bromo-1-(tetrahydro-2H-pyran-2-yl)-1H-indazole-3-carboxylic acid (LIV) as a white solid (0.87 g, 2.68 mmol, 70% yield). ESIMS found for $C_{13}H_{13}BrN_2O_3$ m/z 326.0 (M+H).

Step 5

To a solution of 5-bromo-1H-indazole-3-carboxylic acid (LIII) (59.8 g, 248 mmol) in THF (800 mL) under argon was added 3,4 dihydro-2H-pyran (50.6 mL, 558 mmol) and p-TsOH (4.72 g, 24.8 mmol). The reaction was heated to reflux at 60° C. for 16 h. An additional portion of p-TsOH (0.025 eq) and 3,4 dihydro-2H-pyran (0.56 eq) was added and the reflux continued for 5 h. The solution was concentrated under vacuum. EtOAc was added to the residue and the suspension was filtered and dried under high vacuum overnight to produce 5-bromo-1-(tetrahydro-2H-pyran-2-yl)-1H-indazole-3-carboxylic acid (LVI) as a white solid (49.07 g, 150.9 mmol, 60.8% yield). ESIMS found for $C_{13}H_{13}BrN_2O_3$ m/z 326.3 (M+H).

Preparation of intermediate tert-butyl ((5-bromopyridin-3-yl)methyl)(methyl) carbamate (LIX) is depicted below in Scheme 10.

Scheme 10

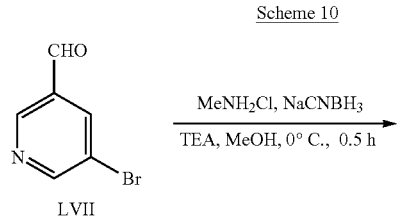

LVII

MeNH₂Cl, NaCNBH₃
TEA, MeOH, 0° C., 0.5 h

-continued

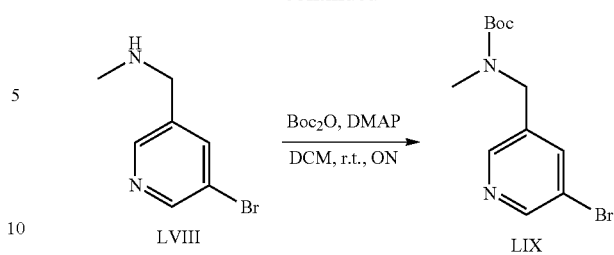

LVIII

Boc₂O, DMAP
DCM, r.t., ON

LIX

Step 1

To stirred mixture of 5-bromonicotinaldehyde (LVII) (2.0 g, 10.75 mmol), methanamine hydrochloride (0.06 mL, 32.26 mmol) and TEA (6.74 mL, 48.38 mmol) in MeOH (20 mL) was added NaCNBH₃ (2.03 g, 32.26 mmol) at 0° C. and the mixture was stirred for 30 min. to 1 h at room temperature. Reaction mixture was quenched with minimum amount of aqueous saturated ammonium chloride solution, concentrated under vacuum and the residue was adsorbed on silica gel, purified by chromatography (0-10% 7N NH₃-MeOH/Chloroform) to obtain 1-(5-bromopyridin-3-yl)-N-methylmethanamine (LVIII) (2.0 g, 9.95 mmol, 92.5% yield) as an yellow syrup. ESIMS found for C7H9BrN2 m/z 201.0 (Br⁷⁹M+H).

Step 2

To a solution of 1-(5-bromopyridin-3-yl)-N-methylmethanamine (LVIII) (2.0 g, 9.95 mmol) and TEA (4.16 mL, 29.84 mmol) in DCM (100 mL) was added di-tert-butyl dicarbonate (3.26 g, 14.92 mmol), DMAP (0.12 g, 0.99 mmol). Reaction mixture was stirred overnight at room temperature. The solvent was evaporated and the residue was purified by column chromatography (0-100% EtOAc/Hexane) to obtain tert-butyl ((5-bromopyridin-3-yl)methyl)(methyl)carbamate (LIX) (1.537 g, 5.10 mmol, 51.3% yield) as a white solid. ESIMS found for $C_{12}H_{17}BrN_2O_2$ m/z 301.05 (Br⁷⁹M+H).

Preparation of intermediate 3-(4-(3,4-diaminopyridin-2-yl)-1H-1,2,3-triazol-1-yl)propan-1-ol (LXIII) is depicted below in Scheme 11.

Scheme 11

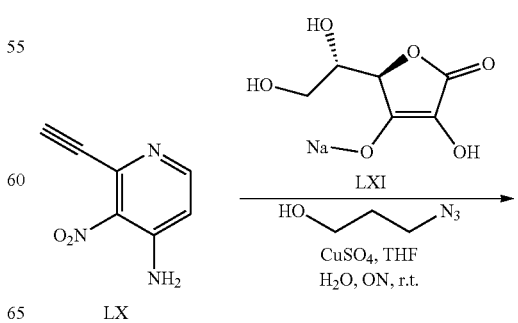

LX    LXI

CuSO₄, THF
H₂O, ON, r.t.

-continued

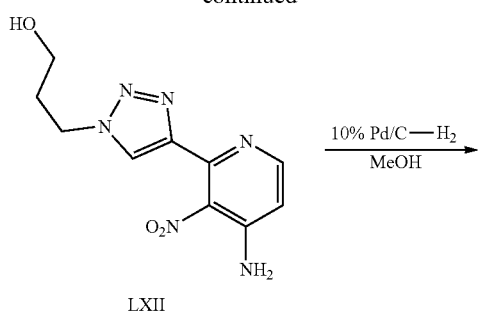

Step 1
A mixture of 2-ethynyl-3-nitropyridin-4-amine (LX) (475 mg, 2.91 mmol), 3-azidopropan-1-ol (6.41 mL, 3.2 mmol), sodium (R)-2-((S)-1,2-dihydroxyethyl)-4-hydroxy-5-oxo-2,5-dihydrofuran-3-olate (LXI) (57.7 mg, 0.290 mmol) and copper(II) sulfate (9.3 mg, 0.060 mmol) in THF (10 mL) and water (3 mL) was stirred overnight at room temperature. Reaction mixture was concentrated and the residue was adsorbed on silica gel, purified by chromatography (0-10% 7 N $NH_3$ in MeOH/$CHCl_3$) to obtain 3-(4-(4-amino-3-nitropyridin-2-yl)-1H-1,2,3-triazol-1-yl)propan-1-ol (LXII) (385 mg, 1.46 mmol, 50.0% yield) as an yellow solid. ESIMS found for $C_{10}H_{12}N_6O_3$ m/z 265.1 (M+H).

Step 2
To a solution of 3-(4-(4-amino-3-nitropyridin-2-yl)-1H-1,2,3-triazol-1-yl)propan-1-ol (LXII) (385 mg, 1.46 mmol) in MeOH (10 mL) was added Pd/C (35.6 mg, 0.290 mmol) under $N_2$. The suspension was degassed under vacuum and purged with $H_2$ several times. The mixture was stirred under $H_2$ (25 psi) at room temperature for 24 h. LC/MS showed the starting material was consumed completely. The reaction mixture was filtered through Celite® and the filter was concentrated to give 3-(4-(3,4-diaminopyridin-2-yl)-1H-1,2,3-triazol-1-yl)propan-1-ol (LXIII) (298 mg, 1.27 mmol, 87.3% yield) as brown solid. ESIMS found $C_{10}H_{14}N_6O$ m/z 235.1 (M+H).

Preparation of intermediate methyl 3-(2',3'-diamino-[1,1'-biphenyl]-3-yl)propanoate (LXVIII) is depicted below in Scheme 12.

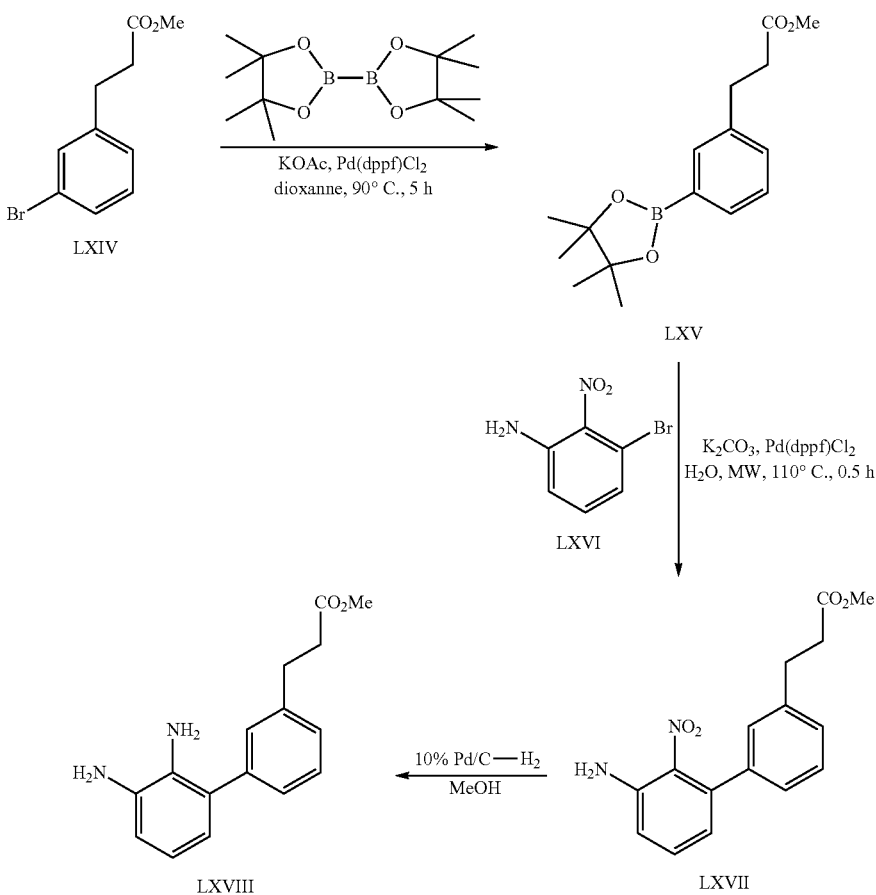

Step 1

A solution of methyl 3-(3-bromophenyl)propanoate (LXIV) (500 mg, 2.06 mmol), bis(pinacolato)diboron (76.4 mL, 3.09 mmol), KOAc (606 mg, 6.17 mmol) and dioxane (10 mL) was purged with argon. Pd(dppf)Cl$_2$ (168 mg, 0.210 mmol) was added to the reaction and purged again with argon. The solution was heated at 90° C. for 5 h. The solution was cooled to room temperature and use for the next step without further workup.

Step 2

To the solution of crude methyl 3-(3-(4,4,5,5-tetramethyl-1,3,2-dioxaborolan-2-yl)phenyl)propanoate (LXV) dioxane (10 mL) was added 3-bromo-2-nitro-aniline (LXVI) (446.4 mg, 2.06 mmol), Pd(dppf)Cl$_2$ (168 mg, 0.210 mmol), and a 2 M aqueous solution of K$_2$CO$_3$ (3.08 mL, 6.17 mmol). The solution was purged with argon and irradiated with microwave at 110° C. for 30 minutes. The solution was cooled to room temperature and then concentrated under reduced pressure. The residue was purified on silica gel (0-100% EtOAc/hexanes) to give methyl 3-(3'-amino-2'-nitro-[1,1'-biphenyl]-3-yl)propanoate (LXVII) as a brown solid (424 mg, 1.41 mmol, 68.6% yield). ESIMS found for C$_{16}$H$_{16}$N$_2$O$_4$ m/z 301.1 (M+H).

Step 3

To a solution of methyl 3-(3'-amino-2'-nitro-[1,1'-biphenyl]-3-yl)propanoate (LXVII) (424 mg, 1.41 mmol) in MeOH (20 mL) was added Pd/C under N$_2$. The suspension was degassed under vacuum and purged with H$_2$ several times. The mixture was stirred under H$_2$ (25 psi) at room temperature for 24 h. LC/MS showed the starting material was consumed completely. The reaction mixture was filtered through Celite® and the filter was concentrated to give methyl 3-(2',3'-diamino-[1,1'-biphenyl]-3-yl)propanoate (LXVIII) (335 mg, 1.24 mmol, 87.8% yield) as brown gum. ESIMS found C$_{16}$H$_{18}$N$_2$O$_2$ m/z 271.1 (M+H).

The following intermediates were prepared in accordance with the procedure described in the above Scheme 12.

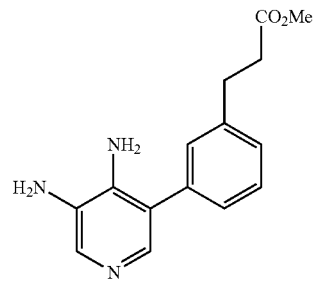

Methyl 3-(3-(4,5-diaminopyridin-3-yl)phenyl)propanoate (LXX): Brown gum (353 mg, 1.30 mmol, 80.7% yield). ESIMS found C$_{15}$H$_{17}$N$_3$O$_2$ m/z 272.0 (M+H).

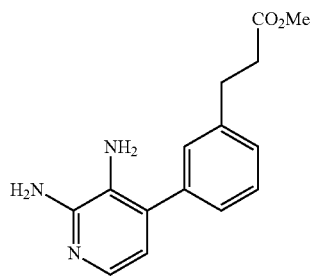

Methyl 3-(3-(2,3-diaminopyridin-4-yl)phenyl)propanoate (LXXI): Dark brown gum (750 mg, 2.76 mmol, 95.7% yield). $^1$H NMR (499 MHz, DMSO-d$_6$) δ ppm 2.65-2.71 (2H, m), 2.90 (2H, t, J=7.55 Hz), 3.59 (3H, s), 4.33 (2H, s), 5.52 (2H, s), 6.32 (1H, d, J=4.94 Hz), 7.21-7.25 (2H, m), 7.27 (1H, s), 7.35 (1H, d, J=5.21 Hz), 7.36-7.40 (1H, m); ESIMS found C$_{15}$H$_{17}$N$_3$O$_2$ m/z 272.1 (M+H).

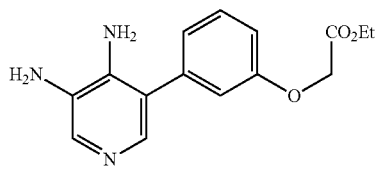

Ethyl 2-(3-(4,5-diaminopyridin-3-yl)phenoxy)acetate (LXXII): Light yellow puffy solid (1.25 g, 4.35 mmol, 98.7% yield). ESIMS found C$_{15}$H$_{17}$N$_3$O$_3$ m/z 288.1 (M+H).

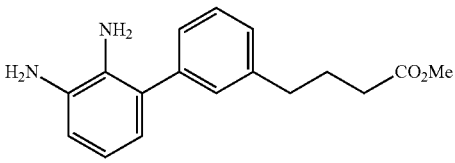

Methyl 4-(2',3'-diamino-[1,1'-biphenyl]-3-yl)butanoate (LXXIII): Dark brown gum (750 mg, 2.64 mmol, 70.3% yield). $^1$H NMR (499 MHz, DMSO-d$_6$) δ ppm 1.86 (2H, quin, J=7.48 Hz), 2.33 (2H, t, J=7.27 Hz), 2.63 (2H, t, J=7.55 Hz), 3.57 (3H, s), 4.04 (2H, br s), 4.56 (2H, br s), 6.35 (1H, Methyl 3-(3-(3,4-diaminopyridin-2-yl)phenyl)propanoate (LXIX): Light yellow viscous oil (780 mg, 2.87 mmol, 108.3% yield). ESIMS found C$_{15}$H$_{17}$N$_3$O$_2$ m/z 272.1 (M+H).

dd, J=7.55, 1.51 Hz), 6.49 (1H, t, J=7.68 Hz), 6.54-6.59 (1H, m), 7.14 (1H, d, J=7.68 Hz), 7.17-7.22 (2H, m), 7.33-7.38 (1H, m); ESIMS found $C_{17}H_{20}N_2O_2$ m/z 285.1 (M+H).

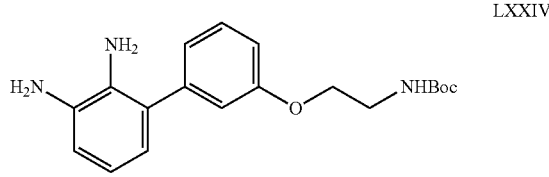 [SMILES: CC(C)(C)OC(=O)NCCOc1cccc(-c2cccc(N)c2N)c1]

LXXIV tert-Butyl (2-((2',3'-diamino-[1,1'-biphenyl]-3-yl)oxy) ethyl)carbamate (LXXIV): Dark brown solid (455 mg, 1.32 mmol, 98.9% yield). $^1$H NMR (499 MHz, DMSO-d$_6$) δ ppm 1.38 (9H, s), 3.27-3.31 (2H, m), 3.98 (2H, t, J=5.76 Hz), 4.07 (2H, s), 4.57 (2H, s), 6.36 (1H, dd, J=7.41, 1.37 Hz), 6.48 (1H, t, J=7.55 Hz), 6.56 (1H, dd, J=7.68, 1.65 Hz), 6.85-6.90 (2H, m), 6.92-6.95 (1H, m), 6.99 (1H, br t, J=5.21 Hz), 7.31-7.37 (1H, m); ESIMS found $C_{19}H_{25}N_3O_3$ m/z 344.1 (M+H).

Preparation of intermediate tert-butyl ((2',3'-diamino-[1,1'-biphenyl]-3-yl)methyl)carbamate (LXXVIII) is depicted below in Scheme 13.

Step 1

A mixture of (3-(((tert-butoxycarbonyl)amino)methyl) phenyl)boronic acid (LXXV) (1.01 g, 4.03 mmol, Combi-Blocks, Inc.), 3-bromo-2-nitro-aniline (LXXVI) (0.87 g, 4.03 mmol), Pd(dppf)Cl$_2$ (160 mg, 0.20 mmol), and a 2 M aqueous solution of K$_3$PO$_4$ (6.04 mL, 12.08 mmol) was taken in dioxane (15 mL). N$_2$ gas was bubbled into the mixture for 10 min and then was heated in microwave at 110° C. for 30 min. The organic layer was separated and concentrated, the residue was adsorbed on silica gel and purified by chromatography (0-100% EtOAc/hexanes) to obtain tert-butyl ((2'-amino-3'-nitro-[1,1'-biphenyl]-3-yl) methyl)carbamate (LXXVII) (1.1 g, 3.20 mmol, 79.6% yield) as a white solid. ESIMS found for $C_{18}H_{21}N_3O_4$ m/z 361.2 (M+H$_2$O).

Step 2

A solution of tert-butyl ((2'-amino-3'-nitro-[1,1'-biphenyl]-3-yl)methyl)carbamate (LXXVII) (1.3 g, 3.79 mmol) and palladium on carbon (120 mg, 0.110 mmol) in MeOH (20 mL) was stirred overnight under Hydrogen gas (1 atm). After completing the reduction, the reaction was filtered through Celite, washed with MeOH and the solvent was evaporated and dried to obtain tert-butyl ((2',3'-diamino-[1,1'-biphenyl]-3-yl)methyl)carbamate (LXXVIII) (1.01 g, 3.22 mmol, 85.1% yield) as a brown solid. ESIMS found for $C_{18}H_{23}N_3O_2$ m/z 314.1 (M+H).

The following intermediate was prepared in accordance with the procedure described in the above Scheme 13.

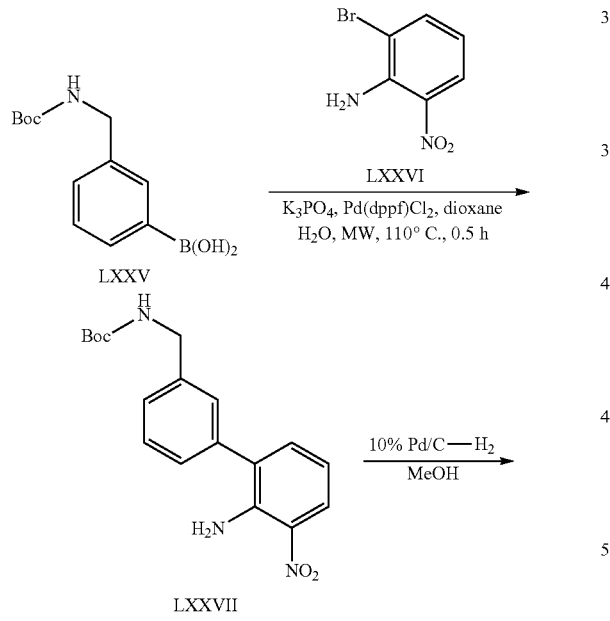

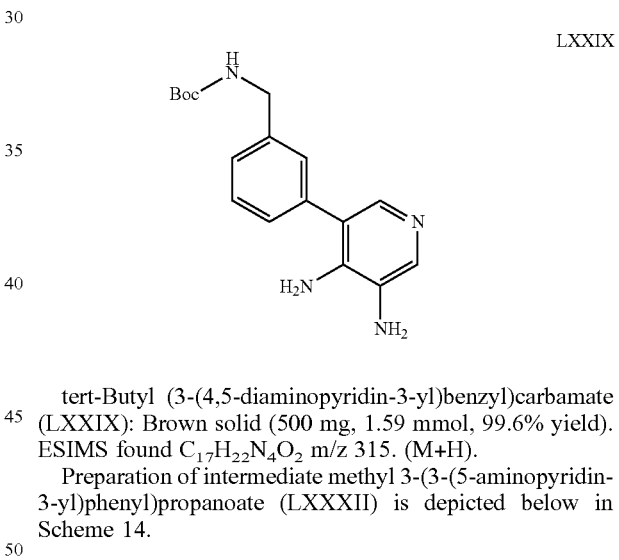

tert-Butyl (3-(4,5-diaminopyridin-3-yl)benzyl)carbamate (LXXIX): Brown solid (500 mg, 1.59 mmol, 99.6% yield). ESIMS found $C_{17}H_{22}N_4O_2$ m/z 315. (M+H).

Preparation of intermediate methyl 3-(3-(5-aminopyridin-3-yl)phenyl)propanoate (LXXXII) is depicted below in Scheme 14.

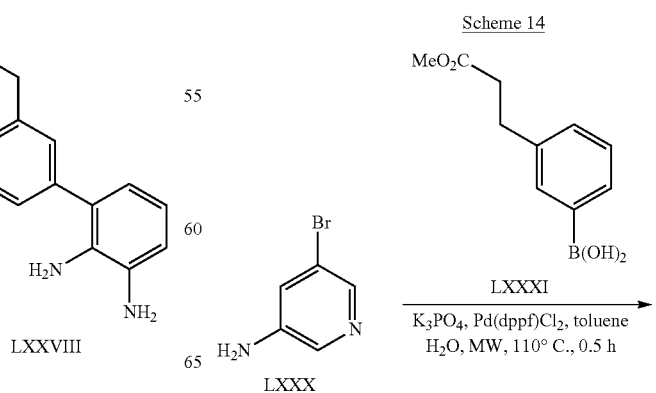

-continued

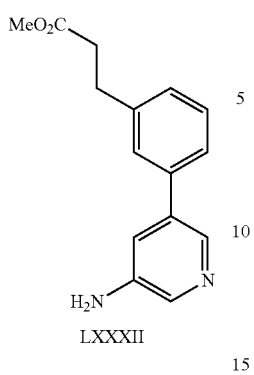

LXXXII

-continued

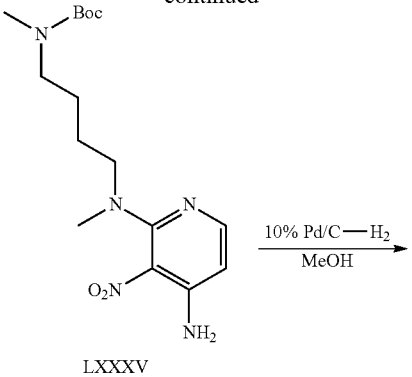

LXXXV

Step 1

To the solution of (3-(3-methoxy-3-oxopropyl)phenyl) boronic acid (LXXXI) dioxane (421 mg, 2.02 mmol, Combi-Blocks Inc.) was added 5-bromopyridin-3-amine (LXXX) (446 mg, 2.06 mmol, Combi-Blocks Inc.), Pd(dppf)Cl$_2$ (82.6 mg, 0.10 mmol), and a 2 M aqueous solution of K$_2$CO$_3$ (2.0 mL, 4.05 mmol). The solution was purged with argon and irradiated with microwave at 110° C. for 30 minutes. The solution was cooled to room temperature and then concentrated under reduced pressure. The residue was purified on silica gel (0-10% 7N NH$_3$ in MeOH/CHCl$_3$) to give methyl 3-(3-(5-aminopyridin-3-yl)phenyl)propanoate (LXXXII) as a beige solid (560 mg, 2.18 mmol, 108% yield). ESIMS found for C$_{15}$H$_{16}$N$_2$O$_2$ m/z 257.1 (M+H).

Preparation of intermediate tert-butyl (4-((3,4-diaminopyridin-2-yl)(methyl)amino) butyl)(methyl)carbamate (LXXXVI) is depicted below in Scheme 15.

Scheme 15

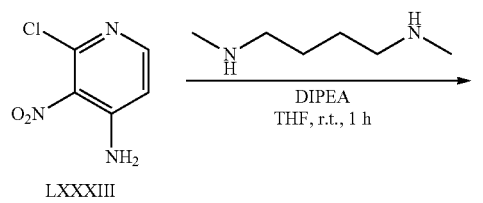

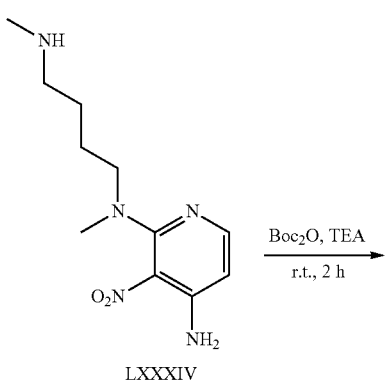

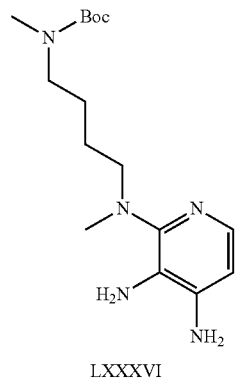

LXXXVI

Step 1

A mixture of 2-chloro-3-nitropyridin-4-amine (LXXXIII) (1.0 g, 5.76 mmol) and DIPEA (1.0 mL, 5.76 mmol) in THF (20 mL) was stirred at room temperature for 1 h. The reaction was concentrated to dryness and the residue was taken up in EtOAc and the organic layer was washed with 2× water then 1× brine solution. The organic layers were then separated and dried (MgSO$_4$) before concentration to dryness to obtain N$^2$-methyl-N$^2$-(4-(methylamino)butyl)-3-nitropyridine-2,4-diamine (LXXXIV) (160 mg, 6.32 mmol, 109.6% yield) as dark brown gum which was used for next step without purification. ESIMS found for C$_{11}$H$_{19}$N$_5$O$_2$ m/z 254.1 (M+H).

Step 2

To a stirred solution of N$^2$-methyl-N$^2$-(4-(methylamino) butyl)-3-nitropyridine-2,4-diamine (LXXXIV) (1.459 g, 5.76 mmol) in THF (20 mL) was added TEA (2.0 mL, 14.4 mmol) followed by the addition of di-tert-butyl dicarbonate (1.38 mg, 6.34 mmol) and the mixture was stirred for 2 h at 25° C. The solvents were concentrated, the residue partitioned between EtOAc/sat. NaHCO$_3$, the organic layer was separated and were washed with water and brine. The organic layer was then separated and dried (MgSO$_4$) before concentration to dryness. The crude was then purified by flash column chromatography (EtOAc/hexanes 0-30%). The desired fractions were concentrated to dryness in vacuo to obtain tert-butyl (4-((4-amino-3-nitropyridin-2-yl)(methyl) amino)butyl)(methyl)carbamate (LXXXV) (1.95 mg, 5.51 mmol, 95.7% yield) as dark brown gum. ESIMS found for $C_{16}H_{27}N_5O_4$ m/z 354.2 (M+H).

Step 3

A solution of tert-butyl (4-((4-amino-3-nitropyridin-2-yl) (methyl)amino) butyl)(methyl)carbamate (LXXXV) (1.94 g, 5.49 mmol) and palladium on carbon (400 mg, 5.49 mmol) in MeOH (20 mL) was stirred overnight under hydrogen gas (1 atm). After completing the reduction, the reaction was filtered through Celite, washed with MeOH and the solvent was evaporated and dried to obtain tert-butyl (4-((3,4-diaminopyridin-2-yl)(methyl)amino)butyl)(methyl) carbamate (LXXXVI) (1.78 g, 5.50 mmol, 100% yield) as a dark brown gum. ESIMS found for $C_{16}H_{29}N_5O_2$ m/z 323.2 (M+H).

Preparation of intermediate tert-butyl trans-4-(2,3-diaminobenzamido)cyclohexyl) carbamate (XC) is depicted below in Scheme 16.

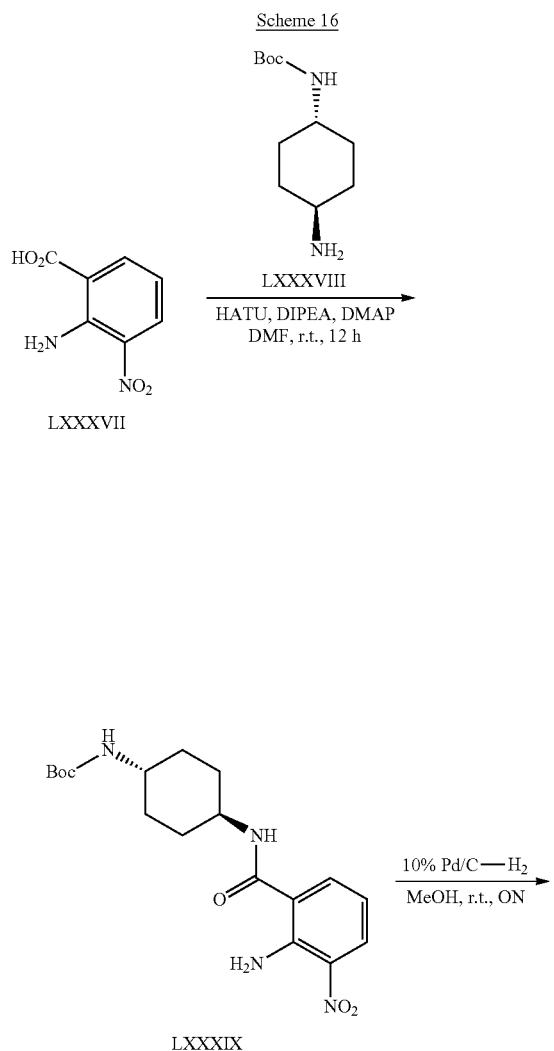

Step 1

A mixture of 2-amino-3-nitrobenzoic acid (LXXXVII) (500 mg, 2.75 mmol, Sigma Aldrich), tert-butyl trans-4-aminocyclohexyl)carbamate (LXXXVIII) (588 mg, 2.75 mmol, Combi-Block, Inc.), HATU (1565.76 mg, 4.12 mmol), N-ethyl-N-isopropyl-propan-2-amine (0.96 mL, 5.49 mmol) and DMAP (17 mg, 0.140 mmol) in DMF (5 mL) was stirred for 12 h room temperature. Precipitated solids were filtered and washed with aqueous saturated bicarbonate solution and water. The solid was dried under high vacuum to obtain tert-butyl (trans-4-(2-amino-3-nitrobenzamido)cyclohexyl)carbamate (LXXXIX) (950 mg, 2.510 mmol, 91.4% yield) as a beige solid. The product was used for next step without further purification. ESIMS found for $C_{18}H_{26}N_4O_5$ m/z 401.2 (M+Na).

Step 2

A solution of obtain tert-butyl (trans-4-(2-amino-3-nitrobenzamido)cyclohexyl) carbamate (LXXXIX) (900 mg, 2.38 mmol) and palladium on carbon (51 mg, 0.48 mmol) in MeOH (20 mL) was stirred overnight under hydrogen gas (1 atm). After completing the reduction, the reaction was filtered through Celite, washed with MeOH, concentrated under vacuum, and purified by column chromatography (0→5% 7N $NH_3$-MeOH/$CHCl_3$) to obtain tert-butyl trans-4-(2,3-diaminobenzamido)cyclohexyl) carbamate (XC) (750 mg, 2.15 mmol, 90.5% yield) as a beige solid. $^1$H NMR (499 MHz, DMSO-$d_6$) δ ppm 1.17-1.29 (2H, m), 1.29-1.44 (2H, m), 1.38 (9H, s), 1.79 (4H, br d, J=10.98 Hz), 3.12-3.24 (1H, m), 3.60-3.72 (1H, m), 4.59 (2H, br s), 5.80 (2H, br s), 6.37 (1H, t, J=7.82 Hz), 6.61 (1H, dd, J=7.68, 1.10 Hz), 6.72 (1H, br d, J=7.96 Hz), 6.81 (1H, d, J=7.14 Hz), 7.82 (1H, br d, J=7.96 Hz); ESIMS found for $C_{18}H_{28}N_4O_3$ m/z 349.2 (M+H).

Example 1

Preparation of (Z)-2$^1$H,3$^1$H-8-Aza-2(5,3),3(2,4)-diindazola-1(3,5)-pyridina-4(1,3)-benzenacyclooctaphan-7-one (1) is depicted below in Scheme 17.

Scheme 17

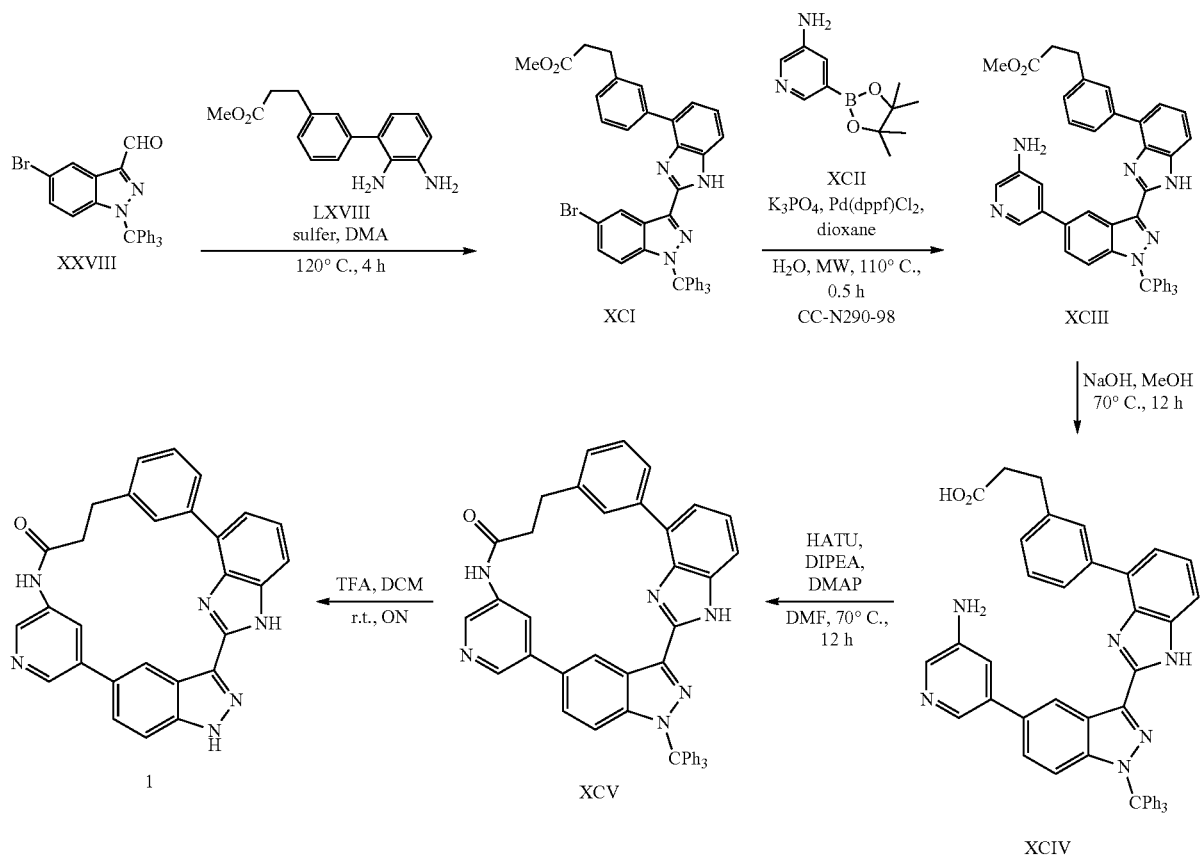

Step 1

A mixture of methyl 3-(2',3'-diamino-[1,1'-biphenyl]-3-yl)propanoate (XXVIII) (579 mg, 1.24 mmol), Sulfur (80 mg, 2.48 mmol), and methyl 3-(2',3'-diamino-[1,1'-biphenyl]-3-yl)propanoate (LXVIII) (335 mg, 1.24 mmol) in DMA (2 mL) was heated at 120° C. for 2 h. The reaction mixture was cooled and concentrated, the residue was adsorbed on silica gel, purified by column chromatography (0-100% EtOAc/hexanes) to obtain methyl 3-(3-(2-(5-bromo-1-trityl-1H-indazol-3-yl)-1H-benzo[d]imidazol-4-yl)phenyl)propanoate (XCI) (657 mg, 0.916 mmol, 73.9% yield) as a brown solid. ESIMS found for $C_{43}H_{33}BrN_4O_2$ m/z 717.2 ($^{79}$BrM+H).

Step 2

A mixture of 5-(4,4,5,5-tetramethyl-1,3,2-dioxaborolan-2-yl)pyridin-3-amine (XCII) (206 mg, 0.930 mmol, Combi-Block, Inc.), methyl 3-(3-(2-(5-bromo-1-trityl-1H-indazol-3-yl)-1H-benzo[d]imidazol-4-yl)phenyl)propanoate (XCI) (335 mg, 0.470 mmol), Pd(dppf)Cl$_2$ (38 mg, 0.050 mmol), and a 2 M aqueous solution of K$_3$PO$_4$ (0.7 mL, 1.4 mmol) was taken in dioxane (4 mL). N$_2$ gas was bubbled into the mixture for 10 min and then was heated in microwave at 110° C. for 30 min. The organic layer was separated and concentrated, the residue was adsorbed on silica gel, purified by chromatography (0-100% EtOAc/hexane) to obtain methyl 3-(3-(2-(5-(5-aminopyridin-3-yl)-1-trityl-1H-indazol-3-yl)-1H-benzo[d]imidazol-4-yl)phenyl)propanoate (XCIII) (96 mg, 0.131 mmol, 28.1% yield) as a white solid. ESIMS found for $C_{48}H_{38}N_6O_2$ m/z 731.3 (M+H).

Step 3

A mixture of methyl 3-(3-(2-(5-(5-aminopyridin-3-yl)-1-trityl-1H-indazol-3-yl)-1H-benzo[d]imidazol-4-yl)phenyl)propanoate (XCIII) (96 mg, 0.130 mmol), and a 2 M aqueous solution of NaOH (0.13 mL, 0.260 mmol) in MeOH (4 mL) was stirred for 12 h at 70° C. The solvents were concentrated, the residue was diluted with water and acidified with 1N HCl, the precipitated solids were filtered and dried under high vacuum to obtain 3-(3-(2-(5-(5-aminopyridin-3-yl)-1-trityl-1H-indazol-3-yl)-1H-benzo[d]imidazol-4-yl)phenyl)propanoic acid (XCIV) (90 mg, 0.126 mmol, 95.9% yield) as a white solids. ESIMS found for $C_{47}H_{36}N_6O_2$ m/z 717.3 (M+H).

Step 4

A mixture of 3-(3-(2-(5-(5-aminopyridin-3-yl)-1-trityl-1H-indazol-3-yl)-1H-benzo[d]imidazol-4-yl)phenyl)propanoic acid (XCIV) (52 mg, 0.070 mmol), DIPEA (0.04 mL, 0.220 mmol), DMAP (1.78 mg, 0.010 mmol) and HATU (41.5 mg, 0.110 mmol) in DMF (4 mL) was stirred for 12 h at 70° C. The solvents were concentrated, the residue was taken up in EtOAc (50 mL) and the organic layer washed with sat. NaHCO$_3$, water and then with brine. The organic layer was then separated and dried (MgSO$_4$) before concentration to dryness. The crude product was then purified by flash column chromatography (MeOH/CHCl$_3$ 0-10%). The desired fractions were concentrated to dryness in vacuo to give (Z)-2'-trityl-2$^1$H,3$^1$H-8-aza-2(5,3),3(2,4)-diindazola-1 (3,5)-pyridina-4(1,3)-benzenacyclooctaphan-7-one (XCV) (25 mg, 0.036 mmol, 49.2% yield) as a white solids. ESIMS found for $C_{47}H_{34}N_6O$ m/z 699.3 (M+H).

Step 5

To a stirred solution of (Z)-2¹-trityl-2¹H,3¹H-8-aza-2(5, 3),3(2,4)-diindazola-1(3,5)-pyridina-4(1,3)-benzenacyclooctaphan-7-one (XCV) (30 mg, 0.040 mmol) in DCM (1 mL) was added TFA (0.33 mL, 4.29 mmol) and the mixture was stirred overnight at room temperature. The solvent was evaporated and the residue was adsorbed on silica gel, purified by column chromatography (0-10% 7N $NH_4$-MeOH/$CHCl_3$) pure fractions were concentrated and the solids were triturated with methanol, filtered and dried to obtain (Z)-2¹H,3¹H-8-Aza-2(5,3),3(2,4)-diindazola-1(3,5)-pyridina-4(1,3)-benzenacyclooctaphan-7-one 1 (12.0 mg, 0.026 mmol, 61.2% yield) as a white solid. ¹H NMR (499 MHz, DMSO-$d_6$) δ ppm 2.92-2.98 (2H, m), 3.03-3.10 (2H, m), 7.21-7.27 (1H, m), 7.27-7.30 (1H, m), 7.30-7.34 (1H, m), 7.37-7.43 (2H, m), 7.53 (1H, dd, J=7.96, 0.82 Hz), 7.78 (1H, d, J=8.78 Hz), 7.87 (1H, br d, J=8.78 Hz), 8.15-8.36 (1H, m), 8.21 (1H, br s), 8.31 (1H, br s), 8.69 (1H, d, J=1.37 Hz), 8.74 (1H, br s), 9.92 (1H, br s), 13.19 (1H, br s), 13.78 (1H, br s); ESIMS found for $C_{28}H_{20}N_6O$ m/z 457.2 (M+1).

The following compounds were prepared in accordance with the procedures described in the above Example 1.

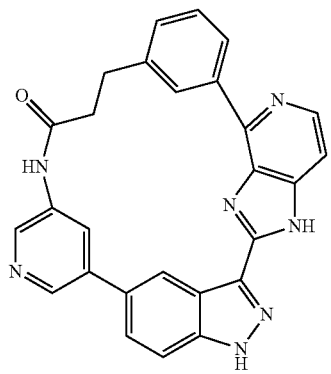

(Z)-2¹H,3¹H-5-Aza-2(4,2)-imidazo[4,5-c]pyridina-3(3,5)-indazola-4(3,5)-pyridina-1(1,3)-benzenacyclooctaphan-6-one 2

White solid (60.0 mg, 0.131 mmol, 43.7% yield). ¹H NMR (499 MHz, DMSO-$d_6$) δ ppm 2.91-2.98 (2H, m), 3.09-3.17 (2H, m), 7.37 (1H, d, J=7.41 Hz), 7.44-7.49 (1H, m), 7.50 (1H, d, J=5.21 Hz), 7.81-7.86 (1H, m), 7.87-7.92 (1H, m), 8.00 (1H, br d, J=7.14 Hz), 8.22 (1H, br s), 8.34 (1H, d, J=1.92 Hz), 8.42 (1H, d, J=5.21 Hz), 8.68 (1H, d, J=0.82 Hz), 8.77 (1H, br s), 8.79 (1H, s), 9.95 (1H, s), 13.60 (1H, s), 13.95 (1H, s); ESIMS found for $C_{27}H_{19}N_7O$ m/z 458.2 (M+1).

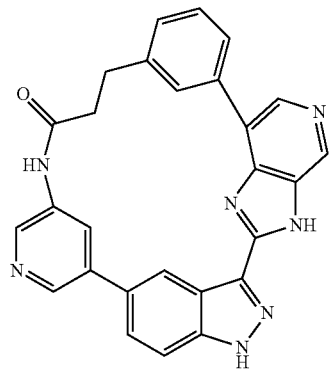

(Z)-2³H,3¹H-5-Aza-2(7,2)-imidazo[4,5-c]pyridina-3(3,5)-indazola-4(3,5)-pyridina-1(1,3)-benzenacyclooctaphan-6-one 3

White solid (25.0 mg, 0.055 mmol, 14.4% yield). ¹H NMR (499 MHz, DMSO-$d_6$) δ ppm 2.94-3.02 (2H, m), 3.03-3.11 (2H, m), 7.34 (1H, br d, J=7.14 Hz), 7.44 (1H, t, J=7.55 Hz), 7.48 (1H, br s), 7.82 (1H, d, J=8.78 Hz), 7.90 (1H, br d, J=8.51 Hz), 8.25 (2H, br s), 8.31 (1H, br s), 8.40 (1H, br s), 8.69 (1H, s), 8.78 (1H, br s), 8.84 (1H, s), 9.94 (1H, br s), 13.68 (1H, br s), 13.99 (1H, br s); ESIMS found for $C_{27}H_{19}N_7O$ m/z 458.1 (M+1).

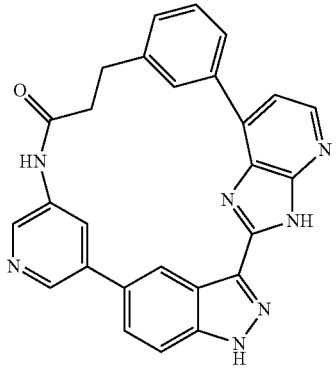

(Z)-2³H,3¹H-5-aza-2(7,2)-imidazo[4,5-b]pyridina-3(3,5)-indazola-4(3,5)-pyridina-1(1,3)-benzenacyclooctaphan-6-one 4

Beige solid (7.5 mg, 0.016 mmol, 45.9% yield). ¹H NMR (500 MHz, DMSO-$d_6$) δ ppm 2.94-2.99 (2H, m), 3.05-3.12 (2H, m), 7.30-7.37 (1H, m), 7.39 (1H, br d, J=7.14 Hz), 7.47 (1H, t, J=7.55 Hz), 7.55 (1H, br s), 7.80 (1H, d, J=8.78 Hz), 7.85-7.92 (1H, m), 8.25 (1H, br s), 8.31 (1H, br s), 8.33-8.43 (1H, m), 8.37 (1H, d, J=4.94 Hz), 8.68 (1H, s), 8.79 (1H, br s), 9.93 (1H, br s), 13.82 (1H, br s), 13.89 (1H, br s); ESIMS found for $C_{27}H_{19}N_7O$ m/z 458.1 (M+1).

5

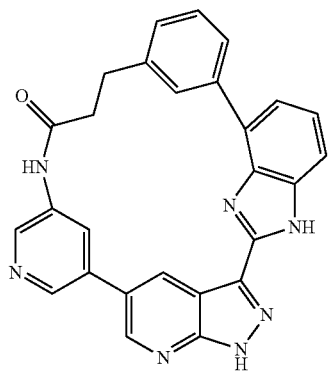

(Z)-2¹H,3¹H-8-Aza-2(5,3)-pyrazolo[3,4-b]pyridina-3(2,4)-benzo[d]imidazola-1(3,5)-pyridina-4(1,3)-benzenacyclooctaphan-7-one 5

Off-white solid (50.0 mg, 0.109 mmol, 63.7% yield). $^1$H NMR (500 MHz, DMSO-d$_6$) δ ppm 2.90-2.99 (2H, m), 3.07-3.14 (2H, m), 7.28-7.32 (2H, m), 7.33-7.37 (1H, m), 7.39-7.43 (1H, m), 7.43-7.47 (1H, m), 7.51-7.57 (1H, m), 8.26 (1H, t, J=2.06 Hz), 8.34 (1H, br s), 8.37 (1H, d, J=2.47 Hz), 8.81 (1H, d, J=1.92 Hz), 9.05-9.06 (1H, m), 9.06-9.08 (1H, m), 9.97 (1H, s), 13.36 (1H, br s), 14.36 (1H, br s); ESIMS found for C$_{27}$H$_{19}$N$_7$O m/z 458.1 (M+1).

6

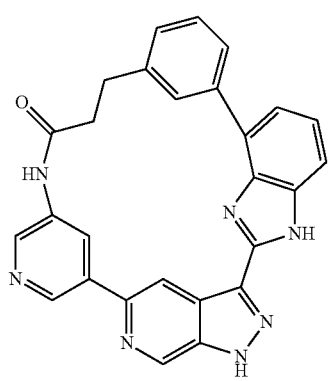

(Z)-2¹H,3¹H-8-Aza-2(5,3)-pyrazolo[3,4-c]pyridina-3(2,4)-benzo[d]imidazola-1(3,5)-pyridina-4(1,3)-benzenacyclooctaphan-7-one 6

Off-white solid (8.0 mg, 0.018 mmol, 18.9% yield). $^1$H NMR (500 MHz, DMSO-d$_6$) δ ppm 2.94-3.02 (2H, m), 3.10-3.16 (2H, m), 7.29-7.37 (3H, m), 7.40-7.46 (2H, m), 7.52-7.57 (1H, m), 8.28-8.44 (1H, m), 8.32 (1H, t, J=2.06 Hz), 8.35 (1H, br s), 8.82 (1H, s), 9.00 (1H, d, J=1.65 Hz), 9.30 (1H, s), 10.00 (1H, br s), 13.36 (1H, br s), 14.34 (1H, br s);

ESIMS found for C$_{27}$H$_{19}$N$_7$O m/z 458.2 (M+1).

7

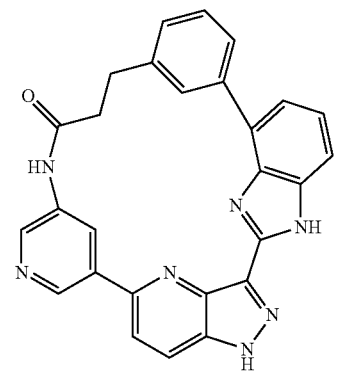

(Z)-2¹H,3¹H-8-Aza-2(5,3)-pyrazolo[4,3-b]pyridina-3 (2,4)-benzo[d]imidazola-1(3,5)-pyridina-4(1,3)-benzenacyclooctaphan-7-one 7

Off-white solid (15.0 mg, 0.033 mmol, 25.4% yield). $^1$H NMR (499 MHz, DMSO-d$_6$) δ ppm 2.85-2.93 (2H, m), 2.95-3.06 (2H, m), 6.99-7.06 (1H, m), 7.16-7.25 (1H, m), 7.26-7.81 (1H, m), 7.31 (1H, br d, J=8.51 Hz), 7.38 (1H, br s), 7.58 (1H, br s), 7.75 (1H, br s), 8.17 (1H, d, J=8.78 Hz), 8.26 (1H, br s), 8.42 (1H, d, J=4.94 Hz), 8.84 (1H, br s), 10.43 (1H, br s), 13.13 (1H, br s), 14.04 (1H, br s); ESIMS found for C$_{27}$H$_{19}$N$_7$O m/z 458.2 (M+1).

38

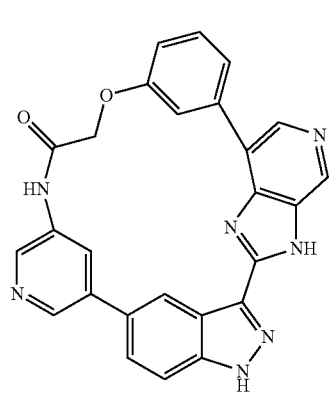

(Z)-2³H,3¹H-8-Oxa-5-aza-2(7,2)-imidazo[4,5-c]pyridina-3(3,5)-indazola-4(3,5)-pyridina-1(1,3)-benzenacyclooctaphan-6-one 38

Beige solid (3.8 mg, 0.008 mmol, 11.8% yield). $^1$H NMR (500 MHz, DMSO-d$_6$) δ ppm 5.18 (2H, s), 7.09 (1H, dt, J=5.97, 2.92 Hz), 7.43-7.50 (2H, m), 7.84 (1H, d, J=8.51 Hz), 7.99 (1H, dd, J=8.78, 1.65 Hz), 8.13-8.18 (1H, m), 8.34 (1H, br s), 8.41 (1H, br s), 8.61 (1H, br s), 8.79 (1H, s), 8.86 (1H, br s), 8.92 (1H, s), 10.29 (1H, s), 13.75 (1H, s), 14.02 (1H, s);

ESIMS found for C$_{26}$H$_{17}$N$_7$O$_2$ m/z 460.15 (M+1).

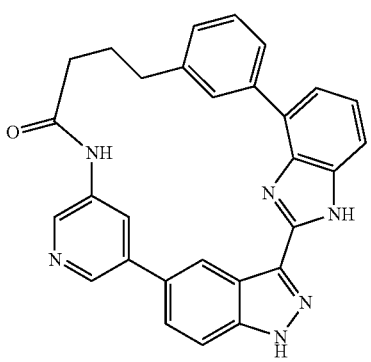
(Z)-2¹H,3¹H-9-Aza-2(5,3),3(2,4)-diindazola-1(3,5)-pyridina-4(1,3)-benzenacyclononaphan-8-one 71
Off-white solid (82.0 mg, 0.17 mmol, 82.8% yield). $^1$H NMR (499 MHz, DMSO-$d_6$) δ ppm 2.05-2.17 (2H, m), 2.44-2.49 (2H, m), 2.75-2.87 (2H, m), 7.27 (1H, d, J=7.41 Hz), 7.31-7.37 (1H, m), 7.38-7.45 (2H, m), 7.54 (1H, dd, J=7.82, 0.96 Hz), 7.60 (1H, d, J=7.68 Hz), 7.80 (1H, d, J=8.51 Hz), 8.01 (1H, br d, J=8.51 Hz), 8.32 (1H, d, J=1.92 Hz), 8.33 (1H, br s), 8.50 (1H, br s), 8.70 (1H, s), 8.78 (1H, d, J=2.20 Hz), 10.30 (1H, br s), 13.20 (1H, br s), 13.84 (1H, br s); ESIMS found for $C_{29}H_{22}N_6O$ m/z 471.1 (M+1).
Example 2
Preparation (Z)-6-Methyl-2¹H,3¹H-6-aza-2(5,3),3(2,4)-diindazola-1(3,5)-pyridina-4(1,3)-benzenacycloheptaphane (22) is depicted below in Scheme 18.
Scheme 18
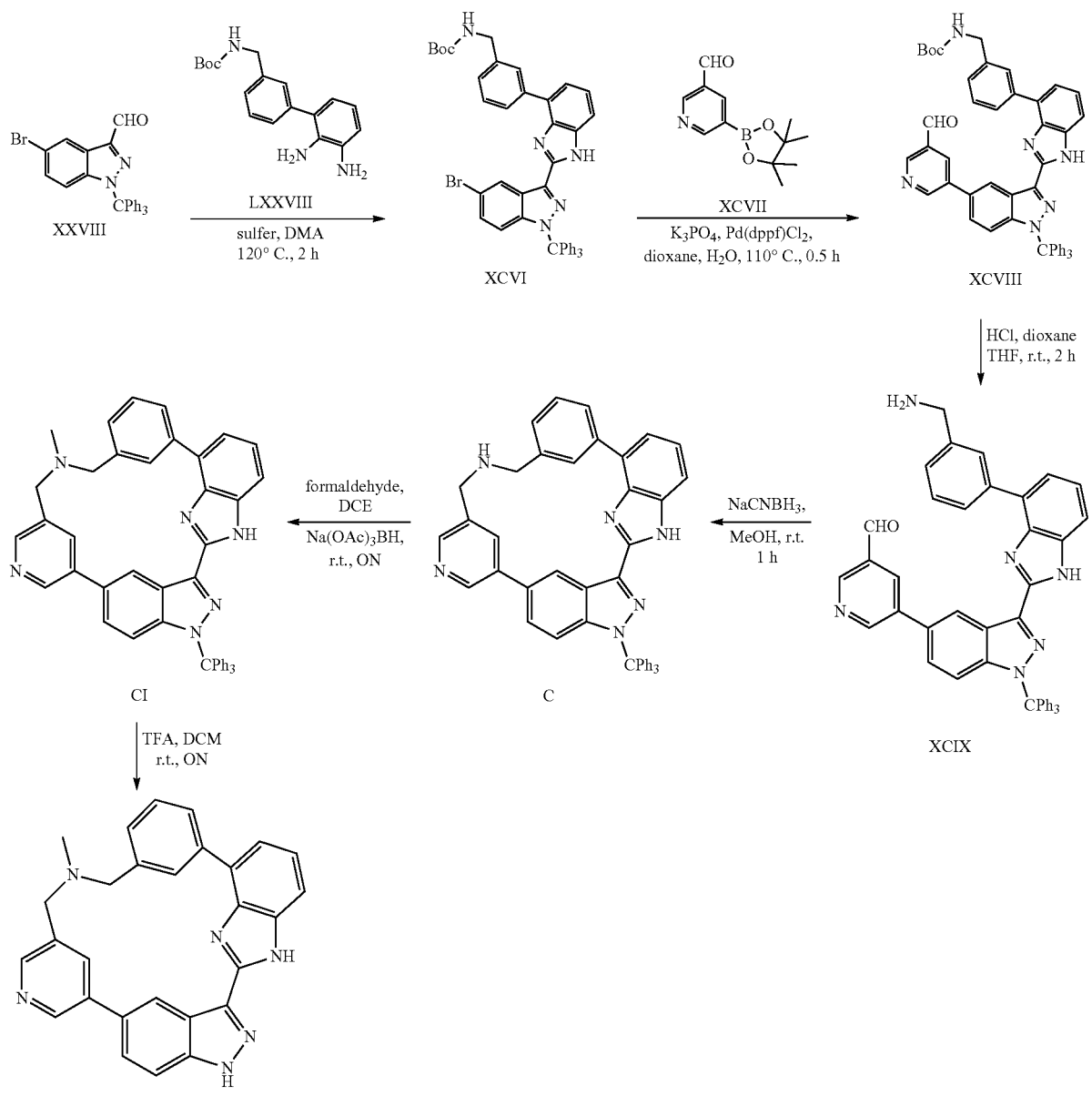

Step 1

A mixture of sulfur (0.31 g, 9.61 mmol), 5-bromo-1-trityl-1H-indazole-3-carbaldehyde (XXVIII) (2.25 g, 4.80 mmol) and tert-butyl ((2',3'-diamino-[1,1'-biphenyl]-3-yl)methyl)carbamate (LXXVIII) (1.51 g, 4.80 mmol) in DMA (10 mL) was heated at 120° C. for 2 h. The reaction mixture was cooled and concentrated, the residue was adsorbed on silica gel, purified by column chromatography (0-100% EtOAc/hexanes) to obtain tert-butyl (3-(2-(5-bromo-1-trityl-1H-indazol-3-yl)-1H-benzo[d]imidazol-4-yl)benzyl)carbamate (XCVI) (1.54 g, 2.02 mmol, 42.1% yield) as a brown solid. ESIMS found for $C_{45}H_{38}BrN_5O_2$ m/z 760.3 (M+H).

Step 2

A mixture of 5-(4,4,5,5-tetramethyl-1,3,2-dioxaborolan-2-yl)nicotinaldehyde (XCVII) (230 mg, 0.990 mmol, Combi-Blocks, Inc.), tert-butyl (3-(2-(5-bromo-1-trityl-1H-indazol-3-yl)-1H-benzo[d]imidazol-4-yl)benzyl)carbamate (XCVI) (500 mg, 0.660 mmol), Pd(dppf)Cl$_2$ (54 mg, 0.070 mmol), a 2 M aqueous solution of $K_3PO_4$ (0.99 mL, 1.97 mmol) was taken in dioxane (5 mL). $N_2$ gas was bubbled into the mixture for 10 min and then was heated in microwave at 110° C. for 30 min. The organic layer was separated and concentrated, the residue was adsorbed on silica gel, purified by chromatography (0-10% 7N NH$_3$-MeOH/CHCl$_3$) to obtain tert-butyl (3-(2-(5-(5-formylpyridin-3-yl)-1-trityl-1H-indazol-3-yl)-1H-benzo[d]imidazol-4-yl) benzyl)carbamate (XCVIII) (405 mg, 0.515 mmol, 78.3% yield) as a white solid. ESIMS found for $C_{51}H_{42}N_6O_3$ m/z 787.3 (M+1).

Step 3

To a solution of tert-butyl (3-(2-(5-(5-formylpyridin-3-yl)-1-trityl-1H-indazol-3-yl)-1H-benzo[d]imidazol-4-yl)benzyl)carbamate (XCVIII) (400 mg, 0.510 mmol) in THF (5 mL) was added 4 N HCl in dioxane (1.27 mL, 5.08 mmol). The reaction mixture was stirred for 2 h at room temperature. The solvent was evaporated and the residue was adsorbed on silica gel, purified by column chromatography (0-5% 7N NH$_3$-MeOH/CHCl$_3$) to obtain 5-(3-(4-(3-(aminomethyl)phenyl)-1H-benzo[d]imidazol-2-yl)-1-trityl-1H-indazol-5-yl)nicotinaldehyde (XCIX) (339 mg, 0.494 mmol, 97.1% yield) as a beige solid. ESIMS found for $C_{46}H_{34}N_6O$ m/z 687.3 (M+1).

Step 4

To stirred mixture of 5-(3-(4-(3-(aminomethyl)phenyl)-1H-benzo[d]imidazol-2-yl)-1-trityl-1H-indazol-5-yl)nicotinaldehyde (XCIX) (338.5 mg, 0.490 mmol) in MeOH (5 mL) was added NaCNBH$_3$ (93 mg, 1.48 mmol) at 0° C. The mixture was then stirred for 30 min. to 1 h at room temperature. The reaction mixture was quenched with minimum amount of aq. saturated ammonium chloride solution, and concentrated under vacuum. The residue was adsorbed on silica gel, purified by chromatography (0-10% 7N NH$_3$-MeOH/CHCl$_3$) to obtain (Z)-trityl-2$^1$H,3$^1$H-6-aza-2(5,3),3(2,4)-diindazola-1(3,5)-pyridina-4(1,3)-benzenacycloheptaphane (C) (20 mg, 0.030 mmol, 6.1% yield) as a white solid. ESIMS found for $C_{46}H_{34}N_6$ m/z 671.3 (M+1).

Step 5

To a solution of (Z)-trityl-2$^1$H,3$^1$H-6-aza-2(5,3),3(2,4)-diindazola-1(3,5)-pyridina-4(1,3)-benzenacycloheptaphane (C) (38 mg, 0.060 mmol) in DCE (1 mL) was added formaldehyde (0.01 mL, 0.060 mmol). The reaction was stirred for 30 min at room temperature before Na(OAc)$_3$BH (24 mg, 0.110 mmol) was added. The reaction mixture was stirred overnight at room temperature. The solution was concentrated and the residue was adsorbed on silica gel and purified by column chromatography (0-10% 7N—NH$_3$-MeOH/CHCl$_3$) to obtain (Z)-6-methyl-2$^1$-trityl-2$^1$H,3$^1$H-6-aza-2(5,3),3(2,4)-diindazola-1(3,5)-pyridina-4(1,3)-benzenacycloheptaphane (CI) (35 mg, 0.051 mmol, 90.2% yield) as a white solid. ESIMS found for $C_{47}H_{36}N_6$ m/z 685.3 (M+1).

Step 6

To a stirred solution of TFA (0.39 mL, 5.11 mmol) in DCM (0.50 mL) was added (Z)-6-methyl-2$^1$-trityl-2$^1$H,3$^1$H-6-aza-2(5,3),3(2,4)-diindazola-1(3,5)-pyridina-4(1,3)-benzenacycloheptaphane (CI) (35 mg, 0.050 mmol) and the mixture was stirred overnight at room temperature. The solvent was evaporated and the residue was adsorbed on silica gel and purified by column chromatography (0-10% 7N NH$_4$-MeOH/CHCl$_3$). The pure fractions were concentrated and the solids were triturated with methanol, filtered and dried to obtain (Z)-6-Methyl-2$^1$H,3$^1$H-6-aza-2(5,3),3(2,4)-diindazola-1(3,5)-pyridina-4(1,3)-benzenacycloheptaphane 22 (12.0 mg, 0.027 mmol, 53.1% yield) as a white solid. $^1$H NMR (499 MHz, DMSO-d$_6$) δ ppm 2.28 (3H, s), 3.47 (2H, s), 3.83 (2H, s), 7.33-7.39 (2H, m), 7.47 (1H, t, J=7.68 Hz), 7.54 (2H, dd, J=7.68, 1.10 Hz), 7.71 (1H, d, J=7.96 Hz), 7.77 (1H, d, J=8.51 Hz), 8.09 (1H, dd, J=8.78, 1.92 Hz), 8.51 (1H, d, J=1.65 Hz), 8.55 (1H, s), 8.84 (1H, s), 9.03 (1H, d, J=1.92 Hz), 9.41 (1H, d, J=1.37 Hz), 13.30 (1H, br s), 13.70 (1H, br s); ESIMS found for $C_{28}H_{22}N_6$ m/z 443.2 (M+1).

The following compounds were prepared in accordance with the procedures described in the above Example 2.

8

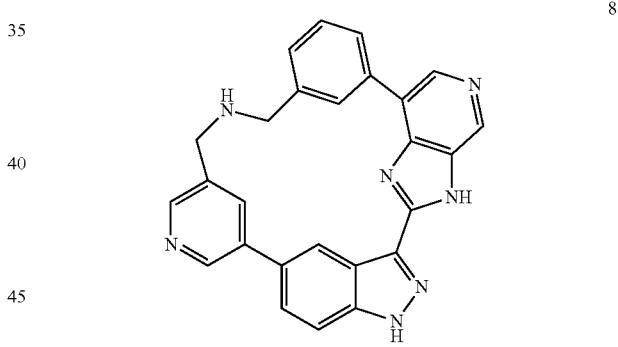

(Z)-2$^3$H,3H-6-Aza-2(7,2)-imidazo[4,5-c]pyridina-3(3,5)-indazola-4(3,5)-pyridina-1(1,3)-benzenacycloheptaphane 8

White solid (10.0 mg, 0.023 mmol, 18.9% yield). $^1$H NMR (499 MHz, DMSO-d$_6$) δ ppm 3.67 (2H, s), 4.07 (2H, s), 7.53-7.57 (1H, m), 7.57-7.60 (1H, m), 7.82 (1H, d, J=8.78 Hz), 7.91 (1H, br d, J=7.41 Hz), 8.10 (1H, dd, J=8.64, 1.51 Hz), 8.51 (1H, s), 8.52 (1H, br s), 8.77 (1H, s), 8.84 (1H, s), 8.93 (1H, d, J=1.92 Hz), 8.96 (1H, s), 9.29 (1H, s), 13.46 (1H, br s), 13.90 (1H, br s); ESIMS found for $C_{26}H_{19}N_7$ m/z 430.15 M+1

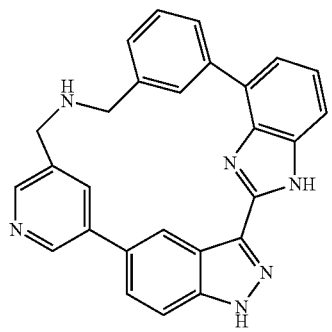

(Z)-2¹H,3¹H-6-Aza-2(5,3),3(2,4)-diindazola-1(3,5)-pyridina-4(1,3)-benzenacycloheptaphane 10

White solid (7.0 mg, 0.016 mmol, 73.1% yield). $^1$H NMR (499 MHz, DMSO-$d_6$) δ ppm 3.69 (2H, br s), 4.07 (2H, br s), 7.34 (1H, t, J=7.68 Hz), 7.49-7.55 (2H, m), 7.55-7.61 (2H, m), 7.76 (1H, d, J=7.41 Hz), 7.78 (1H, d, J=8.78 Hz), 8.07 (1H, dd, J=8.64, 1.78 Hz), 8.46 (1H, s), 8.50 (1H, d, J=1.92 Hz), 8.92 (2H, d, J=1.65 Hz), 9.26 (1H, d, J=0.82 Hz), 13.28 (1H, br s), 13.73 (1H, br s); ESIMS found for $C_{27}H_{20}N_6$ m/z 429.2 (M+1).

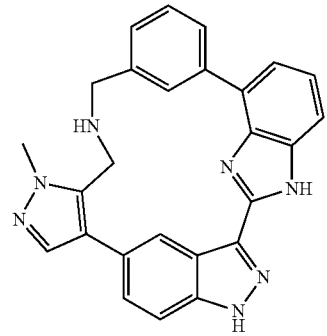

(Z)-Methyl-1¹H,2¹H,3¹H-6-aza-2(5,3),3 (2,4)-diindazola-1 (4,5)-pyrazola-4(1,3)-benzenacycloheptaphane 15

White solid (131.0 mg, 0.304 mmol, 81.5% yield). $^1$H NMR (499 MHz, DMSO-$d_6$) δ ppm 3.96 (3H, s), 4.03 (2H, br s), 4.06 (2H, br s), 7.26 (1H, d, J=7.41 Hz), 7.32 (1H, t, J=7.82 Hz), 7.41 (1H, t, J=7.68 Hz), 7.50 (1H, dd, J=7.96, 0.82 Hz), 7.53 (1H, dd, J=7.68, 0.82 Hz), 7.64-7.70 (3H, m), 7.75 (1H, s), 9.04 (1H, d, J=1.37 Hz), 9.37 (1H, s), 13.10 (1H, br s), 13.59 (1H, br s); ESIMS found for $C_{26}H_{21}N_7$ m/z 432.2 (M+1).

(Z)-1¹,6-Dimethyl-1¹H,2¹H,3¹H-6-aza-2(5,3),3(2,4)-diindazola-1(4,5)-pyrazola-4(1,3)-benzenacycloheptaphane 29

Off-white solid (15.0 mg, 0.034 mmol, 26.3% yield). $^1$H NMR (499 MHz, DMSO-$d_6$) δ ppm 2.08 (3H, s), 3.74 (2H, br s), 3.93 (2H, s), 3.98 (3H, s), 7.23 (1H, d, J=7.68 Hz), 7.32 (1H, t, J=7.82 Hz), 7.41 (1H, t, J=7.68 Hz), 7.47-7.51 (1H, m), 7.57 (1H, dd, J=8.64, 1.51 Hz), 7.67 (2H, s), 7.68 (1H, d, J=2.74 Hz), 7.84 (1H, d, J=8.23 Hz), 9.12 (1H, s), 10.00 (1H, s), 13.09 (1H, br s), 13.62 (1H, br s); ESIMS found for $C_{27}H_{23}N_7$ m/z 446.2 (M+1).

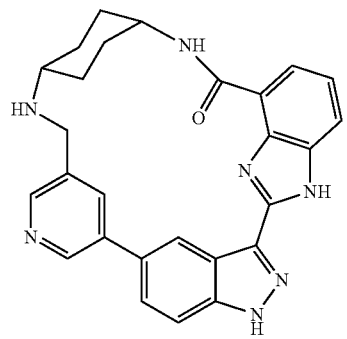

(6¹s,6⁴s,Z)-1¹H,2¹H-5,7-diaza-1 (2,4),2(3,5)-dibenzo[d]imidazola-3(3,5)-pyridina-6(1,4)-cyclohexanacyclooctaphan-8-one 64

Off-white solid (5.0 mg, 0.011 mmol, 10.3% yield). $^1$H NMR (499 MHz, DMSO-$d_6$) δ ppm 1.02-1.21 (5H, m), 1.73 (2H, br d, J=10.70 Hz), 2.00-2.06 (2H, m), 3.70-3.82 (1H, m), 3.80 (2H, s), 7.37 (1H, t, J=7.82 Hz), 7.68-7.72 (1H, m), 7.74 (1H, dd, J=8.64, 1.51 Hz), 7.82-7.86 (1H, m), 7.86-7.89 (1H, m), 8.06 (1H, s), 8.58 (1H, s), 8.71 (1H, d, J=1.37 Hz), 8.75 (1H, d, J=1.92 Hz), 13.59 (1H, br s), 13.98 (1H, br s); ESIMS found for $C_{27}H_{25}N_7O$ m/z 464.3 (M+1).

Example 3

Preparation (1⁴Z,2¹Z)-6-Methyl-1 ¹H,2³H,3¹H-6-aza-2 (7,2)-imidazo[4,5-c]pyridina-3(3,5)-indazola-4(3,5)-pyridina-1(4,1)-triazolacyclononaphane (45) is depicted below in Scheme 19.

Scheme 19

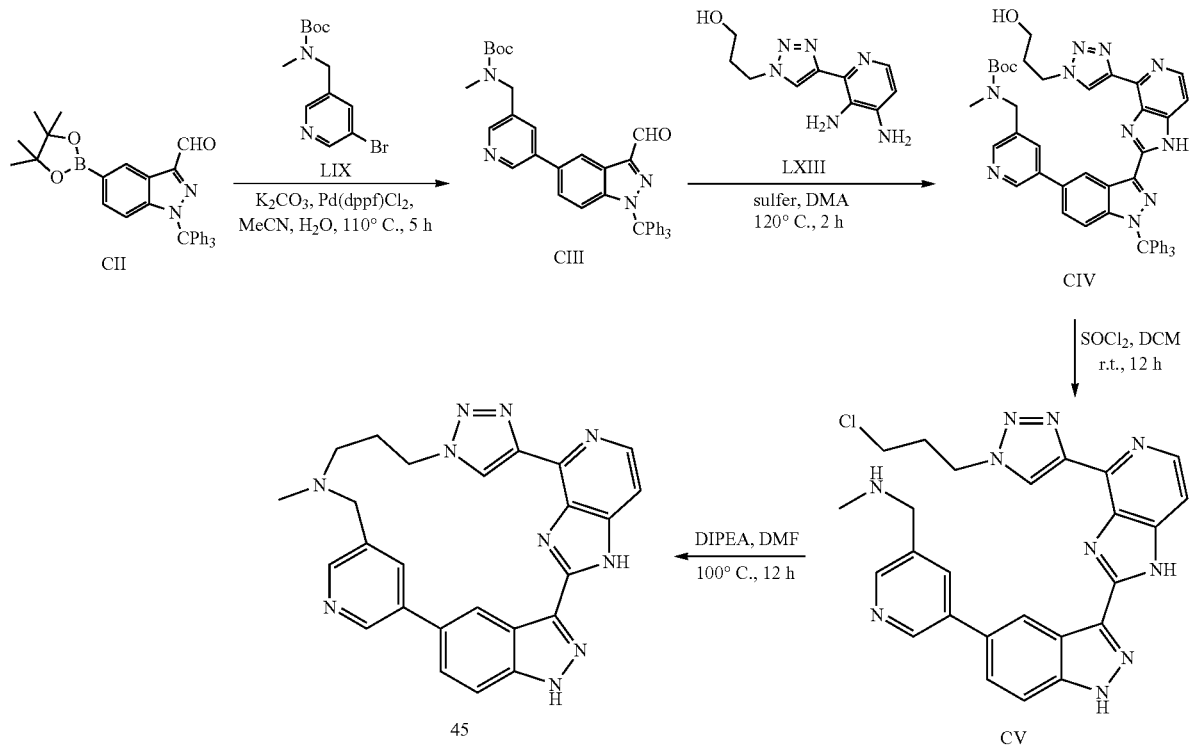

Step 1

A mixture of 5-(4,4,5,5-tetramethyl-1,3,2-dioxaborolan-2-yl)-1-trityl-1H-indazole-3-carbaldehyde (CII) (76.43 mL, 3.01 mmol), Pd(dppf)Cl$_2$ (245.4 mg, 0.30 mmol), a 2 M aqueous solution of K$_2$CO$_3$ (3.01 mL, 6.01 mmol), and tert-butyl ((5-bromopyridin-3-yl)methyl)(methyl)carbamate (LIX) (1.0 g, 3.31 mmol) in MeCN (20 mL) in a sealed vial was purged with N$_2$ gas for 10 min and then was heated to 110° C. for 5 h. The reaction mixture was concentrated, the residue was purified by column chromatography (0-100% EtOAc/hexanes) to obtain tert-butyl ((5-(3-formyl-1-trityl-1H-indazol-5-yl)pyridin-3-yl)methyl)(methyl)carbamate (CIII) (1.76 g, 2.89 mmol, 96.1% yield) as an orange solid. ESIMS found for C$_{39}$H$_{36}$N$_4$O$_3$ m/z 609.3 (M+H).

Step 2

A mixture of tert-butyl ((5-(3-formyl-1-trityl-1H-indazol-5-yl)pyridin-3-yl)methyl)(methyl)carbamate (CIII) (520 mg, 0.850 mmol), sulfur (27.4 mg, 0.85 mmol), and 3-(4-(3,4-diaminopyridin-2-yl)-1H-1,2,3-triazol-1-yl)propan-1-ol (LXIII) (200 mg, 0.850 mmol) in DMA (2 mL) was heated at 120° C. for 2 h. The reaction mixture was cooled and concentrated and the residue was adsorbed on silica gel, purified by column chromatography (0-100% EtOAc/hexanes) to obtain tert-butyl ((5-(3-(4-(1-(3-hydroxypropyl)-1H-1,2,3-triazol-4-yl)-1H-imidazo[4,5-c]pyridin-2-yl)-1-trityl-1H-indazol-5-yl)pyridin-3-yl)methyl)(methyl)carbamate (CIV) (490 mg, 0.595 mmol, 69.7% yield) as a brown solid. $^1$H NMR (499 MHz, DMSO-d$_6$) δ ppm 1.35 (9H, br s), 2.02 (2H, quin, J=6.59 Hz), 2.81 (3H, s), 3.41-3.45 (2H, m), 4.49 (2H, br d, J=4.12 Hz), 4.59 (2H, t, J=7.14 Hz), 6.60 (1H, d, J=9.06 Hz), 7.32-7.37 (9H, m), 7.39 (6H, br d, J=7.14 Hz), 7.52 (1H, d, J=5.21 Hz), 7.97 (1H, br s), 8.41 (1H, d, J=5.49 Hz), 8.47 (1H, d, J=1.65 Hz), 8.80-8.86 (1H, m), 8.97 (2H, br s), 9.14 (1H, s), 13.12 (1H, s); ESIMS found for C$_{49}$H$_{46}$N$_{10}$O$_3$ m/z 823.4 (M+1).

Step 3

To a stirred solution of tert-butyl ((5-(3-(4-(1-(3-hydroxypropyl)-1H-1,2,3-triazol-4-yl)-1H-imidazo[4,5-c]pyridin-2-yl)-1-trityl-1H-indazol-5-yl)pyridin-3-yl)methyl) (methyl) carbamate (CIV) (300 mg, 0.360 mmol) in DCM (2 mL) was added thionyl chloride (0.26 mL, 3.65 mmol) and the mixture was stirred for 12 h at room temperature. The solvent was evaporated and the residue was adsorbed on silica gel purified by column chromatography (0-20% 7N—NH$_3$-MeOH/CHCl$_3$). Pure fractions were concentrated and the resulting solids were triturated with DCM/hexanes, filtered and dried under high vacuum to obtain 1-(5-(3-(4-(1-(3-chloropropyl)-1H-1,2,3-triazol-4-yl)-1H-imidazo[4,5-c]pyridin-2-yl)-1H-indazol-5-yl)pyridin-3-yl)-N-methylmethanamine (CV) (45 mg, 0.090 mmol, 24.7% yield) as a beige solid. $^1$H NMR (499 MHz, DMSO-d$_6$) δ ppm 2.35 (3H, s), 2.37-2.44 (2H, m), 3.69 (2H, t, J=6.31 Hz), 3.83 (2H, s), 4.70 (2H, t, J=6.86 Hz), 7.51 (1H, br s), 7.82-7.91 (2H, m), 8.17 (1H, br s), 8.41 (1H, d, J=5.21 Hz), 8.56 (1H, d, J=1.92 Hz), 8.93 (1H, br s), 8.97 (1H, br s), 9.24 (1H, br s); ESIMS found for C$_{25}$H$_{23}$ClN$_{10}$ m/z 499.2 (M+1).

Step 4

A solution of 1-(5-(3-(4-(1-(3-chloropropyl)-1H-1,2,3-triazol-4-yl)-1H-imidazo[4,5-c]pyridin-2-yl)-1H-indazol-5-yl)pyridin-3-yl)-N-methylmethanamine (CV) (27 mg, 0.05 mmol) and DIPEA (0.02 mL, 0.11 mmol) in DMF (3 mL) was stirred at 100° C. for 12 h. The reaction mixture was concentrated and the residue was triturated with methanol. The solid was filtered and washed with saturated sodium bicarbonate solution, water, MeOH, and dried under high vacuum to obtain (1$^4$Z,2$^1$Z)-6-Methyl-1H,2$^3$H,3$^1$H-6-aza-2(7,2)-imidazo[4,5-c]pyridina-3(3,5)-indazola-4(3,5)- pyridina-1(4,1)-triazolacyclononaphane 45 (18.0 mg, 0.039 mmol, 71.9% yield) as a beige solid. $^1$H NMR (499 MHz, DMSO-$d_6$) δ ppm 2.18-2.25 (2H, m), 2.27 (3H, s), 2.55 (2H, br t, J=6.72 Hz), 3.64 (2H, s), 4.57 (2H, t, J=7.41 Hz), 7.49 (1H, d, J=5.21 Hz), 7.83 (1H, d, J=8.78 Hz), 8.07 (1H, dd, J=8.78, 1.65 Hz), 8.38 (1H, s), 8.41 (1H, d, J=5.21 Hz), 8.49 (1H, d, J=1.92 Hz), 9.00 (1H, d, J=2.20 Hz), 9.02 (1H, s), 9.33 (1H, s), 13.64 (1H, br s), 13.93 (1H, br s); ESIMS found for $C_{25}H_{22}N_{10}$ m/z 463.25 (M+1).

Example 4

Preparation of (Z)-5,10-Dimethyl-1H,2$^1$H-5,10-diaza-1(2,4)-imidazo[4,5-c]pyridina-2(3,5)-indazola-3(3,5)-pyridinacyclodecaphane (51) is depicted below in Scheme 20.

heated to 120° C. for 5 h. The reaction was concentrated to dryness and the residue was absorbed on silica, then purified by flash column chromatography (0-50% 7N—NH$_3$-MeOH/CHCl$_3$). The desired fractions were concentrated to dryness in vacuo and dried under high vacuo to obtain tert-butyl (4-((2-(5-(5-(hydroxymethyl)pyridin-3-yl)-1-trityl-1H-indazol-3-yl)-1H-imidazo[4,5-c]pyridin-4-yl)(methyl)amino)butyl)(methyl)carbamate (CVIII) (356 mg, 0.446 mmol, 47.0% yield) as a beige solid. ESIMS found for $C_{49}H_{50}N_8O_3$ m/z 799.4 (M+H).

Step 3

To a stirred solution of tert-butyl (4-((2-(5-(5-(hydroxymethyl)pyridin-3-yl)-1-trityl-1H-indazol-3-yl)-1H-imidazo[4,5-c]pyridin-4-yl)(methyl)amino)butyl)(methyl)carbamate (CVIII) (350 mg, 0.440 mmol) in DCM (2 mL) was added

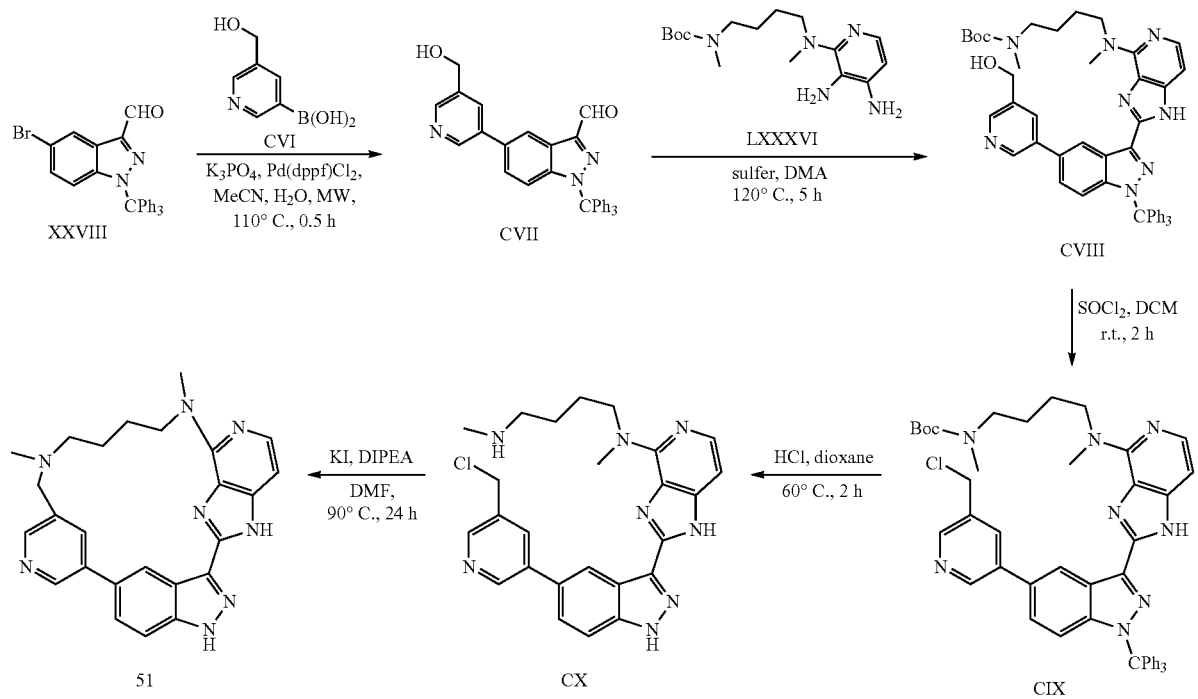

Scheme 20

Step 1

A solution of (5-(hydroxymethyl)pyridin-3-yl)boronic acid (CVI) (750 mg, 4.9 mmol), 5-bromo-1-trityl-1H-indazole-3-carbaldehyde (XXVIII) (1.53 g, 3.27 mmol), Pd(dppf)Cl$_2$ (134 mg, 0.160 mmol), and a 2 M aqueous solution of K$_3$PO$_4$ (4.9 mL, 9.81 mmol) in MeCN (15 mL) was purged with N$_2$ gas for 10 min and then was heated in microwave at 110° C. for 30 min. The organic layer was separated and concentrated and the residue was adsorbed on silica gel and purified by chromatography (25-100% EtOAc/hexanes) to obtain 5-(5-(hydroxymethyl)pyridin-3-yl)-1-trityl-1H-indazole-3-carbaldehyde (CVII) (400 mg, 0.807 mmol, 24.7% yield) as brown solids. ESIMS found for $C_{33}H_{25}N_3O_2$ m/z 496.2 (M+H).

Step 2

A solution of 5-(5-(hydroxymethyl)pyridin-3-yl)-1-trityl-1H-indazole-3-carbaldehyde (CVII) (470 mg, 0.950 mmol), tert-butyl (4-((3,4-diaminopyridin-2-yl)(methyl)amino)butyl)(methyl)carbamate (LXXXVI) (307 mg, 0.950 mmol) and sulfur (61 mg, 1.9 mmol) in DMA (4 mL) and was thionyl chloride (0.06 mL, 0.880 mmol) at 25° C. and the mixture was stirred for 2 h. The solvents were concentrated and dried under high vacuo to obtain tert-butyl (4-((2-(5-(5-(chloromethyl)pyridin-3-yl)-1-trityl-1H-indazol-3-yl)-1H-imidazo[4,5-c]pyridin-4-yl)(methyl)amino)butyl)(methyl)carbamate (CIX) (390 mg, 0.477 mmol, 108.9% yield) as beige solids which was used for next step without purification. ESIMS found for $C_{49}H_{49}ClN_8O_2$ m/z 817.4 (M+1).

Step 4

To a stirred suspension of tert-butyl (4-((2-(5-(5-(chloromethyl)pyridin-3-yl)-1-trityl-1H-indazol-3-yl)-1H-imidazo[4,5-c]pyridin-4-yl)(methyl) amino)butyl)(methyl)carbamate (CIX) (327 mg, 0.400 mmol) in dioxane (2 mL) was added a 4 M solution of HCl (0.5 mL, 2 mmol) in dioxane and the mixture was heated to 60° C. for 2 h. The solvent was concentrated, triturated with TEA and dried under high vacuo to obtain crude Ni-(2-(5-(5-(chloromethyl)pyridin-3-yl)-1H-indazol-3-yl)-1H-imidazo[4,5-c]pyridin-4-yl)-N$^1$,N$^4$-dimethylbutane-1,4-diamine (CX) (241 mg, 0.509 mmol) as a beige solid which was used for next step without purification. ESIMS found for $C_{25}H_{26}ClN_8$ m/z 474.2 (M+1).

Step 5

A mixture of crude Ni-(2-(5-(5-(chloromethyl)pyridin-3-yl)-1H-indazol-3-yl)-1H-imidazo[4,5-c]pyridin-4-yl)-$N^1$, $N^4$-dimethylbutane-1,4-diamine (CX) (241 mg, 0.509 mmol), KI (6.6 mg, 0.040 mmol) and DIPEA (0.42 mL, 2.4 mmol) in DMF (12 mL) was heated to 90° C. for 24 h. The solvent was removed under high vacuum and the residue was suspended in CHCl$_3$, sonicated and the solid were collected by filtration. The solid were then purified by preparative TLC (15% 7N—NH$_3$-MeOH/CHCl$_3$) to obtain (Z)-5,10-Dimethyl-1$^1$H,2$^1$H-5,10-diaza-1(2,4)-imidazo[4,5-c]pyridina-2(3,5)-indazola-3(3,5)-pyridinacyclodecaphane 51 (17.0 mg, 0.039 mmol, 9.7% yield) as a beige solid. $^1$H NMR (499 MHz, DMSO-d$_6$) δ ppm 1.74-1.84 (2H, m), 1.89-2.00 (2H, m), 2.35 (2H, br t, J=7.14 Hz), 2.40 (3H, s), 3.10 (3H, s), 3.74 (2H, s), 4.18 (2H, br t, J=7.00 Hz), 6.78 (1H, d, J=5.49 Hz), 7.75-7.81 (2H, m), 7.91 (1H, dd, J=8.78, 1.65 Hz), 8.15 (1H, s), 8.43 (1H, d, J=1.92 Hz), 8.67 (1H, s), 8.81 (1H, d, J=2.20 Hz), 13.11 (1H, br s), 13.71 (1H, br s); ESIMS found for $C_{25}H_{26}N_8$ m/z 439.2 (M+1).

Example 5

Preparation (Z)-2$^1$H,3$^1$H-8-Oxa-2(5,3),3(2,4)-diindazola-1(3,5)-pyridina-4(1,3)-benzenacyclooctaphane (57) is depicted below in Scheme 21.

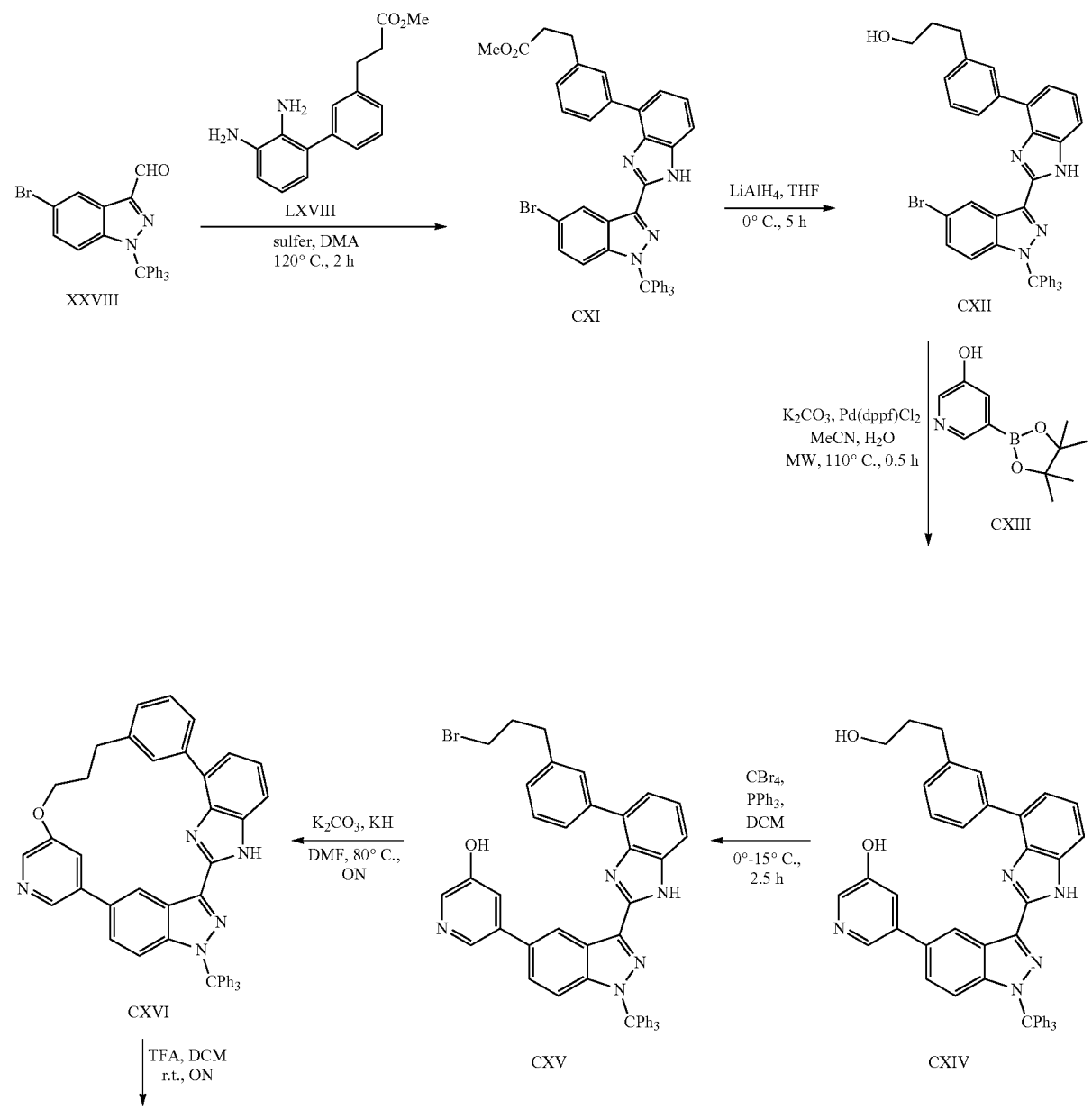

Scheme 21

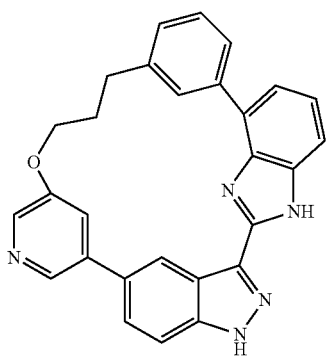

57

Step 1

A mixture of 5-bromo-1-trityl-1H-indazole-3-carbaldehyde (XXVIII) (750 mg, 1.6 mmol), sulfur (52 mg, 1.6 mmol), and methyl 3-(2',3'-diamino-[1,1'-biphenyl]-3-yl)propanoate (LXVIII) (0.48 g, 1.77 mmol) in DMA (2 mL) was heated at 120° C. for 2 h. The reaction mixture was cooled and concentrated and the residue was adsorbed on silica gel and purified by column chromatography (0-100% EtOAc/hexanes) to obtain methyl 3-(3-(2-(5-bromo-1-trityl-1H-indazol-3-yl)-1H-benzo[d]imidazol-4-yl)phenyl)propanoate (CXI) (1.1 g, 1.53 mmol, 95.5% yield) as a brown solid. ESIMS found for $C_{43}H_{33}BrN_4O_2$ m/z 717.2 ($^{79}$BrM+H).

Step 2

To a stirred and cooled 0° C. suspension of LiAlH$_4$ (40 mg, 1.06 mmol) in THF (10 mL) was added methyl 3-(3-(2-(5-bromo-1-trityl-1H-indazol-3-yl)-1H-benzo[d]imidazol-4-yl)phenyl) propanoate (CXI) (380 mg, 0.530 mmol) in THF (10 mL) dropwise. Reaction mixture was stirred for 5 h at 0° C. The reaction mixture was quenched with an aqueous saturated Na$_2$SO$_4$ solution at 0° C., diluted with water and extracted with EtOAc, concentrated and purified by column chromatography (0-100% EtOAc/hexanes) to obtain 3-(3-(2-(5-bromo-1-trityl-1H-indazol-3-yl)-1H-benzo[d]imidazol-4-yl)phenyl)propan-1-ol (CXII) (310 mg, 0.450 mmol, 84.9% yield) as a beige solid. $^1$H NMR (499 MHz, DMSO-d$_6$) δ ppm 1.82-1.90 (2H, m), 2.77-2.83 (2H, m), 3.47-3.52 (2H, m), 4.45 (1H, t, J=5.21 Hz), 6.42 (1H, d, J=9.06 Hz), 7.29-7.35 (11H, m), 7.35-7.40 (7H, m), 7.43 (1H, t, J=7.68 Hz), 7.46-7.51 (1H, m), 7.54 (1H, dd, J=7.96, 0.82 Hz), 7.90 (1H, d, J=7.96 Hz), 8.26 (1H, s), 8.82 (1H, d, J=1.92 Hz), 12.75 (1H, s); ESIMS found for $C_{42}H_{33}BrN_4O$ m/z 689.2 (M+1).

Step 3

A mixture of 3-(3-(2-(5-bromo-1-trityl-1H-indazol-3-yl)-1H-benzo[d]imidazol-4-yl)phenyl)propan-1-ol (CXII) (240 mg, 0.350 mmol), 5-(4,4,5,5-tetramethyl-1,3,2-dioxaborolan-2-yl)pyridin-3-ol (CXIII) (115 mg, 0.520 mmol, 1 ClickChemistry Inc.), Pd(dppf)Cl$_2$ (27 mg, 0.030 mmol) and a 2 M aqueous solution of K$_2$CO$_3$ (0.22 mL, 0.660 mmol) in MeCN (5 mL) was purged with N$_2$ gas for 10 min and then was heated to 110° C. for 30 min in microwave. The organic layer was carefully separated, and concentrated, absorbed on silica gel and purified by flash column chromatography (0-10% 7N NH$_3$ in MeOH/CHCl$_3$). The pure fractions were combined, concentrated and the residue was triturated from DCM/hexanes. The solid was collected by filtration and dried under high vacuum to obtain 5-(3-(4-(3-(3-hydroxypropyl)phenyl)-1H-benzo[d]imidazol-2-yl)-1-trityl-1H-indazol-5-yl)pyridin-3-ol (CXIV) (170 mg, 0.242 mmol, 69.4% yield) as a beige solid. $^1$H NMR (499 MHz, DMSO-d$_6$) δ ppm 1.68-1.75 (2H, m), 2.65-2.70 (2H, m), 3.28-3.31 (2H, m), 4.44 (1H, br s), 6.56 (1H, d, J=9.06 Hz), 7.21 (1H, d, J=7.41 Hz), 7.31-7.37 (10H, m), 7.37-7.42 (7H, m), 7.47 (1H, d, J=7.96 Hz), 7.48-7.51 (2H, m), 7.55 (1H, d, J=7.96 Hz), 8.08 (1H, s), 8.15-8.19 (2H, m), 8.37 (1H, d, J=1.92 Hz), 8.95 (1H, d, J=1.37 Hz), 10.07 (1H, br d, J=1.10 Hz), 12.74 (1H, br s); ESIMS found for $C_{47}H_{37}N_5O_2$ m/z 704.3 (M+1).

Step 4

To a solution of 5-(3-(4-(3-(3-hydroxypropyl)phenyl)-1H-benzo[d]imidazol-2-yl)-1-trityl-1H-indazol-5-yl)pyridin-3-ol (CXIV) (100 mg, 0.140 mmol) and carbon tetrabromide (141 mg, 0.430 mmol) in DCM (3 mL) at 0° C. was added triphenylphosphine (75 mg, 0.280 mmol). The reaction mixture was stirred at 0° C. for 1 h then at room temperature for 1.5 h, diluted with DCM, washed with water, dried (MgSO$_4$), filtered and evaporated under vacuum. The residue was purified by chromatography (0-100% EtOAc/hexanes) to give 5-(3-(4-(3-(3-bromopropyl)phenyl)-1H-benzo[d]imidazol-2-yl)-1-trityl-1H-indazol-5-yl)pyridin-3-ol (CXV) (85 mg, 0.111 mmol, 78.0% yield) as a beige solid. $^1$H NMR (499 MHz, DMSO-d$_6$) δ ppm 2.01-2.13 (2H, m), 2.73-2.81 (2H, m), 3.37 (2H, t, J=6.59 Hz), 6.56 (1H, d, J=9.06 Hz), 7.24 (1H, d, J=7.68 Hz), 7.32-7.42 (17H, m), 7.48-7.52 (3H, m), 7.56 (1H, dd, J=7.82, 0.96 Hz), 8.15 (1H, s), 8.15-8.20 (2H, m), 8.37 (1H, d, J=1.92 Hz), 8.93 (1H, d, J=1.10 Hz), 10.07 (1H, s), 12.75 (1H, s); ESIMS found for $C_{47}H_{36}BrN_5O$ m/z 766.2 (M+1).

Step 5

A mixture of 5-(3-(4-(3-(3-bromopropyl)phenyl)-1H-benzo[d]imidazol-2-yl)-1-trityl-1H-indazol-5-yl)pyridin-3-ol (CXV) (33 mg, 0.040 mmol) and K$_2$CO$_3$ (12 mg, 0.090 mmol) in DMF (2 mL) was stirred overnight at 80° C. The reaction mixture was diluted with water and extracted with EtOAc, the combined organic layers were washed with brine and concentrated. The residue was adsorbed on silica gel and purified by column chromatography (0-100% EtOAc/hexanes) to obtain (Z)-trityl-2$^1$H,3$^1$H-8-oxa-2(5,3),3(2,4)-diindazola-1(3,5)-pyridina-4(1,3)-benzenacyclooctaphane (CXVI) (15 mg, 0.022 mmol, 50.8% yield) as a white solid. $^1$H NMR (499 MHz, DMSO-d$_6$) δ ppm 2.04-2.15 (2H, m), 2.72-2.81 (2H, m), 4.41-4.50 (2H, m), 6.59 (1H, d, J=9.06 Hz), 7.27 (1H, d, J=7.68 Hz), 7.30-7.47 (18H, m), 7.54 (1H, dd, J=8.92, 1.78 Hz), 7.56-7.61 (2H, m), 7.77-7.83 (1H, m), 8.22 (1H, d, J=2.74 Hz), 8.31 (1H, d, J=1.65 Hz), 8.51 (1H, s), 8.73 (1H, d, J=1.37 Hz), 12.56 (1H, s); ESIMS found for $C_{47}H_{35}N_5O$ m/z 686.3 (M+1).

Step 6

To a solution of (Z)-trityl-$2^1$H,$3^1$H-8-oxa-2(5,3),3(2,4)-diindazola-1(3,5)-pyridina-4(1,3)-benzenacyclooctaphane (CXVI) (12 mg, 0.020 mmol) in DCM (0.50 mL) was added TFA (0.07 mL, 0.870 mmol) and the mixture was stirred overnight at room temperature. The solvent was evaporated and the residue was adsorbed on silica gel and purified by column chromatography (0-10% 7N $NH_3$-MeOH/$CHCl_3$). Pure fractions were concentrated and the solid was triturated with DCM/hexanes, filtered and dried to obtain (Z)-$2^1$H, $3^1$H-8-Oxa-2(5,3),3(2,4)-diindazola-1(3,5)-pyridina-4(1,3)-benzenacyclooctaphane 57 (6.0 mg, 0.014 mmol, 77.3% yield) as a white solid. $^1$H NMR (499 MHz, DMSO-$d_6$) δ ppm 2.08-2.18 (2H, m), 2.72-2.81 (2H, m), 4.46-4.55 (2H, m), 7.28 (1H, d, J=7.68 Hz), 7.30-7.34 (1H, m), 7.36-7.39 (1H, m), 7.43 (1H, t, J=7.55 Hz), 7.52 (1H, dd, J=7.68, 1.10 Hz), 7.56 (1H, d, J=7.68 Hz), 7.78-7.82 (1H, m), 7.84-7.86 (1H, m), 7.86-7.89 (1H, m), 8.24 (1H, d, J=2.74 Hz), 8.43 (1H, d, J=1.37 Hz), 8.52 (1H, s), 8.71 (1H, s), 13.18 (1H, br s), 13.83 (1H, br s); ESIMS found for $C_{28}H_{21}N_5O$ m/z 444.2 (M+1).

Example 6

Preparation (Z)-$2^1$H,$3^1$H-5-oxa-8-aza-2(5,3),3(2,4)-diindazola-1(2,6)-pyrazina-4(1,3)-benzenacyclooctaphane (109) is depicted below in Scheme 22.

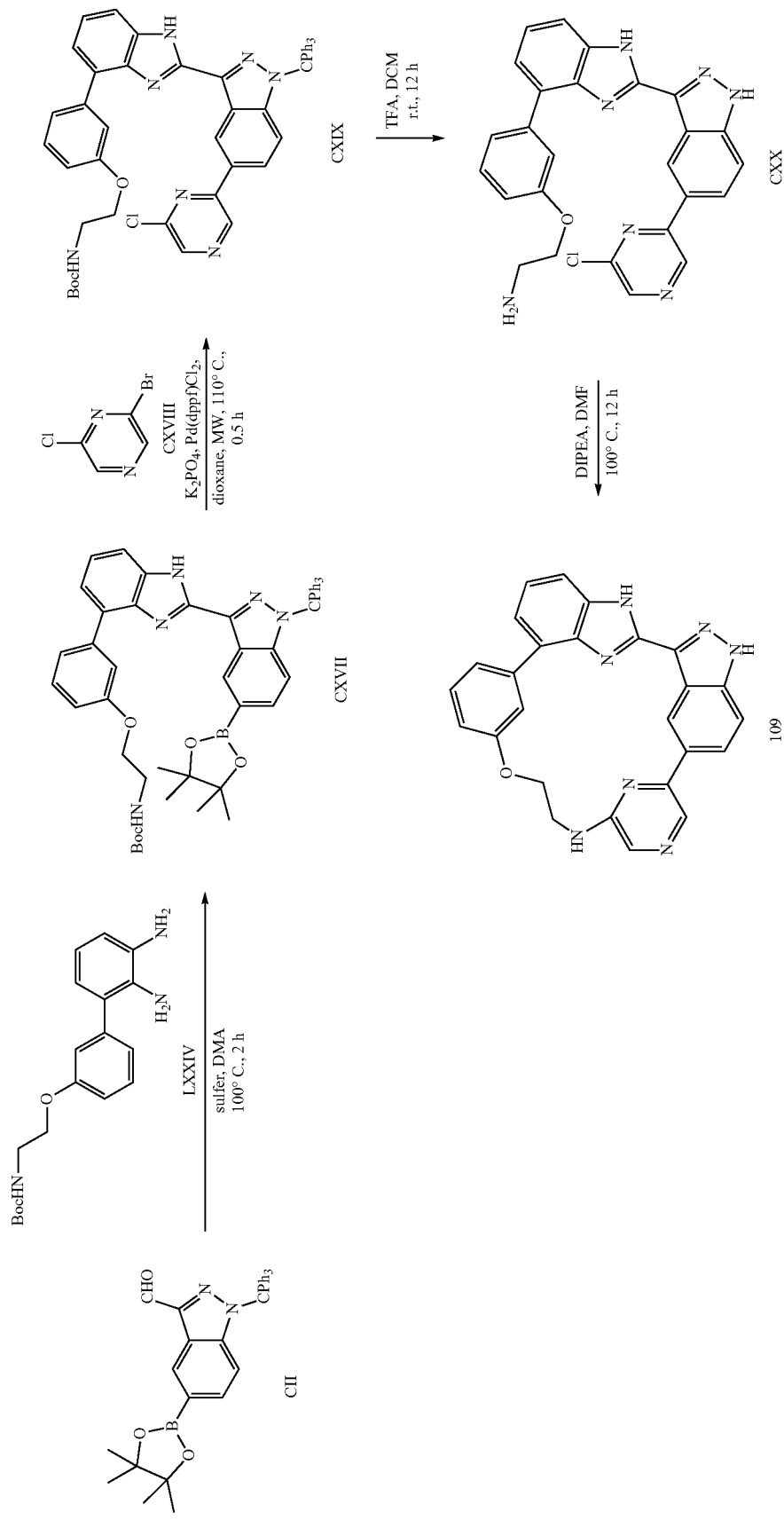

Step 1

A mixture of tert-butyl (2-((2',3'-diamino-[1,1'-biphenyl]-3-yl)oxy)ethyl)carbamate (LXXIV) (450. mg, 1.31 mmol), sulfur (80 mg, 2.5 mmol), and 5-(4,4,5,5-tetramethyl-1,3,2-dioxaborolan-2-yl)-1-trityl-1H-indazole-3-carbaldehyde (CII) (800 mg, 1.56 mmol) in DMF (2 mL) was heated at 100° C. for 2 h. The reaction mixture was cooled and concentrated and the residue was adsorbed on silica gel, purified by column chromatography (0-100% EtOAc/hexanes) to obtain tert-butyl (2-(3-(2-(5-(4,4,5,5-tetramethyl-1,3,2-dioxaborolan-2-yl)-1-trityl-1H-indazol-3-yl)-1H-benzo[d]imidazol-4-yl)phenoxy)ethyl)carbamate (CXVII) (680 mg, 0.81 mmol, 61.9% yield) as a beige solid. ESIMS found for $C_{52}H_{52}BN_5O_5$ m/z 838.25 (M+H).

Step 2

A mixture of tert-butyl (2-(3-(2-(5-(4,4,5,5-tetramethyl-1,3,2-dioxaborolan-2-yl)-1-trityl-1H-indazol-3-yl)-1H-benzo[d]imidazol-4-yl)phenoxy)ethyl)carbamate (CXVII) (412 mg, 0.49 mmol), Pd(dppf)Cl$_2$ (20 mg, 0.02 mmol), a 2 M aqueous solution of K$_3$PO$_4$ (0.7 mL, 1.4 mmol), and 2-bromo-6-chloropyrazine (CXVIII) (190 mg, 0.98 mmol) in dioxane (10 mL) in a sealed vial was purged with N$_2$ gas for 10 min and irradiated with microwave at 110° C. for 30 minutes. The organic layer was separated and concentrated, the residue was purified by column chromatography (0-2% MeOH/CHCl$_3$) to obtain tert-butyl (2-(3-(2-(5-(6-chloropyrazin-2-yl)-1-trityl-1H-indazol-3-yl)-1H-benzo[d]imidazol-4-yl)phenoxy)ethyl)carbamate (CXIX) (350 mg, 0.42 mmol, 86.3% yield) as a brown solid. $^1$H NMR (500 MHz, DMSO-d$_6$) δ ppm 1.31 (9H, s), 3.18-3.24 (2H, m), 4.05 (2H, brt, J=5.90 Hz), 6.59 (1H, d, J=9.33 Hz), 6.90 (1H, brt, J=5.21 Hz), 7.00 (1H, dd, J=8.10, 2.06 Hz), 7.31-7.37 (9H, m), 7.37-7.43 (6H, m), 7.48-7.55 (2H, m), 7.58 (1H, dd, J=7.96, 0.82 Hz), 7.82 (1H, s), 7.92 (1H, dd, J=9.19, 1.78 Hz), 7.97 (1H, br d, J=7.68 Hz), 8.74 (1H, s), 9.21 (1H, s), 9.42 (1H, d, J=1.10 Hz), 12.80 (1H, s); ESIMS found for $C_{50}H_{42}ClN_7O_3$ m/z 824.15 (M+1).

Step 3

To a stirred solution of tert-butyl (2-(3-(2-(5-(6-chloropyrazin-2-yl)-1-trityl-1H-indazol-3-yl)-1H-benzo[d]imidazol-4-yl)phenoxy)ethyl)carbamate (CXIX) (260 mg, 0.32 mmol) in DCM (2 mL) was added TFA (1.0 mL, 12.98 mmol) and the mixture was stirred for 12 h at room temperature. The solvent was evaporated and the residue was adsorbed on silica gel purified by column chromatography (0-5% 7N—NH$_3$-MeOH/CHCl$_3$). Pure fractions were concentrated and the resulting solids were triturated with MeOH, filtered and dried under high vacuum to obtain 2-(3-(2-(5-(6-chloropyrazin-2-yl)-1H-indazol-3-yl)-1H-benzo[d]imidazol-4-yl)phenoxy)ethan-1-amine (CXX) (90 mg, 0.178 mmol, 72.2% yield) as an off-white solid. $^1$H NMR (499 MHz, DMSO-d$_6$) δ ppm 2.79 (2H, br t, J=5.63 Hz), 4.02 (2H, t, J=5.90 Hz), 7.01 (1H, dd, J=8.23, 1.92 Hz), 7.30-7.39 (1H, m), 7.51 (2H, br t, J=7.96 Hz), 7.55 (1H, br d, J=7.41 Hz), 7.85 (1H, br s), 7.83 (1H, d, J=8.78 Hz), 7.96 (1H, br dd, J=5.21, 4.39 Hz), 8.25 (1H, dd, J=8.78, 1.65 Hz), 8.77 (1H, s), 9.29 (1H, s), 9.36 (1H, s); ESIMS found for $C_{26}H_{20}ClN_7O$ m/z 482. (M+1).

Step 4

A solution of 2-(3-(2-(5-(6-chloropyrazin-2-yl)-1H-indazol-3-yl)-1H-benzo[d]imidazol-4-yl)phenoxy)ethan-1-amine (CXX) (90 mg, 0.19 mmol) and DIPEA (0.07 mL, 0.41 mmol) in DMF (10 mL) was stirred at 110° C. for 12 h. The reaction mixture was concentrated and the residue was adsorbed on silica gel purified by column chromatography (0-5% MeOH/CHCl$_3$). The fractions were concentrated and the residue was triturated with 10% 7N—NH$_3$-MeOH/CHCl$_3$. The solid was filtered and dried under high vacuum to obtain (Z)-2$^1$H,3$^1$H-5-oxa-8-aza-2(5,3),3(2,4)-diindazola-1(2,6)-pyrazina-4(1,3)-benzenacyclooctaphane 109 (22.0 mg, 0.05 mmol, 26.4% yield) as a beige solid. $^1$H NMR (499 MHz, DMSO-d$_6$) δ ppm 3.67 (2H, q, J=4.48 Hz), 4.82 (2H, t, J=4.67 Hz), 6.94 (1H, ddd, J=8.23, 2.47, 0.82 Hz), 7.31 (1H, d, J=7.50 Hz), 7.33 (1H, t, J=7.70 Hz), 7.36-7.41 (1H, m), 7.43-7.46 (1H, m), 7.50-7.58 (2H, m), 7.74 (1H, d, J=8.23 Hz), 7.92 (1H, dd, J=8.64, 1.51 Hz), 7.96 (1H, s), 8.15 (1H, s), 8.35 (1H, d, J=2.20 Hz), 9.04 (1H, s), 13.22 (1H, br s), 13.80 (1H, br s); ESIMS found for $C_{26}H_{19}N_7O$ m/z 446.1 (M+1).

Example 7

Preparation 2$^1$H-4,10-diaza-2(5,3)-indazola-1,5(3,5)-dipyridina-6(1,3)-benzenacycloundecaphane-3,9-dione (97) is depicted below in Scheme 23.

Scheme 23

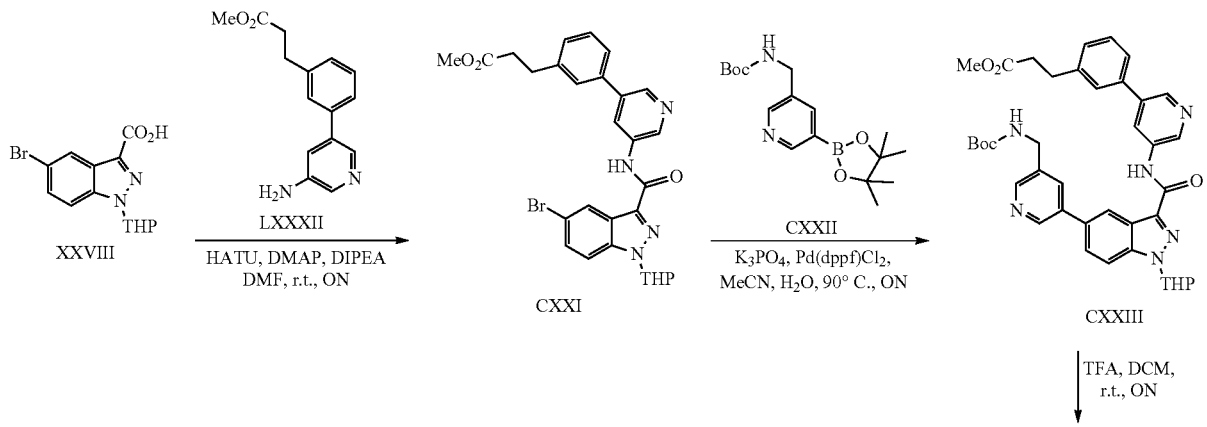

TFA, DCM, r.t., ON

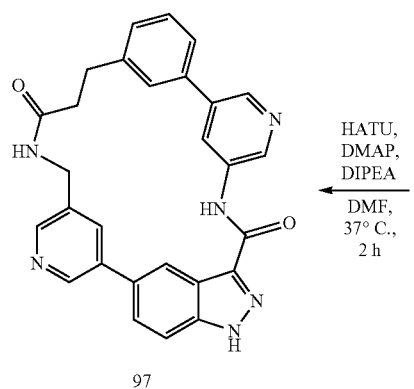

97

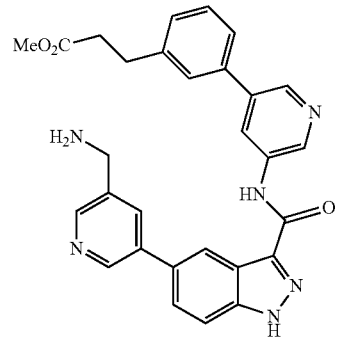

CXXV

CXXIV

Step 1

A solution of methyl 3-(3-(5-aminopyridin-3-yl)phenyl) propanoate (LXXXII) (350 mg, 1.37 mmol), 5-bromo-1-(tetrahydro-2H-pyran-2-yl)-1H-indazole-3-carboxylic acid (XXVIII) (444 mg, 1.37 mmol), HATU (571 mg, 1.5 mmol), DMAP (8.3 mg, 0.070 mmol) and DIPEA (0.48 mL, 2.73 mmol) in DMF (2 mL) was stirred overnight at room temperature. The reaction mixture was diluted with water and the precipitated solid was filtered and dried under vacuum to obtain methyl 3-(3-(5-(5-bromo-1-(tetrahydro-2H-pyran-2-yl)-1H-indazole-3-carboxamido)pyridin-3-yl) phenyl)propanoate (CXXI) (660 mg, 1.171 mmol, 85.8% yield) as a beige solid. ESIMS found for $C_{28}H_{27}BrN_4O_4$ m/z 563.2 ($^{79}$BrM+H).

Step 2

A mixture of 3-(3-(5-(5-bromo-1-(tetrahydro-2H-pyran-2-yl)-1H-indazole-3-carboxamido)pyridin-3-yl)phenyl)propanoate (CXXI) (188 mg, 0.330 mmol), tert-butyl ((5-(4,4,5,5-tetramethyl-1,3,2-dioxaborolan-2-yl)pyridin-3-yl) methyl)carbamate (CXXII) (169 mg, 0.670 mmol), Pd(dppf) $Cl_2$ (27 mg, 0.030 mmol) and a 2 M aqueous solution of $K_2CO_3$ (0.22 mL, 0.670 mmol) in MeCN (4 mL) was purged with $N_2$ gas for 10 min and then was heated to 90° C. overnight. The organic layer was carefully separated, and concentrated, absorbed on silica gel and purified by flash column chromatography (0-15% 7N $NH_3$ in MeOH/$CHCl_3$). The pure fractions were combined, concentrated and the residue was triturated from DCM/hexanes. The solid was collected by filtration and dried under high vacuum to obtain methyl 3-(3-(5-(5-(5-(((tert-butoxycarbonyl)amino)methyl) pyridin-3-yl)-1-(tetrahydro-2H-pyran-2-yl)-H-indazole-3-carboxamido)pyridin-3-yl)phenyl)propanoate (CXXIII) (177 mg, 0.256 mmol, 76.8% yield) as a brown solid. $^1$H NMR (500 MHz, DMSO-$d_6$) δ ppm 1.40 (9H, s), 1.66 (2H, br s), 1.79-1.89 (1H, m), 2.05-2.15 (2H, m), 2.58-2.66 (1H, m), 2.73 (2H, t, J=7.68 Hz), 2.96 (2H, t, J=7.68 Hz), 3.60 (3H, s), 3.86 (1H, td, J=10.98, 3.29 Hz), 3.98-4.03 (1H, m), 4.27 (2H, br d, J=6.04 Hz), 6.09 (1H, dd, J=10.02, 2.33 Hz), 7.32 (1H, d, J=7.41 Hz), 7.45 (1H, t, J=7.68 Hz), 7.52-7.59 (2H, m), 7.61 (1H, s), 7.91 (1H, dd, J=8.92, 1.78 Hz), 8.00 (1H, s), 8.06 (1H, d, J=8.23 Hz), 8.48 (1H, d, J=1.92 Hz), 8.52 (1H, s), 8.60 (1H, t, J=2.20 Hz), 8.64 (1H, d, J=1.92 Hz), 8.84 (1H, d, J=2.20 Hz), 9.11 (1H, d, J=2.20 Hz), 10.63 (1H, s); ESIMS found for $C_{39}H_{42}N_6O_6$ m/z 691.4 (M+1).

Step 3

To a stirred solution of methyl 3-(3-(5-(5-(5-(((tert-butoxycarbonyl)amino) methyl)pyridin-3-yl)-1-(tetrahydro-2H-pyran-2-yl)-H-indazole-3-carboxamido)pyridin-3-yl) phenyl)propanoate (CXXIII) (170 mg, 0.250 mmol) in DCM (2 mL) was added TFA (0.38 mL, 4.92 mmol) and the mixture was stirred overnight at room temperature. The solvent was evaporated and the residue was adsorbed on silica gel and purified by column chromatography (0→10% 7N $NH_3$ in MeOH/$CHCl_3$). The pure fractions were combined, concentrated and the residue was triturated from DCM/hexanes. The solid was collected by filtration and dried under high vacuum to obtain methyl 3-(3-(5-(5-(5-(aminomethyl)pyridin-3-yl)-1H-indazole-3-carboxamido) pyridin-3-yl)phenyl)propanoate (CXXIV) (90 mg, 0.178 mmol, 72.2% yield) as a beige solid. $^1$H NMR (500 MHz, DMSO-$d_6$) δ ppm 2.73 (2H, t, J=7.55 Hz), 2.96 (2H, t, J=7.68 Hz), 3.61 (3H, s), 3.85 (2H, s), 7.31 (1H, d, J=7.68 Hz), 7.45 (1H, t, J=7.68 Hz), 7.56 (1H, d, J=7.68 Hz), 7.60 (1H, s), 7.79-7.87 (2H, m), 8.11 (1H, t, J=2.06 Hz), 8.51-8.55 (2H, m), 8.61-8.66 (2H, m), 8.78 (1H, d, J=2.47 Hz), 9.10 (1H, d, J=2.20 Hz), 10.76 (1H, s); ESIMS found for $C_{29}H_{26}N_6O_3$ m/z 507.2 (M+1).

Step 4

A solution of obtain methyl 3-(3-(5-(5-(5-(aminomethyl) pyridin-3-yl)-1H-indazole-3-carboxamido)pyridin-3-yl) phenyl)propanoate (CXXIV) (85 mg, 0.170 mmol) and a 2 M aqueous solution of NaOH (0.17 mL, 0.340 mmol) in MeOH (2 mL) was heated to 50° C. for 5 h. The solvent was removed and the residue was diluted with water and acidified with 1N HCl. The precipitated solid was filtered and dried under vacuum to obtain 3-(3-(5-(5-(5-(aminomethyl) pyridin-3-yl)-1H-indazole-3-carboxamido)pyridin-3-yl) phenyl)propanoic acid (CXXV) (80 mg, 0.162 mmol, 96.8% yield) as a beige solid. $^1$H NMR (499 MHz, DMSO-$d_6$) δ ppm 2.63 (2H, t, J=7.68 Hz), 2.93 (2H, t, J=7.68 Hz), 4.20 (2H, q, J=5.49 Hz), 7.34 (1H, d, J=7.68 Hz), 7.46 (1H, t, J=7.68 Hz), 7.57 (1H, d, J=7.68 Hz), 7.62 (1H, s), 7.84-7.94 (2H, m), 8.41 (1H, s), 8.60 (3H, s), 8.66-8.74 (3H, m), 8.98 (1H, d, J=1.92 Hz), 9.17 (1H, d, J=1.92 Hz), 10.87 (1H, s), 11.96-12.40 (1H, m), 14.27 (1H, s); ESIMS found for $C_{28}H_{24}N_6O_3$ m/z 493.2 (M+1).

Step 5

A mixture of 3-(3-(5-(5-(5-(aminomethyl)pyridin-3-yl)-1H-indazole-3-carboxamido) pyridin-3-yl)phenyl)propanoic acid (CXXV) (50 mg, 0.100 mmol), HATU (58 mg, 0.150 mmol), DMAP (0.62 mg, 0.010 mmol) and DIPEA (0.05 mL, 0.300 mmol) in DMF (5 mL) was stirred for 2 h at 37° C. The solvent was concentrated, the residue was taken up in EtOAc (50 ml) and washed with saturated aqueous $NaHCO_3$, water and then with brine. The organic layer was then separated and dried ($MgSO_4$) before concentration to dryness. The crude product was then purified by flash column chromatography (0-10% MeOH/$CHCl_3$). The desired fractions were concentrated to dryness in vacuo to obtain 2¹H-4,10-diaza-2(5,3)-indazola-1,5(3,5)-dipyridina-6(1,3)-benzenacycloundecaphane-3,9-dione 97 (10.0 mg, 0.021 mmol, 20.8% yield) as an off-white solid. $^1$H NMR (499 MHz, DMSO-d$_6$) δ ppm 2.74-2.83 (2H, m), 2.95-3.03 (2H, m), 4.50 (2H, d, J=5.21 Hz), 7.30 (1H, d, J=7.68 Hz), 7.41 (1H, t, J=7.55 Hz), 7.70 (1H, d, J=7.68 Hz), 7.76-7.82 (2H, m), 8.00 (1H, dd, J=8.78, 1.65 Hz), 8.26 (1H, s), 8.43 (1H, t, J=5.35 Hz), 8.53 (1H, d, J=1.92 Hz), 8.70 (1H, s), 8.74 (1H, d, J=1.92 Hz), 8.79-8.83 (1H, m), 8.85 (1H, d, J=1.92 Hz), 8.95 (1H, d, J=1.92 Hz), 10.84 (1H, s), 13.88 (1H, s); ESIMS found for $C_{28}H_{22}N_6O_2$ m/z 475.2 (M+1).

Example 7

The screening assay for Wnt activity is described as follows. Reporter cell lines can be generated by stably transducing cancer cell lines (e.g., colon cancer) or primary cells (e.g., IEC-6 intestinal cells) with a lentiviral construct that includes a Wnt-responsive promoter driving expression of the firefly luciferase gene.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 μg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%. For Sp5-Luc reporter gene assays, the cells were plated at 4,000 cells/well in 384-well plates with a DMEM medium containing 1% fetal bovine serum, and 1% Penicillin-Streptomycin and incubated for 36 to 48 hours at 37° C. and 5% CO$_2$. Following incubation, 15 μl of BriteLite Plus luminescence reagent (Perkin Elmer) was added to each well of the 384-well assay plates. The plates were placed on an orbital shaker for 2 min and then luminescence was quantified using the Envision (Perkin Elmer) plate reader. Readings were normalized to DMSO only treated cells, and normalized activities were utilized for EC$_{50}$ calculations using the dose-response log (inhibitor) vs. response-variable slope (four parameters) nonlinear regression feature available in GraphPad Prism 5.0 (or Dotmatics). For EC$_{50}$ of >10 μM, the percent inhibition at 10 M is provided.

Table 2 shows the measured activity for representative compounds of Formulas (I) and (II) as described herein.

TABLE 2

| Compound | EC$_{50}$ (μM) |
| --- | --- |
| 1 | 0.022 |
| 2 | 0.022 |
| 3 | 0.052 |
| 4 | 7.658 |
| 5 | 0.124 |
| 6 | 0.009 |
| 7 | 0.437 |
| 8 | 0.042 |
| 10 | 0.011 |
| 15 | 0.059 |

TABLE 2-continued

| Compound | EC$_{50}$ (μM) |
| --- | --- |
| 22 | 0.010 |
| 29 | 0.082 |
| 38 | 0.087 |
| 45 | 0.338 |
| 51 | 0.577 |
| 57 | 0.475 |
| 64 | >10 (47.4%) |
| 71 | 0.017 |
| 97 | >10 (22.2%) |
| 109 | 0.034 |

Example 8

Representative compounds were screened using the assay procedure for DYRK1A kinase activity as described below.

Each compound was dissolved in DMSO as a 10 mM stock and used to prepare compound source plates. Serial dilution (1:3, 11-point dose-response curves from 10 μM to 0.00016 μM) and compound transfer was performed using the ECHO 550 (Labcyte, Sunnyvale, Calif.) into 1536-well black-walled round bottom plates (Corning).

The DYRK1A kinase assay was run using the Ser/Thr 18 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as a ratio of coumarin emission/fluorescein emission.

Briefly, recombinant DYRK1A kinase, ATP and Ser/Thr peptide 18 were prepared in 1× Kinase buffer to final concentrations of 0.19 μg/mL, 30 μM, and 4 μM respectively. The mixture was allowed to incubate with the representative compounds for one hour at room temperature. All reactions were performed in duplicate. Unphosphorylated ("0% Control") and phosphorylated ("100% control") forms of Ser/Thr 18 served as control reactions. Additionally, an 11-point dose-response curve of Staurosporine (1 uM top) was run to serve as a positive compound control.

After incubation, Development Reagent A was diluted in Development Buffer then added to the reaction and allowed to further incubate for one hour at room temperature. The plate was read at Ex 400 Em 455 to detect the coumarin signal and Ex 400 Em 520 to measure the signal (EnVision Multilabel Plate Reader, PerkinElmer).

The Emission ratio (Em) was calculated as a ratio of the coumarin (C) emission signal (at 445 nm)/Fluorescein (F) emission signal (at 520 nm). The percent phosphorylation was then calculated using the following formula: [1−((Em ratio×F100%)−C100%)/((C0%−C100%)+(Em ratio× (F100%−F0%)))]. Dose-response curves were generated and inhibitory concentration (IC$_{50}$) values were calculated using non-linear regression curve fit in the Dotmatics' Studies Software (Bishops Stortford, UK).

Table 3 shows the measured activity for representative compounds of Formulas (I) and (II) as described herein.

TABLE 3

| Compound | EC$_{50}$ (μM) |
| --- | --- |
| 1 | 0.266 |
| 2 | 0.006 |
| 3 | 0.010 |
| 4 | 0.204 |

TABLE 3-continued

| Compound | EC$_{50}$ (µM) |
|---|---|
| 5 | 0.709 |
| 6 | 0.096 |
| 7 | >10 |
| 8 | 0.003 |
| 10 | 0.018 |
| 15 | 0.111 |
| 22 | 0.068 |
| 29 | 0.412 |
| 38 | 0.005 |
| 45 | 0.004 |
| 51 | 0.002 |
| 57 | >10 |
| 64 | 0.448 |
| 71 | 0.014 |
| 97 | 0.009 |
| 109 | 0.096 |

TABLE 4

| Compound | EC$_{50}$ (µM) |
|---|---|
| 1 | 0.007 |
| 2 | 0.001 |
| 3 | 0.001 |
| 4 | 0.494 |
| 5 | 0.048 |
| 6 | 0.004 |
| 7 | >10 |
| 8 | 0.001 |
| 10 | 0.004 |
| 15 | 0.010 |
| 22 | 0.011 |
| 29 | 0.015 |
| 38 | 0.001 |
| 45 | 0.001 |
| 51 | 0.002 |
| 57 | 1.866 |
| 64 | 0.088 |
| 71 | 0.014 |
| 97 | 0.010 |
| 109 | 0.062 |

Example 9

Representative compounds were screened using the assay procedure for GSK3β kinase activity as described below.

Each compound is dissolved in DMSO as a 10 mM stock and used to prepare compound source plates. Serial dilution (1:3, 11-point dose-response curves from 10 µM to 0.0003 µM) and compound transfer was performed using the ECHO 550 (Labcyte, Sunnyvale, Calif.) into 1536-well black-walled round bottom plates (Corning).

The GSK3β kinase assay is run using the Ser/Thr 09 peptide Z-lyte assay kit according to manufacturer's instructions (Life Technologies—a Division of Thermo-Fisher). This is a non-radioactive assay using fluorescence resonance energy transfer (FRET) between coumarin and fluorescein to detect kinase activity which is represented as ratio of coumarin emission/fluorescein emission.

Briefly, recombinant GSK3β kinase, ATP and Ser/Thr peptide 09 are prepared in 1× Kinase buffer to final concentrations of 0.04 µg/mL, 46 µM, and 4 µM respectively. The mixture is allowed to incubate with the representative compounds for one hour at room temperature. All reactions were performed in duplicate. Unphosphorylated ("0% Control") and phosphorylated ("100% control") forms of Ser/Thr 18 serve as control reactions.

After incubation, diluted Development Buffer is added to the reaction and allowed to further incubate for one hour at room temperature. The plate is read at Ex 400 Em 455 to detect the coumarin signal and Ex 400 Em 520 to measure the signal (EnVision Multilabel Plate Reader, PerkinElmer).

The Emission ratio (Em) is calculated as a ratio of the coumarin (C) emission signal (at 445 nm)/Fluorescein (F) emission signal (at 520 nm). The percent phosphorylation is then calculated using the following formula: [1−((Em ratio× F100%)−C100%)/((C0%−C100%)+(Em ratio×(F100%−F0%)))].

Dose-response curves are generated and inhibitory concentration (IC$_{50}$) values are calculated using non-linear regression curve fit in the Dotmatics' Studies Software (Bishops Stortford, UK).

Table 4 shows the activity of representative compounds of Formulas (I) and (II) as provided herein.

Example 10

Representative compounds were screened using the assay procedure to assess the effect on cell viability as described below.

SW480 colon carcinoma cells were transduced with a lentiviral vector expressing luciferase with a human Sp5 promoter consisting of a sequence of eight TCF/LEF binding sites. SW480 cells stably expressing the Sp5-Luc reporter gene and a hygromycin resistance gene were selected by treatment with 150 µg/mL of hygromycin for 7 days. These stably transduced SW480 cells were expanded in cell culture and used for all further screening activities. Each compound was dissolved in DMSO as a 10 mM stock and used to prepare compound source plates. Serial dilution (1:3, 8-point dose-response curves from 10 µM to 0.0045 µM) and compound transfer was performed using the ECHO 550 (Labcyte, Sunnyvale, Calif.) into 384-well white solid bottom assay plates (Greiner Bio-One) with appropriate DMSO backfill for a final DMSO concentration of 0.1%.

For the Cell Viability Assays, the cells were plated at 2,000 cells/well in 384-well plates with a DMEM medium containing 1% fetal bovine serum, and 1% Penicillin-Streptomycin and incubated for four days hours at 37° C. and 5% CO$_2$. Eight replicates of DMSO-treated cells served as controls and cells treated with compound were performed in duplicate.

After incubation, 10 µL of CellTiter-Glo (Promega) was added to each well allowed to incubate for approximately 12 minutes. This reagent "results in cell lysis and generation of a luminescent signal proportional to the amount of ATP present. The amount of ATP is directly proportional to the number of cells present in culture, in agreement with previous reports. The CellTiter-Glo Assay generates a "glow-type" luminescent signal, produced by the luciferase reaction (Promega.com)".

After incubation, the plates were read at Ex 560 nm Em 590 nm (Cytation 3, BioTek). Dose-response curves were generated and EC$_{50}$ concentration values were calculated using non-linear regression curve fit in the GraphPad Prism (San Diego, Calif.) or Dotmatics' Studies Software (Bishops Stortford, UK). For EC$_{50}$ of >10 µM, the percent inhibition at 10 µM is provided.

Table 5 shows the activity of representative compounds of Formulas (I) and (II) as provided herein.

TABLE 5

| Compound | $EC_{50}$ (μM) |
|---|---|
| 1 | 0.094 |
| 2 | 0.080 |
| 3 | 2.755 |
| 4 | >10 (49.5%) |
| 5 | 0.407 |
| 6 | 0.142 |
| 7 | 0.455 |
| 8 | 0.049 |
| 10 | 0.026 |
| 15 | 0.118 |
| 22 | 0.014 |
| 29 | 0.170 |
| 38 | 0.415 |
| 45 | >10 (44.1%) |
| 51 | 0.515 |
| 57 | 0.670 |
| 64 | >10 (15.8%) |
| 71 | 0.035 |
| 97 | >10 (25.0%) |
| 109 | 0.054 |

Example 11

Representative compounds were screened using primary human fibroblasts (derived from IPF patients) treated with TGF-β1 to determine their ability to inhibit the fibrotic process.

Human Fibroblast Cell Culture:

Primary human fibroblasts derived from IPF patients (LL29 cells) [[1]Xiaoqiu Liu, et. al., "Fibrotic Lung Fibroblasts Show Blunted Inhibition by cAMP Due to Deficient cAMP Response Element-Binding Protein Phosphorylation", *Journal of Pharmacology and Experimental Therapeutics* (2005), 315(2), 678-687; [2]Watts, K. L., et. al., "RhoA signaling modulates cyclin D1 expression in human lung fibroblasts; implications for idiopathic pulmonary fibrosis", *Respiratory Research* (2006), 7(1), 88] were obtained from American Type Culture Collection (ATCC) and expanded in F12 medium supplemented with 15% Fetal Bovine Serum and 1% Penicillin/Streptomycin.

Compound Screening:

Each compound was dissolved in DMSO as a 10 mM stock and used to prepare compound source plates. Serial dilution (1:2, 11-point dose-response curves from 10 μM to 0.94 nM) and compound transfer was performed using the ECHO 550 (Labcyte, Sunnyvale, Calif.) into 384-well clear bottom assay plates (Greiner Bio-One) with appropriate DMSO backfill for a final DMSO concentration of 0.1%. LL29 cells were plated at 1,500 cells/well in 70 μL/well F12 medium supplemented with 1% Fetal Bovine Serum. TGF-β1 (Peprotech; 20 ng/mL) was added to the plates to induce fibrosis (ref. 1 and 2 above). Wells treated with TGF-β1 and containing DMSO were used as positive control, and cells with only DMSO were negative control. Cells were incubated at 37° C. and 5% $CO_2$ for 4 days. Following incubation for 4 days, SYTOX green nucleic acid stain (Life Technologies [Thermo Fisher Scientific]) was added to the wells at a final concentration of 1 μM and incubated at room temperature for 30 min. Cells were then fixed using 4% formaldehyde (Electron Microscopy Sciences), washed 3 times with PBS followed by blocking and permeabilization using 3% Bovine Serum Albumin (BSA; Sigma) and 0.3% Triton X-100 (Sigma) in PBS. Cells were then stained with antibody specific to α-smooth muscle actin (αSMA; Abcam) (ref. 1 and 2 above) in 3% Bovine Serum Albumin (BSA; Sigma) and 0.3% Triton X-100 (Sigma) in PBS, and incubated overnight at 4° C. Cells were then washed 3 times with PBS, followed by incubation with Alexa Flor-647 conjugated secondary antibody (Life Technologies [Thermo Fisher Scientific]) and DAPI in 3% Bovine Serum Albumin (BSA; Sigma) and 0.3% Triton X-100 (Sigma) in PBS at room temperature for 1 hour. Cells were then washed 3 times with PBS and plates were sealed for imaging. αSMA staining was imaged by excitation at 630 nm and emission at 665 nm and quantified using the Compartmental Analysis program on the CellInsight CX5 (Thermo Scientific). Dead or apoptotic cells were excluded from analysis based on positive SYTOX green staining. % of total cells positive for αSMA were counted in each well and normalized to the average of 11 wells treated with TGF-β1 on the same plate using Dotmatics' Studies Software. The normalized averages (fold change over untreated) of 3 replicate wells for each compound concentration were used to create dose-responses curves and $EC_{50}$ values were calculated using non-linear regression curve fit in the Dotmatics' Studies Software. For $EC_{50}$ of >10 μM, the percent inhibition at 10 μM is provided.

Table 6 shows the activity of representative compounds of Formulas (I) and (II) as provided herein.

TABLE 6

| Compound | $EC_{50}$ (μM) |
|---|---|
| 1 | 0.024 |
| 2 | 0.224 |
| 3 | 0.042 |
| 5 | 0.078 |
| 6 | 0.029 |
| 7 | 0.560 |
| 8 | 0.019 |
| 10 | 9.985 |
| 15 | 0.087 |
| 22 | 0.035 |
| 29 | 0.077 |
| 38 | 0.038 |
| 45 | 1.541 |
| 51 | 0.203 |
| 57 | 0.637 |
| 64 | 10 (72.0%) |
| 71 | 0.021 |
| 97 | 0.406 |

Example 12

Representative compounds were screened using the following assay procedure to determine their ability to inhibit IL-6 and therefore demonstrate their anti-inflammatory properties.

Human Peripheral Blood Mononuclear Cells:

Fresh Normal PB MNC (Catalog # PB001, AllCells, Alameda, Calif.) were shipped overnight at 4° C. and resuspended in Roswell Park Memorial Institute (RPMI) 1640 Medium, with GlutaMAX Supplement (Catalog #61870127, ThermoFisher Scientific, Waltham, Mass.) supplemented with 1% Penicillin-Streptomycin (Catalog #15140163, ThermoFisher Scientific, Waltham, Mass.) and 1% fetal bovine serum (FBS) (Catalog #16140089, ThermoFisher Scientific, Waltham, Mass.) assay media.

Compound Screening: Fresh normal human peripheral blood mononuclear cells (huPBMCs) were resuspended in 1% FBS-RPMI assay media with 1% Penicillin-Streptomycin 1% to a cell concentration of 1×10e6 cells/mL. Each compound was dissolved in DMSO (Catalog # D8418-100 ml, Sigma-Aldrich, St. Louis, Mo.) as a 10 mM stock and used to prepare compound source plates. Serial dilution (1:3, 10-point dose-response curves starting from 10 μM) and compound transfer was performed using the ECHO 550 (Labcyte, Sunnyvale, Calif.) into 384-well white Proxiplate-Plus assay plates (Catalog #6008289, PerkinElmer, Shelton, Conn.) with appropriate DMSO backfill for a final DMSO concentration of 0.25%. huPBMCs were plated at 5000 cells/well in the 384-well Proxiplate-Plus assay plates and incubated at 37° C.-5% $CO_2$ for 2 hours. 50 ng/mL of Lipopolysaccharides from *Escherichia coli* 0111:B4 (Catalog # L5293-2ML, Sigma-Aldrich, St. Louis, Mo.) was added after 2 hours and cells were incubated for another 22 hours at 37° C.-5% $CO_2$. After 22 hour incubation, a mixture of anti-IL6 XL665 and anti-IL-6 Cryptate diluted in reconstitution buffer (Catalog #62IL6PEC, Cisbio Inc., Bedford, Mass.) was added to each well. Following incubation for 3 hours at room temperature, Homogeneous Time-Resolved Fluorescence (HTRF) was measured using the Envision (Perkin Elmer, Shelton, Conn.) at 665 nm and 620 nM. The ratio of fluorescence at 665 nm to 620 nm was used as a readout for IL-6 quantification. All samples were processed in duplicate. Readings were normalized to DMSO treated cells and normalized activities were utilized for $EC_{50}$ calculations. $EC_{50}$ was determined using software generated by Dotmatics Limited (Windhill Bishops Stortford Herts, UK) using the Levenberg-Marquardt 4 parameter fitting procedure with finite different gradients. For $EC_{50}$ of >10 μM, the percent inhibition at 10 μM is provided.

Table 7 shows the activity of representative compounds of Formulas (I) and (II) as provided herein.

TABLE 7

| Compound | $EC_{50}$ (μM) |
|---|---|
| 1 | 0.381 |
| 2 | 3.819 |
| 3 | >10 (43.7%) |
| 5 | >10 (9.2%) |
| 6 | >10 (9.5%) |
| 7 | >10 (11.6%) |
| 8 | 0.065 |
| 10 | 0.135 |
| 15 | 0.585 |
| 22 | 0.161 |
| 29 | 0.241 |
| 38 | 0.612 |
| 45 | >10 (5.9%) |
| 51 | 0.414 |
| 57 | 3.009 |
| 64 | >10 (12.7%) |
| 97 | >10 (25.7%) |

Example 13

Representative compounds were screened using primary human mesenchymal stem cells (hMSCs) to determine their ability to induce chondrogenesis (process by which cartilage is developed).

Human Mesenchymal Stem Cell Culture: Primary human mesenchymal stem cells (hMSCs) were purchased from Lonza (Walkersville, Md.) and expanded in Mesenchymal Stem Cell Growth Media (Lonza). Cells between passage 3 and 6 were used for the experiments.

Compound Screening: Each compound was dissolved in DMSO as a 10 mM stock and used to prepare compound source plates. Serial dilution (1:3, 6-point dose-response curves from 2700 nM to 10 nM) and compound transfer was performed using the ECHO 550 (Labcyte, Sunnyvale, Calif.) into 96-well clear bottom assay plates (Greiner Bio-One) with appropriate DMSO backfill for a final DMSO concentration of 0.03%. hMSCs were plated at 20,000 cells/well in 250 μL/well Incomplete Chondrogenic Induction Medium (Lonza; DMEM, dexamethasone, ascorbate, insulin-transferrin-selenium [ITS supplement], gentamycin-amphotericin [GA-1000], sodium pyruvate, proline and L-glutamine). TGF-β3 (10 ng/mL) was used as a positive control for differentiation while negative control wells were treated with 75 nL DMSO for normalization and calculating $EC_{50}$ values. Cells were incubated at 37° C. and 5% $CO_2$ for 6 days. To image chondrogenic nodules, the cells were fixed using 4% formaldehyde (Electron Microscopy Sciences), and stained with 2 μg/mL Rhodamine B (Sigma-Aldrich) and 20 μM Nile Red (Sigma-Aldrich) [Johnson K., et. al, A Stem Cell-Based Approach to Cartilage Repair, *Science*, (2012), 336(6082), 717-721]. The nodules imaged (4 images per well at 4× magnification) by excitation at 531 nm and emission at 625 nm and quantified using the CellInsight CX5 (Thermo Scientific). Number of nodules in each well was normalized to the average of 3 DMSO treated wells on the same plate using Excel (Microsoft Inc.). The normalized averages (fold change over DMSO) of 3 replicate wells for each compound concentration were calculated. Due to solubility limitations of some of the compounds, curve fitting was incomplete leading to inaccurate $EC_{50}$ determinations.

Using TGF-β3 as a positive control, the concentration of representative compounds required to induce equivalent levels of chondrogenesis is reported. In addition, the maximum activity of each compound and the respective dose that each compound reached maximum chondrogenesis activity is reported. Table 8 shows the activity of representative compounds of Formulas (I) and (II) as provided herein.

TABLE 8

| Compound | Conc (nM) of Max. activity | Max. Activity as % TGF-β3 activity | Conc (nM) of 50% TGF-β3 activity |
|---|---|---|---|
| 1 | 5000 | 497 | 200 |
| 3 | 100 | 225 | 50 |
| 8 | 1700 | 558 | 200 |
| 10 | 600 | 607 | 50 |
| 22 | 600 | 440 | 50 |
| 38 | 100 | 185 | 100 |
| 51 | 5000 | 231 | 5000 |

Example 14

Representative compounds were screened using primary human mesenchymal stem cells (hMSCs) to determine their ability to induce chondrogenesis (process by which cartilage is developed).

Human Mesenchymal Stem Cell Culture:

Primary human mesenchymal stem cells (hMSCs) were purchased from Lonza (Walkersville, Md.) and expanded in Mesenchymal Stem Cell Growth Media (Lonza). Cells between passage 2 and 4 were used for the experiments.

Compound Screening:

Each compound was dissolved in DMSO as a 10 mM stock and used to prepare compound source plates. Serial dilution (1:3, 10-point dose-response curves from 5000 nM to 1 nM) and compound transfer was performed using the ECHO 550 (Labcyte, Sunnyvale, Calif.) into 96-well clear bottom assay plates (Greiner Bio-One) with appropriate DMSO backfill for a final DMSO concentration of 0.03%. hMSCs were plated at 20,000 cells/well in 250 μL/well Incomplete Chondrogenic Induction Medium (Lonza; DMEM, dexamethasone, ascorbate, insulin-transferrin-selenium [ITS supplement], gentamycin-amphotericin [GA-1000], sodium pyruvate, proline and L-glutamine). TGF-β3 (10 ng/mL) was used as a positive control for differentiation while negative control wells were treated with 75 nL DMSO for normalization and calculating $EC_{50}$ values. Cells were incubated at 37° C. and 5% $CO_2$ for 6 days. To image chondrogenic nodules, the cells were fixed using 4% formaldehyde (Electron Microscopy Sciences), and stained with 2 µg/mL Rhodamine B (Sigma-Aldrich) and 20 µM Nile Red (Sigma-Aldrich) [Johnson K., et. al, A Stem Cell-Based Approach to Cartilage Repair, Science, (2012), 336(6082). 717-721] and DAPI (4',6-diamidino-2-phenylindole) as a nuclear counterstain. The nodules imaged (16 images per well at 4× magnification) by excitation at 350 nm and emission at 470 nm for DAPI and excitation at 531 nm and emission at 625 nm for Rhodamine B and quantified using the CellInsight CX5 (Thermo Scientific). Rhodamine B staining intensity of nodules in each well was normalized to the average of 3 DMSO treated wells on the same plate using Excel (Microsoft Inc.). The normalized averages (fold change over DMSO) of 3 replicate wells for each compound concentration were calculated. $EC_{50}$ values were calculated using non-linear regression curve fitting in Prism 8 (Graphpad Inc.). Due to solubility limitations of some of the compounds, curve fitting was incomplete, and the highest observed activity was extrapolated to the insoluble doses for accurate $EC_{50}$ determinations.

$EC_{50}$ values are reported. Further, using TGF-β3 as a positive control, the concentration of representative compounds required to induce equivalent levels of chondrogenesis is reported. In addition, the maximum activity of each compound and the respective dose that each compound reached maximum chondrogenesis activity is reported. Table 9 shows the activity of representative compounds of Formulas (I) and (II) as provided herein.

TABLE 9

| Compound | $EC_{50}$ (µM) |
| --- | --- |
| 1 | 0.012 |
| 2 | 0.058 |
| 3 | 0.028 |
| 4 | 0.069 |
| 5 | 0.213 |
| 6 | 0.016 |
| 7 | 0.022 |
| 8 | 0.206 |
| 10 | 0.010 |
| 15 | 0.051 |
| 22 | 0.796 |
| 29 | 0.069 |
| 38 | 0.036 |
| 45 | 0.022 |
| 51 | 0.093 |
| 57 | 0.025 |
| 64 | 0.147 |
| 71 | 3.115 |
| 97 | 0.069 |
| 109 | 0.009 |

What is claimed is:

1. A compound, or a pharmaceutically acceptable salt thereof, of Formula I:

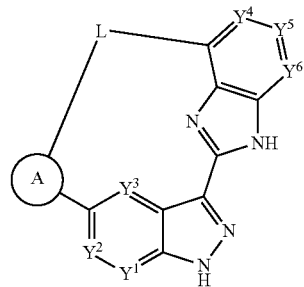

wherein:
Ring A is a 5-6-membered heteroaryl optionally substituted with 1-4 $R^1$;
L is -$L^1$-$L^2$-$L^3$-$L^4$-;
$L^1$ is selected from the group consisting of unsubstituted —($C_{1-3}$ alkylene)-, —$NR^2$—, —$NR^3$(C=O)—, —(C=O)$NR^3$—, and —O—;
$L^2$ is selected from the group consisting of unsubstituted —($C_{1-6}$ alkylene)- and —$NR^2$—;
$L^3$ is selected from the group consisting of unsubstituted —($C_{1-6}$ alkylene)-, —O—, and -carbocyclylene- optionally substituted with one or more halides;
$L^4$ is selected from the group consisting of unsubstituted —($C_{1-6}$ alkylene)-, —O—, —$NR^2$—, —$NR^3$(C=O)—, —(C=O)$NR^3$—, -arylene- optionally substituted with 1-5 $R^4$, and -heteroarylene- optionally substituted with 1-4 $R^5$;
with the proviso that —$NR^2$— and —O— are not adjacent to each other;
with the proviso that two —O— are not adjacent to each other;
with the proviso that two —$NR^3$(C=O)— and/or —(C=O)$NR^3$—, are not adjacent to each other;
each $R^1$ is selected from the group consisting of halide, unsubstituted —($C_{1-3}$ alkyl), unsubstituted —($C_{1-3}$ haloalkyl), and —CN;
each $R^2$ is selected from the group consisting of H and unsubstituted —($C_{1-6}$ alkyl);
each $R^3$ is selected from the group consisting of H and unsubstituted —($C_{1-6}$ alkyl);
each $R^4$ is selected from the group consisting of halide, unsubstituted —($C_{1-6}$ alkyl), unsubstituted —($C_{1-6}$ haloalkyl), and —CN;
each $R^5$ is selected from the group consisting of halide, unsubstituted —($C_{1-6}$ alkyl), unsubstituted —($C_{1-6}$ haloalkyl), and —CN;
$Y^1$, $Y^2$, $Y^3$, $Y^4$, $Y^5$, and $Y^6$ are independently selected from the group consisting of carbon and nitrogen; wherein
if Y is nitrogen then $Y^2$ and $Y^3$ are CH;
if $Y^2$ is nitrogen then $Y^1$ and $Y^3$ are CH;
if $Y^3$ is nitrogen then $Y^1$ and $Y^2$ are CH;
if $Y^4$ is nitrogen then $Y^5$ and $Y^6$ are CH;
if $Y^5$ is nitrogen then $Y^4$ and $Y^6$ are CH; and
if $Y^6$ is nitrogen then $Y^4$ and $Y^5$ are CH.

2. The compound of claim 1, wherein Ring A is pyridinyl.

3. The compound of claim 1, wherein Ring A is pyrazolyl.

4. The compound of claim 1, wherein $L^1$ is selected from the group consisting of —($CH_2$)—, —NH—, —NH(C=O)—, and —O—.

5. The compound of claim 4, wherein $L^2$ is selected from the group consisting of —($CH_2$)—, —($CH_2CH_2$)—, —($CH_2CH_2CH_2$)—, —NH—, and —NMe-.

6. The compound of claim 5, wherein $L^3$ is selected from the group consisting of —(CH$_2$CH$_2$)—, —(CH$_2$CH$_2$CH$_2$)—, —(CH$_2$CH$_2$CH$_2$CH$_2$)—, —O—, and -cyclohexylene-.

7. The compound of claim 6, wherein $L^4$ is selected from the group consisting of —NMe-, —NH(C=O)—, -phenylene-, and -triazolylene-.

8. The compound of claim 7, wherein L is 5-9 atoms in length.

9. The compound of claim 8, wherein L is 7-8 atoms in length.

10. The compound of claim 1, wherein $Y^1$, $Y^2$, $Y^3$, $Y^4$, $Y^5$, and $Y^6$ are all carbon.

11. The compound of claim 1, wherein $Y^2$ is N and $Y^1$, $Y^3$, $Y^4$, $Y^5$, and $Y^6$ are all carbon.

12. The compound of claim 1, wherein $Y^5$ is N and $Y^1$, $Y^2$, $Y^3$, $Y^4$, and $Y^6$ are all carbon.

13. The compound of claim 1, wherein $Y^2$ and $Y^5$ are N and $Y^1$, $Y^3$, $Y^4$, and $Y^6$ are all carbon.

14. The compound of claim 1, wherein the compound of Formula I is selected from the group consisting of:

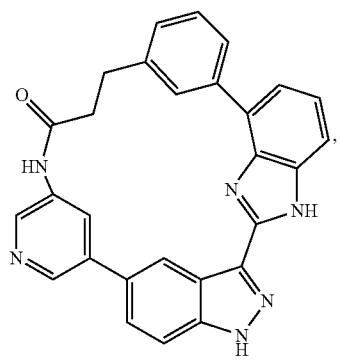

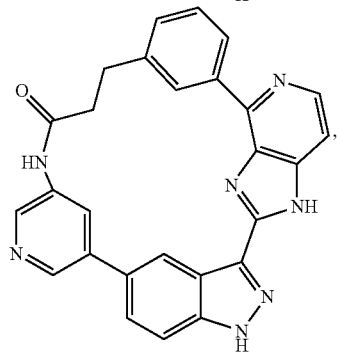

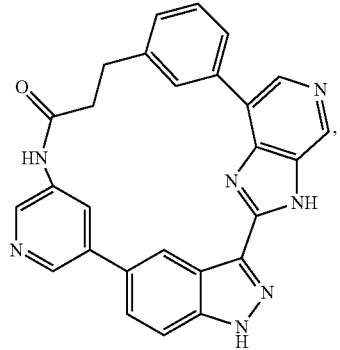

-continued

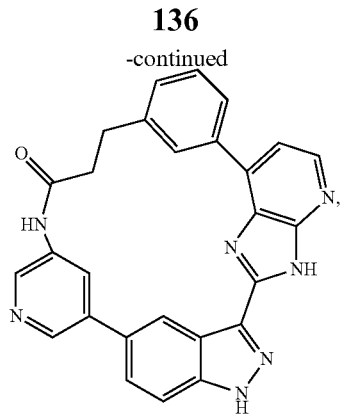

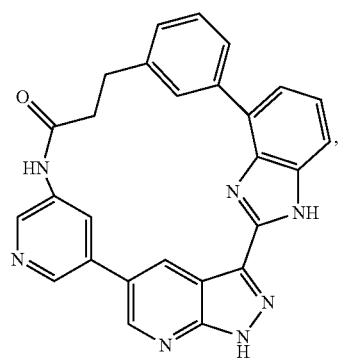

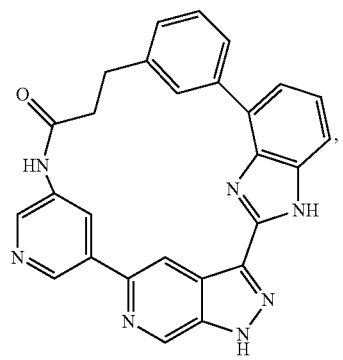

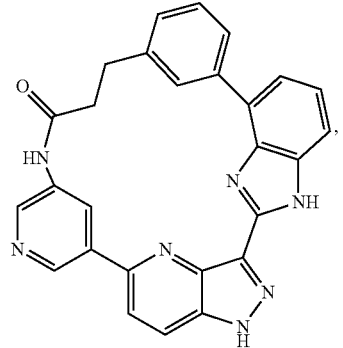

137
-continued
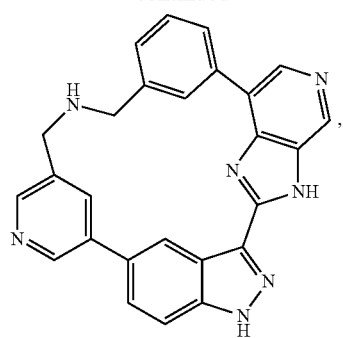,
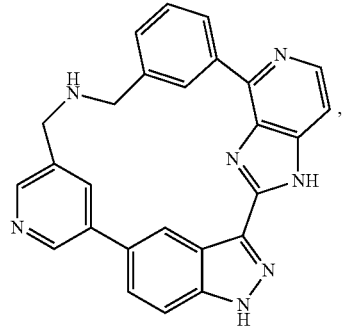,
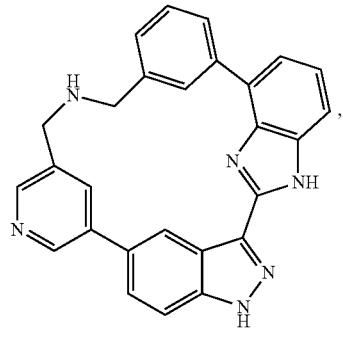,
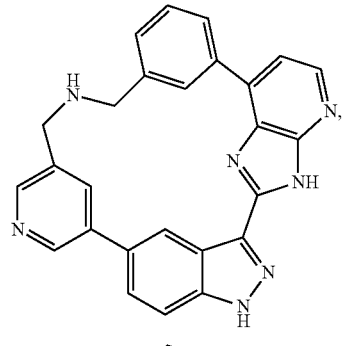,
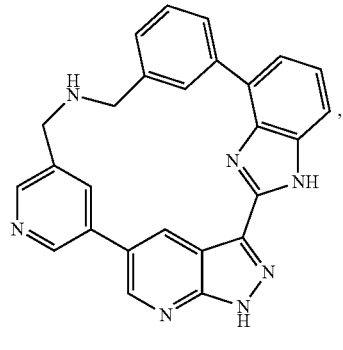,
138
-continued
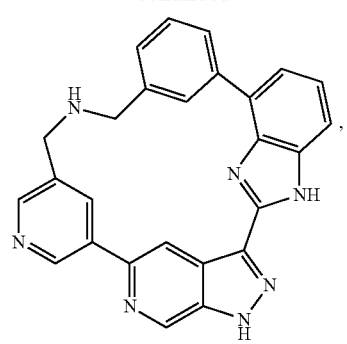,
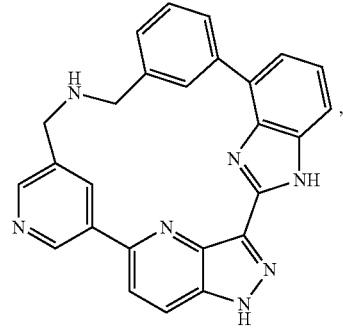,
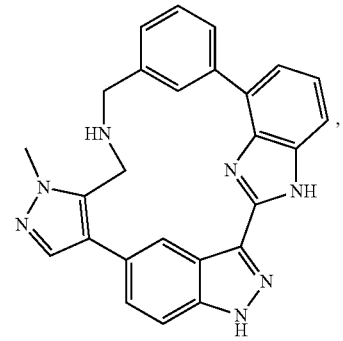,
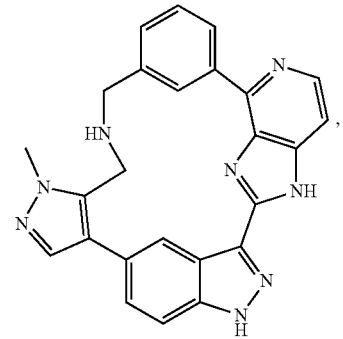,
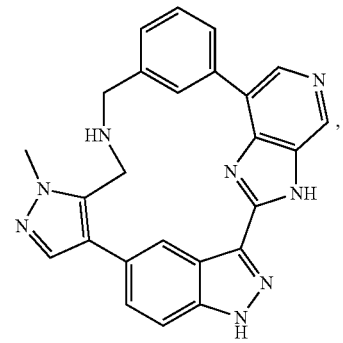,

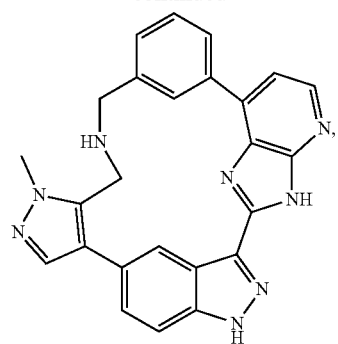
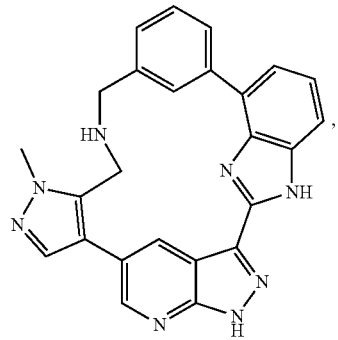
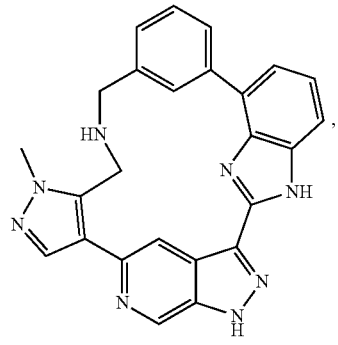
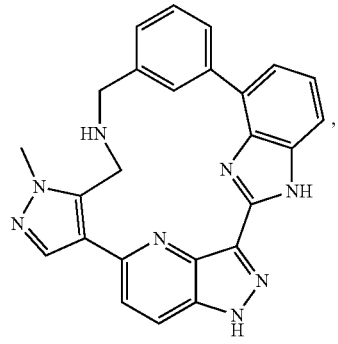
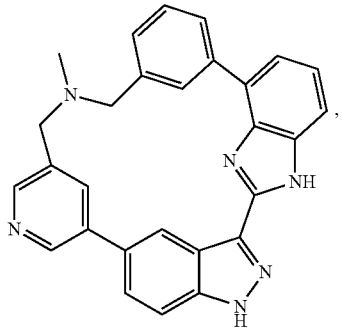
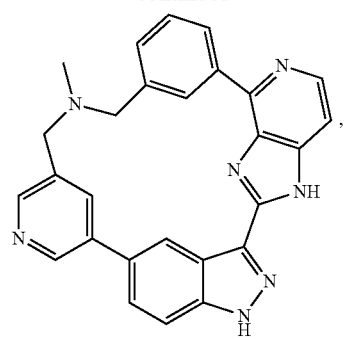
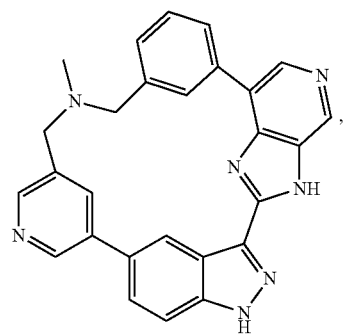
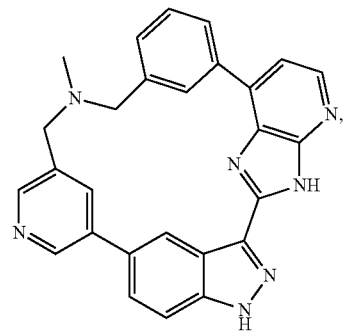
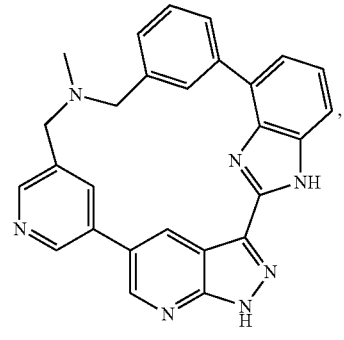
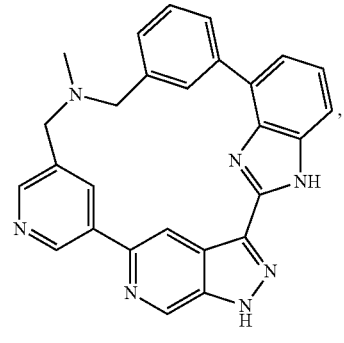

141
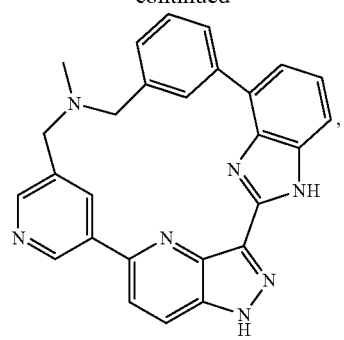
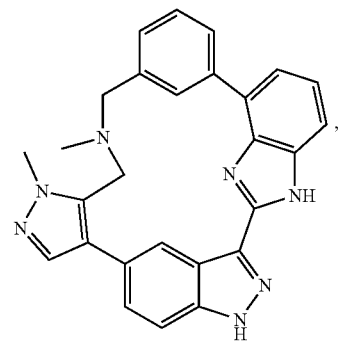
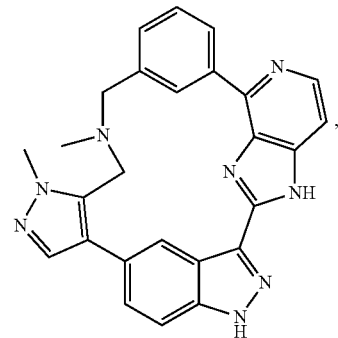
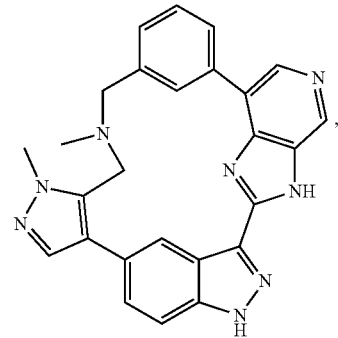
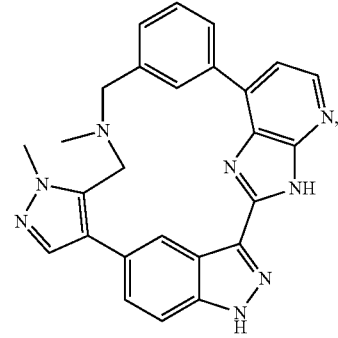
142
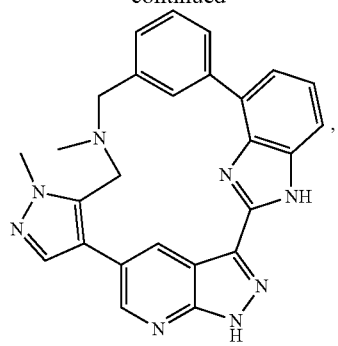
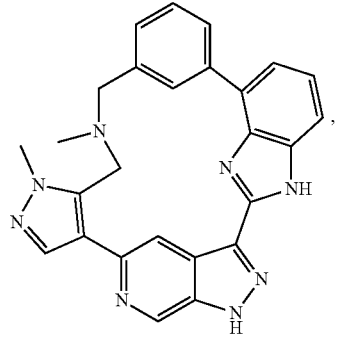
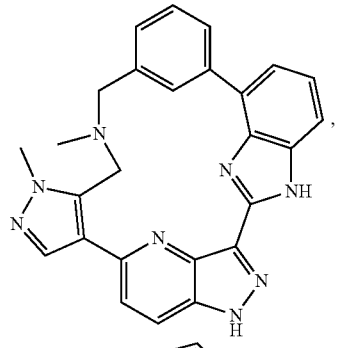
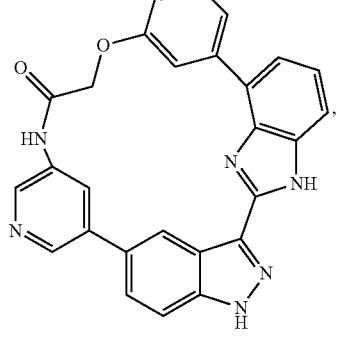
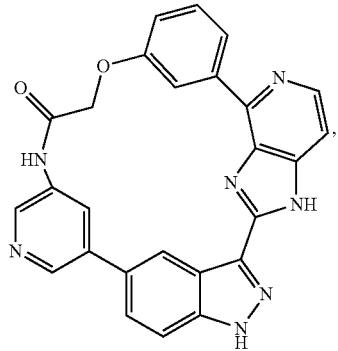

143
-continued
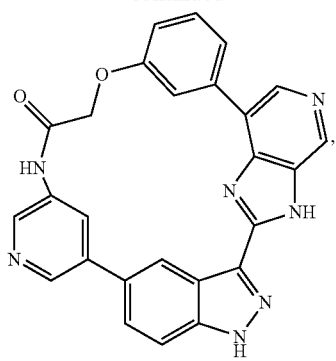
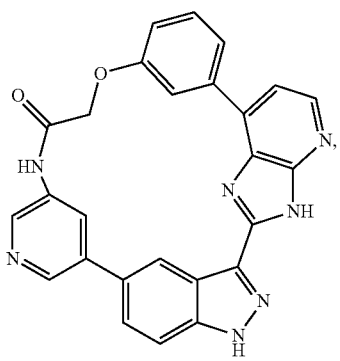
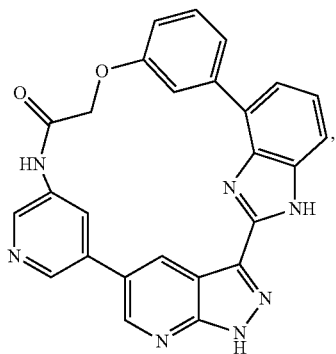
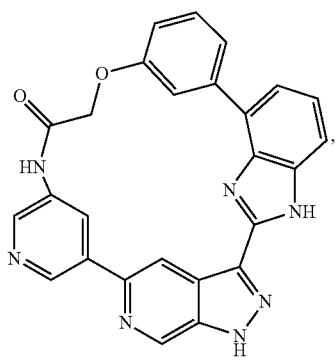
144
-continued
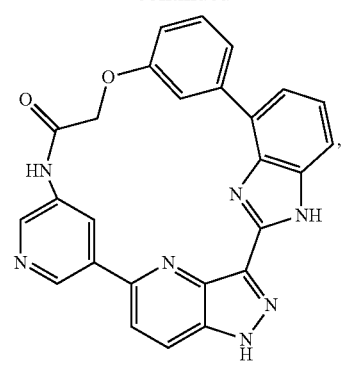
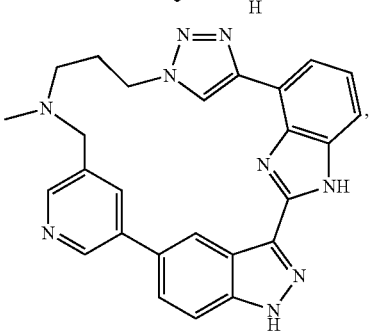
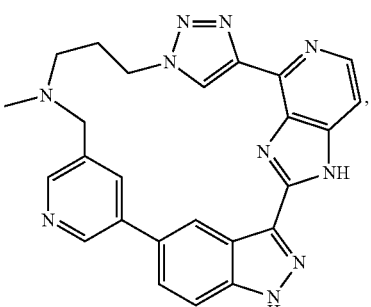
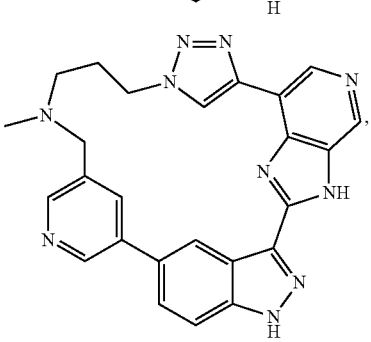
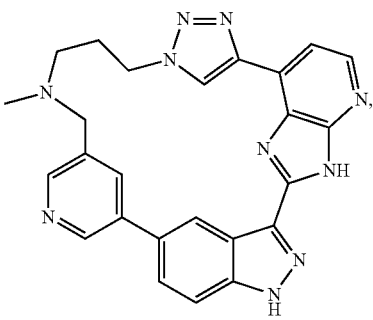

145
-continued
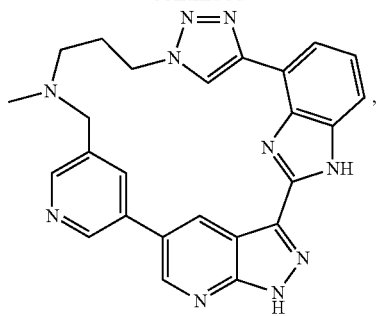
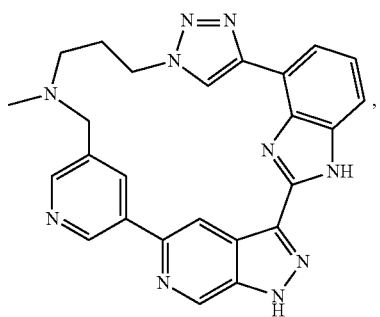
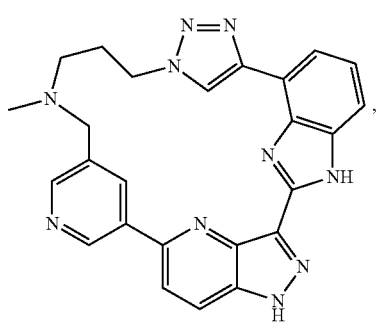
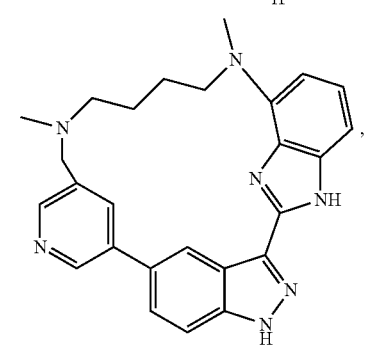
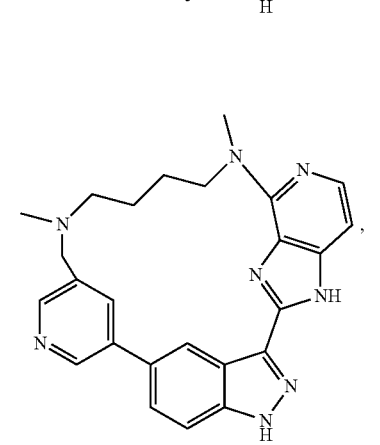
146
-continued
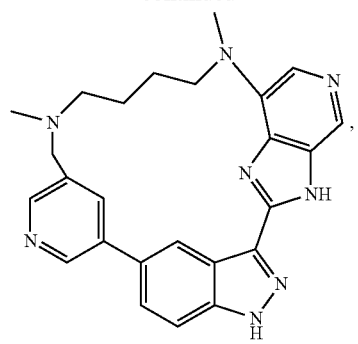
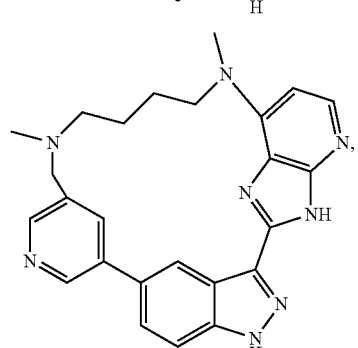
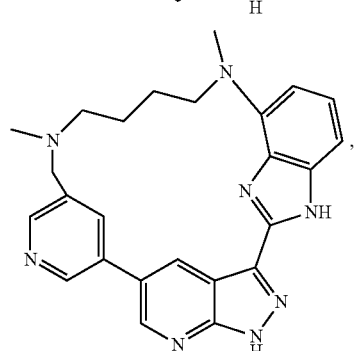
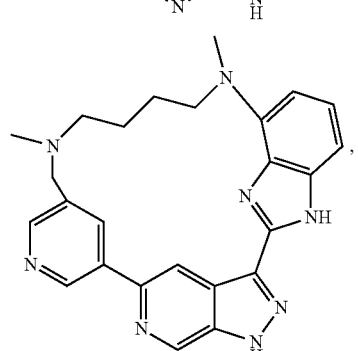
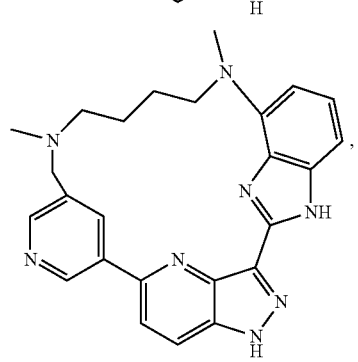

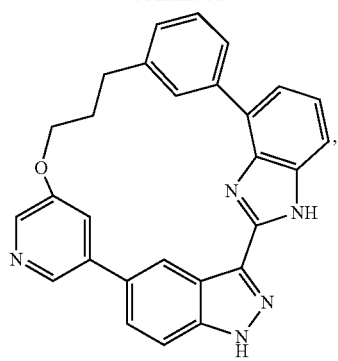
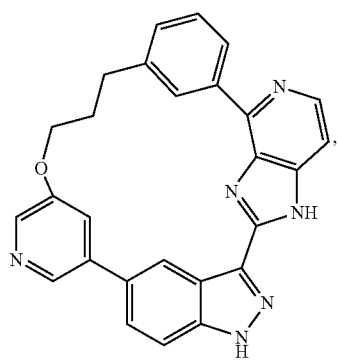
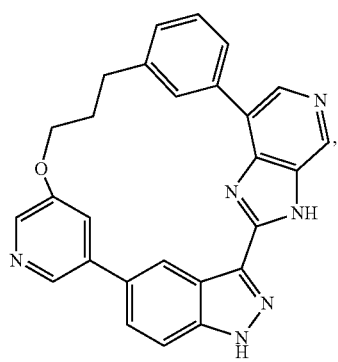
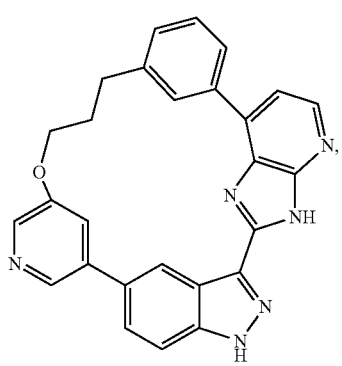
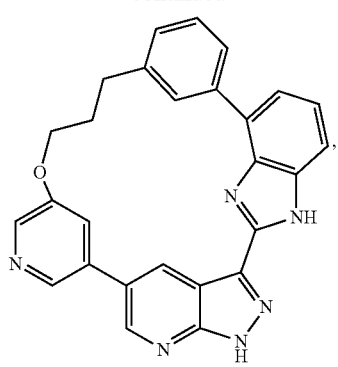
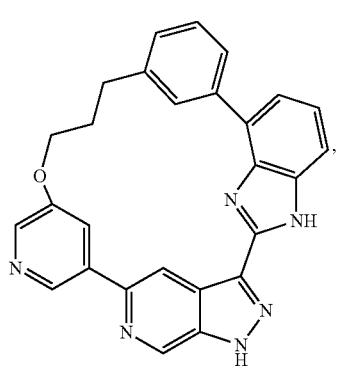
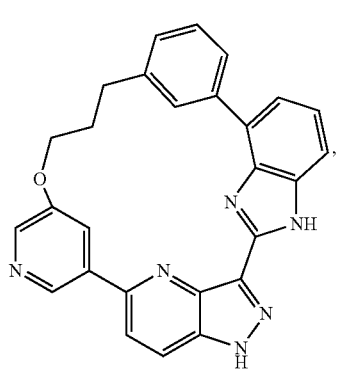
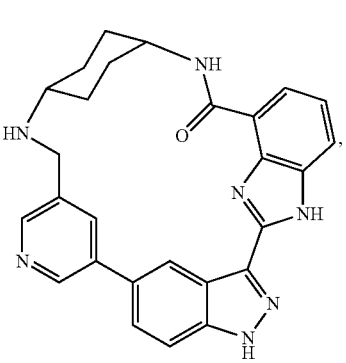

149
-continued
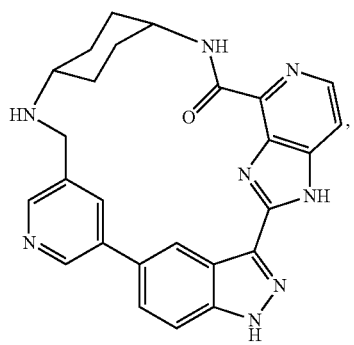
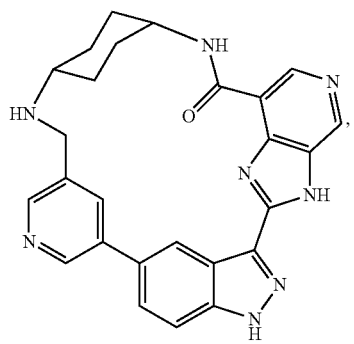
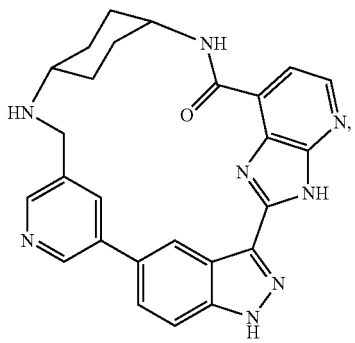
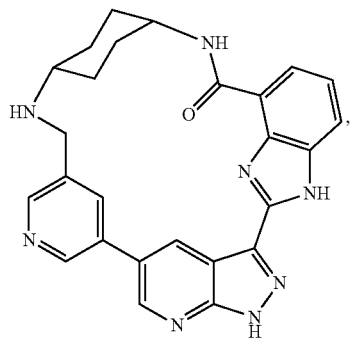
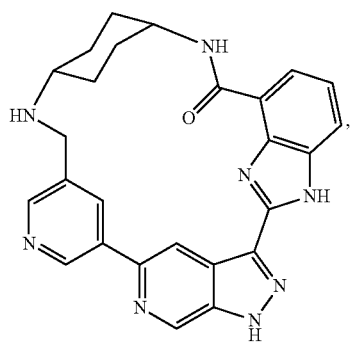
150
-continued
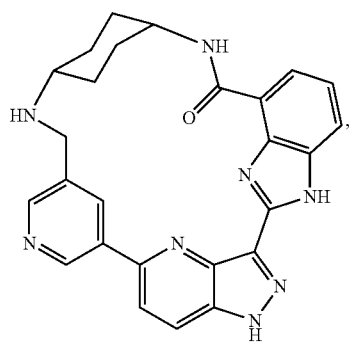
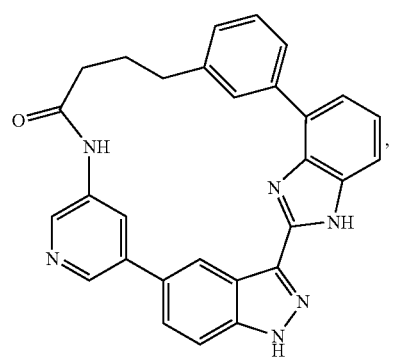
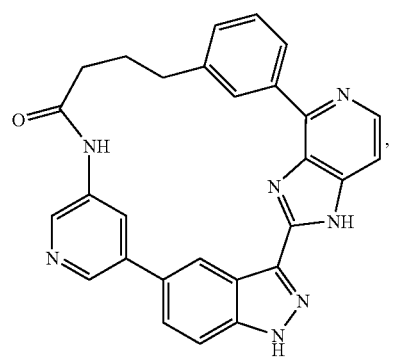
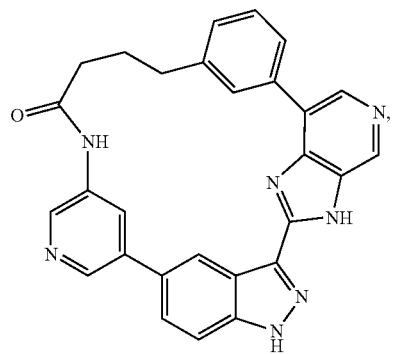

151
-continued
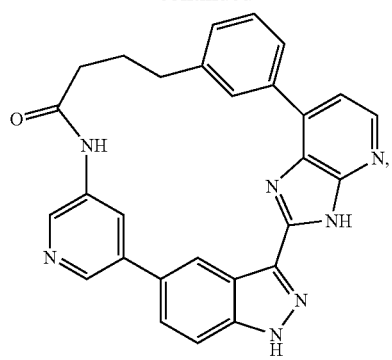
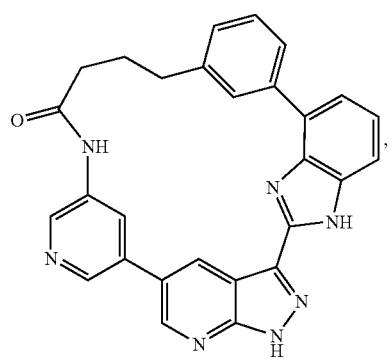
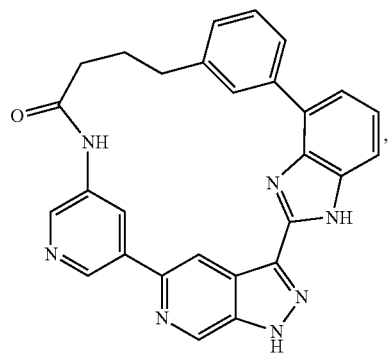
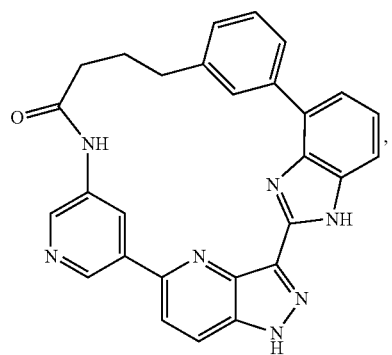
152
-continued
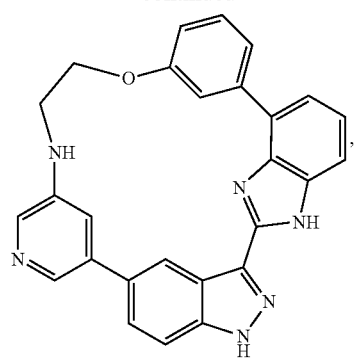
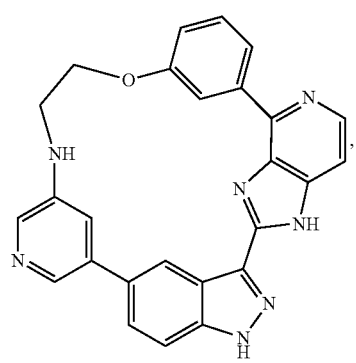
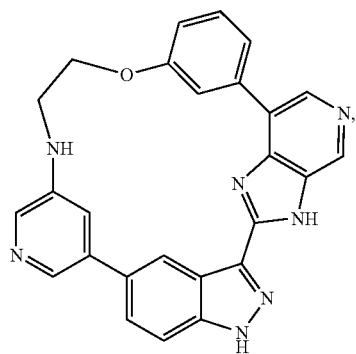
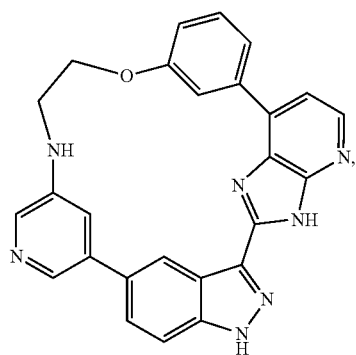

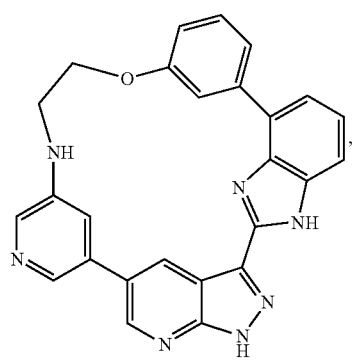

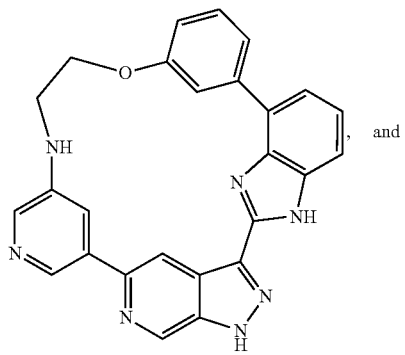
, and

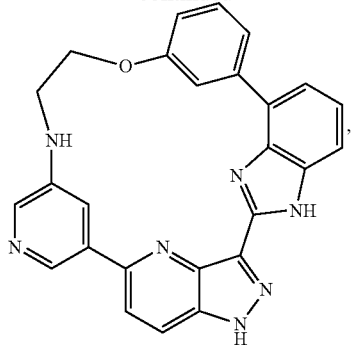

or a pharmaceutically acceptable salt thereof.

15. A pharmaceutical composition comprising a therapeutically effective amount of a compound of claim 1, or a pharmaceutically acceptable salt thereof, and a pharmaceutically acceptable excipient.

16. A method of treating a disorder or disease in a patient, wherein the disorder or disease is selected from the group consisting of: cancer, pulmonary fibrosis, idiopathic pulmonary fibrosis (IPF), degenerative disc disease, bone/osteoporotic fractures, a bone or cartilage disease, osteoarthritis, lung disease, a fibrotic disorder, the method comprising administering to the patient a therapeutically effective amount of a compound of claim 1, or a pharmaceutically acceptable salt, or a pharmaceutical composition.

* * * * *